United States Patent [19]

Rosenberg et al.

[11] Patent Number: 5,929,846
[45] Date of Patent: *Jul. 27, 1999

[54] FORCE FEEDBACK INTERFACE DEVICE INCLUDING GROUNDED SENSOR SYSTEM

[75] Inventors: Louis B. Rosenberg, Pleasanton; Bruce M. Schena, Menlo Park, both of Calif.

[73] Assignee: Immersion Corporation, San Jose, Calif.

[ * ] Notice: This patent is subject to a terminal disclaimer.

[21] Appl. No.: 08/869,584

[22] Filed: Jun. 5, 1997

Related U.S. Application Data

[63] Continuation of application No. 08/560,091, Nov. 17, 1995, Pat. No. 5,805,140, which is a continuation-in-part of application No. 08/374,288, Jan. 18, 1995, Pat. No. 5,731,804, and application No. 08/461,170, Jun. 5, 1995, Pat. No. 5,576,727, which is a continuation of application No. 08/092,974, Jul. 16, 1993, abandoned.

[51] Int. Cl.[6] .............................. G09G 5/08; G06F 3/033
[52] U.S. Cl. ............................................ 345/161; 345/156
[58] Field of Search ...................................... 345/156, 157, 345/161, 184; 434/45; 463/30, 38; 340/407.2; 395/99; 318/568.11, 568.25; 244/223; 74/471

[56] References Cited

U.S. PATENT DOCUMENTS

| 2,906,179 | 9/1959 | Bower ........................................ 90/13.5 |
| 3,490,059 | 1/1970 | Paulsen et al. ............................. 73/133 |
| 3,531,868 | 10/1970 | Stevenson .................................. 33/174 |

(List continued on next page.)

FOREIGN PATENT DOCUMENTS 4-34610  2/1992  Japan .
2254911  10/1992  United Kingdom .
WO9502233  1/1995  WIPO .

(List continued on next page.)

OTHER PUBLICATIONS

Snow, E. et al., "Compact Force–Reflecting Hand Controller," JPL, Apr. 1991, vol. 15, No.3, Item No. 153, pp. 1–15a.

Howe, Robert D., "Task Performance with a Dextrous Teleoperated Hand System," Proceedings of SPIE, Nov. 1992, vol. 1833, pp. 1–9.

(List continued on next page.)

*Primary Examiner*—Jeffery Brier
*Attorney, Agent, or Firm*—James R. Riegel

[57] ABSTRACT

A force feedback interface device and method for use with a host computer includes a user object, such as a joystick handle, physically contacted by a user. A support mechanism allows at least two degrees of freedom to the user object. Two actuators, preferably grounded, provide a force resistance to motion of the user object along the two degrees of freedom in response to commands from the host computer. A grounded sensor system includes an optical detector and a beam source, such as a photo diode sensor, where either the optical detector or the beam source is fixed with respect to the actuator, and the other moves with the user object. The sensor system is configured to detect motion of the user object with respect to a grounding surface in the two rotary degrees of freedom. A local microprocessor, separate from said host computer, can be included to control the actuators and read the sensor and execute a local process in parallel with host execution of a graphical environment.

34 Claims, 25 Drawing Sheets

U.S. PATENT DOCUMENTS

| | | | |
|---|---|---|---|
| 3,795,150 | 3/1974 | Eckhardt | 74/5.4 |
| 3,875,488 | 4/1975 | Crocker et al. | 318/648 |
| 3,890,958 | 6/1975 | Fister et al. | 128/2 S |
| 3,944,798 | 3/1976 | Eaton | 235/151.3 |
| 4,148,014 | 4/1979 | Burson | 340/709 |
| 4,216,467 | 8/1980 | Colston | 340/365 L |
| 4,398,889 | 8/1983 | Lam et al. | 434/45 |
| 4,436,188 | 3/1984 | Jones | 188/378 |
| 4,448,083 | 5/1984 | Hayashi | 73/862.04 |
| 4,477,043 | 10/1984 | Repperger | 244/223 |
| 4,477,973 | 10/1984 | Davies | 33/1 CC |
| 4,550,221 | 10/1985 | Mabusth | 178/18 |
| 4,550,617 | 11/1985 | Fraignier et al. | 73/862.04 |
| 4,571,834 | 2/1986 | Fraser et al. | 33/1 PT |
| 4,601,206 | 7/1986 | Watson | 73/514 |
| 4,632,341 | 12/1986 | Repperger et al. | 244/230 |
| 4,638,798 | 1/1987 | Shelden et al. | 128/303 B |
| 4,653,011 | 3/1987 | Iwano | 364/513 |
| 4,654,648 | 3/1987 | Herrington et al. | 340/710 |
| 4,676,002 | 6/1987 | Slocum | 33/1 MP |
| 4,679,331 | 7/1987 | Koontz | 33/551 |
| 4,688,983 | 8/1987 | Lindbom | 414/735 |
| 4,689,449 | 8/1987 | Rosen | 200/6 |
| 4,703,443 | 10/1987 | Moriyasu | 364/559 |
| 4,704,909 | 11/1987 | Grahn et al. | 73/862.04 |
| 4,712,101 | 12/1987 | Culver | 340/710 |
| 4,750,487 | 6/1988 | Zanetti | 128/303 B |
| 4,769,763 | 9/1988 | Trieb et al. | 364/559 |
| 4,775,289 | 10/1988 | Kazerooni | 414/735 |
| 4,787,051 | 11/1988 | Olson | 364/518 |
| 4,791,934 | 12/1988 | Brunnett | 128/653 |
| 4,798,919 | 1/1989 | Miessler et al. | 178/18 |
| 4,800,721 | 1/1989 | Cemenska et al. | 60/393 |
| 4,803,413 | 2/1989 | Kendig et al. | 318/648 |
| 4,811,608 | 3/1989 | Hilton | 73/862.04 |
| 4,819,195 | 4/1989 | Bell et al. | 364/571.05 |
| 4,839,838 | 6/1989 | LaBiche et al. | 364/709.11 |
| 4,849,692 | 7/1989 | Blood | 324/208 |
| 4,874,998 | 10/1989 | Hollis, Jr. | 318/568.21 |
| 4,879,556 | 11/1989 | Duimel | 341/20 |
| 4,888,877 | 12/1989 | Enderle et al. | 33/559 |
| 4,891,889 | 1/1990 | Tomelleri | 33/503 |
| 4,896,554 | 1/1990 | Culver | 74/471 |
| 4,907,973 | 3/1990 | Hon | 434/262 |
| 4,942,545 | 7/1990 | Sapia | 364/571.01 |
| 4,945,305 | 7/1990 | Blood | 324/207.17 |
| 4,945,501 | 7/1990 | Bell et al. | 364/571.05 |
| 4,961,138 | 10/1990 | Gorniak | 364/200 |
| 4,961,267 | 10/1990 | Herzog | 33/503 |
| 4,962,591 | 10/1990 | Zeller et al. | 33/502 |
| 4,982,504 | 1/1991 | Söderberg et al. | 33/502 |
| 4,983,786 | 1/1991 | Stevens et al. | 178/18 |
| 4,985,652 | 1/1991 | Oudet et al. | 310/15 |
| 5,007,085 | 4/1991 | Greanias et al. | 380/25 |
| 5,007,300 | 4/1991 | Siva | 74/471 XY |
| 5,040,306 | 8/1991 | McMurty et al. | 33/556 |
| 5,044,956 | 9/1991 | Behensky et al. | 434/45 |
| 5,050,608 | 9/1991 | Watanabe et al. | 128/653 R |
| 5,088,046 | 2/1992 | McMurtry et al. | 364/474.03 |
| 5,088,055 | 2/1992 | Oyama | 364/560 |
| 5,095,303 | 3/1992 | Clark et al. | 340/710 |
| 5,103,404 | 4/1992 | McIntosh | 318/568.22 |
| 5,107,080 | 4/1992 | Rosen | 200/6 |
| 5,116,051 | 5/1992 | Moncrief et al. | 273/448 B |
| 5,126,948 | 6/1992 | Mitchell et al. | 364/474.03 |
| 5,128,671 | 7/1992 | Thomas, Jr. | 341/20 |
| 5,131,844 | 7/1992 | Marinaccio et al. | 433/72 |
| 5,132,672 | 7/1992 | Clark | 340/710 |
| 5,136,194 | 8/1992 | Oudet et al. | 310/15 |
| 5,139,261 | 8/1992 | Openiano | 273/148 B |
| 5,142,506 | 8/1992 | Edwards | 367/127 |
| 5,142,931 | 9/1992 | Menahem | 74/471 XY |
| 5,143,505 | 9/1992 | Burdea et al. | 414/5 |
| 5,148,377 | 9/1992 | McDonald | 364/560 |
| 5,178,012 | 1/1993 | Culp | 73/510 |
| 5,181,181 | 1/1993 | Glynn | 364/566 |
| 5,182,557 | 1/1993 | Lang | 341/20 |
| 5,184,306 | 2/1993 | Erdman et al. | 364/474.05 |
| 5,184,319 | 2/1993 | Kramer | 364/806 |
| 5,185,561 | 2/1993 | Good et al. | 318/432 |
| 5,186,629 | 2/1993 | Rohen | 434/114 |
| 5,187,874 | 2/1993 | Takahashi et al. | 33/502 |
| 5,189,806 | 3/1993 | McMurtry et al. | 33/503 |
| 5,204,824 | 4/1993 | Fujimaki | 364/474.03 |
| 5,209,131 | 5/1993 | Baxter | 73/865.8 |
| 5,220,260 | 6/1993 | Schuler | 318/561 |
| 5,223,776 | 6/1993 | Radke et al. | 318/568.1 |
| 5,228,356 | 7/1993 | Chuang | 74/471 XY |
| 5,230,623 | 7/1993 | Guthrie et al. | 433/72 |
| 5,251,127 | 10/1993 | Raab | 364/413.13 |
| 5,251,156 | 10/1993 | Heier et al. | 364/559 |
| 5,259,120 | 11/1993 | Chapman et al. | 33/502 |
| 5,259,894 | 11/1993 | Sampson | 156/64 |
| 5,262,777 | 11/1993 | Low et al. | 341/20 |
| 5,264,768 | 11/1993 | Gregory et al. | 318/561 |
| 5,275,565 | 1/1994 | Moncrief | 434/29 |
| 5,296,846 | 3/1994 | Ledley | 345/161 |
| 5,351,692 | 10/1994 | Dow et al. | 128/662.06 |
| 5,354,162 | 10/1994 | Burdea et al. | 414/5 |
| 5,379,663 | 1/1995 | Hara | 74/471 XY |
| 5,384,460 | 1/1995 | Tseng | 250/231.14 |
| 5,389,865 | 2/1995 | Jacobus et al. | 318/568.11 |
| 5,396,266 | 3/1995 | Brimhall | 345/161 |
| 5,396,267 | 3/1995 | Bouton | 345/168 |
| 5,402,582 | 4/1995 | Raab | 33/503 |
| 5,405,152 | 4/1995 | Katanics et al. | 273/438 |
| 5,412,880 | 5/1995 | Raab | 33/503 |
| 5,414,337 | 5/1995 | Schuler | 318/561 |
| 5,417,696 | 5/1995 | Kashuba et al. | 606/9.1 |
| 5,428,748 | 6/1995 | Davidson | 395/275 |
| 5,429,140 | 7/1995 | Burdea et al. | 128/774 |
| 5,436,542 | 7/1995 | Petelin et al. | 318/567 |
| 5,436,640 | 7/1995 | Reeves | 345/161 |
| 5,445,166 | 8/1995 | Taylor | 128/897 |
| 5,451,924 | 9/1995 | Massimino et al. | 340/407.1 |
| 5,459,382 | 10/1995 | Jacobus et al. | 318/568.11 |
| 5,467,763 | 11/1995 | McMahon et al. | 600/201 |
| 5,512,919 | 4/1996 | Araki | 345/156 |
| 5,513,100 | 4/1996 | Parker et al. | 364/167 |
| 5,532,585 | 7/1996 | Oudet et al. | 324/207.22 |
| 5,576,727 | 11/1996 | Rosenberg et al. | 345/179 |
| 5,587,937 | 12/1996 | Massie et al. | 364/578 |
| 5,589,828 | 12/1996 | Armstrong | 341/20 |
| 5,589,854 | 12/1996 | Tsai | 345/161 |
| 5,591,924 | 1/1997 | Hilton | 73/862.043 |
| 5,623,582 | 4/1997 | Rosenberg | 395/99 |
| 5,629,594 | 5/1997 | Jacobus et al. | 318/568 |
| 5,642,469 | 6/1997 | Hannaford et al. | 395/99 |
| 5,666,138 | 9/1997 | Culver | 345/161 |
| 5,721,566 | 2/1998 | Rosenberg et al. | 345/161 |
| 5,731,804 | 3/1998 | Rosenberg | 345/156 |
| 5,734,373 | 3/1998 | Rosenberg et al. | 345/161 |
| 5,739,811 | 4/1998 | Rosenberg et al. | 345/161 |
| 5,754,023 | 5/1998 | Roston et al. | 318/561 |
| 5,755,577 | 5/1998 | Gillio | 434/262 |
| 5,767,839 | 6/1998 | Rosenberg | 345/161 |

FOREIGN PATENT DOCUMENTS

| | | |
|---|---|---|
| WO9520787 | 8/1995 | WIPO . |
| WO9520788 | 8/1995 | WIPO . |
| WO9532459 | 11/1995 | WIPO . |

OTHER PUBLICATIONS

Jones, L.A. et al., "A Perceptual Analysis of Stiffness," Experimental Brain Research 1990, pp. 151–156.

Buttolo et al., "Hard Disk Actuators for Mini Teleoperation", Proceedings SPIE Telemanipulator and Telepresence Technologies, Oct. 31, 1994, pp. 1–8.

Kilpatrick, Paul Jerome, "The Use of a Kinesthetic Supplement in an Interactive Graphics System", University of North Carolina at Chapel Hill, 1976.

Winey III, Calvin Mccoy, "Computer Simulated Visual and Tactile Feedback as an Aid to Manipulator and Vehicle Control," MIT, Jun. 1981.

Jacobsen, S.C. et al., "High Performance, High Dexterity, Force Reflective Teleoperator II," ANS Topical Meeting on Robotics & Remote Systems, Albuquerque, New Mexico Feb. 24–27, 1991, pp. 1–10.

Kotoku, Tetsuo et al., "Environment Modeling for the Interactive Display (EMID) Used in Telerobotic Systems," IEEE Nov. 3–5, 1991, pp. 99–1004.

Bejczy, Antal K., "The Phantom Robot: Predictive Displays for Teleoperation with Time Delay," IEEE 1990, pp. 546–550.

Buttolo, Pietro et al., "Pen–Based Force Display for Precision Manipulation in Virtual Environments," IEEE Mar. 1995, pp. 1–8.

Tan, Hong Z. et al., "Human Factors for the Design of Force–Reflecting Haptic Interfaces," Tan, Srinivasan, Eberman, & Chang, ASME WAM 1994, pp. 1–11.

Ellis, R.E. et al., "Design and Evaluation of a High–Performance Prototype Planar Haptic Interface," ASME Dec. 3, 1993, DSC–vol. 49, pp. 55–64.

Adelstein Bernard D. et al., "A High Performance Two Degree–of–Freedom Kinesthetic Interface," Massachusetts Institute of Technology 1992, pp. 108–112.

Colgate J. Edward et al., Implementation of Stiff Virtual Walls in Force–Reflecting Interfaces, Sep. 22, 1993.

Iwata, Hiroo et al, Volume Haptization, IEEE 1993, pp. 16–18.

Fischer, Patrick et al., "Specification and Design of Input Devices for Teleoperation," 1990.

Burdea, Grigore et al., "Distributed Virtual Force Feedback," IEEE, May 2, 1993, pp. 25–44.

Rosenberg, Louis B., "The Use of Virtual Fixtures as Perceptual Overlays to Enhance Operator Performance in Remote Environments," Air Force Material Command, Sep. 1992, pp. 1–42.

Rosenberg, Louis B., The Use of Virtual Fixtures to Enhance Operator Performance in Time Delayed Teleoperation, Mar. 1993, pp. 1–45.

Rosenberg, Louis B., "Perceptual Design of a Virtual Rigid Surface Contact," Center for Design Reseach Standford University, Air Force Material Command, Apr. 1993, pp. 1–41.

Rosenberg, Louis B. et al., "Perceptual Decomposition of Virtual Haptic Surfaces," IEEE, Oct. 1993.

Rosenberg, Louis B., "Virtual Fixtures as Tools to Enhance Operator Performance in Telepresence Environments," SPIE Telemanipulator Technology, Mar. 1993.

Rosenberg, Louis B., "Virtual Haptic Overlays Enhance Performance in Telepresence Tasks," SPIE 1994.

Burdea, Grigore et al., "Dextrous Telerobotics with Force Feedback–An Overview," Robotica 1991, vol. 9.

Colgate, J. Edward et al., "Implementation of Stiff Virtual Walls in Force–Reflecting Interfaces," 1993, pp. 1–9.

Yamakita, M. et al., Tele–Virtual Reality of Dynamic Mechanical Model, IEEE Jul. 7–10, 1992, pp. 1103–1110.

Adlestein, Bernard D. et al., "Design and Implementation of a Force Reflecting Manipulandum for Manual Control Research," 1992, pp. 1–24.

Ouh–young, Ming, et al., "Force Display Performs Better than Visual Display in a Simple 6–D Docking Task," IEEE 1989, pp. 1462–1466.

Kim, Won S. et al., "Graphics Displays for Operator Aid in Telemanipulation," IEEE 1991, pp. 1059–1067.

Hannaford, Blake et al., "Performance Evaluation of a Six–Axis Generalized Force–Reflecting Teleoperator," IEEE May/Jun. 1991, vol. 21, No. 3, pp. 620–633.

Kim, Won S. et al., A Teleoperation Training Simulator with Visual and Kinesthetic Force Virtual Reality.

Burdea, Grigore et al., "A Portable Dextrous Master with Force Feedback," Presence: Teleoperators and Virtual Environments, MIT Press, Jun. 1991.

Fisher, S.S. et al., "Virtual Environment Display System," ACM Interactive 3D Graphics, Oct. 1986.

"The Personal Digitizer™," Immersion Human Interface Corporation 1994.

"High Performance Model of the Immersion Probe," Immersion Probe–MD™, Immersion Human Interface Corporation.

3D Human Interface Tool, Immersion Probe ™, Immersion Human Interface Corporation 1994.

Meyer, Kenneth et al., "A Survey of Position Trackers," The Massachusetts Institute of Technology 1992, Presence, vol. 1, No. 2.

"Useful Technology for Your Idea File," Design News, Mar. 7, 1994, pp. 63.

Smith, Geoffrey, "Call It Palpable Progress," Business Week, Oct. 9, 1995, p. 93, 96.

Minsky, Margaret et al., "Feeling and Seeing: Issues in Force Display," ACM 1990, pp. 235–242.

Herndon , J.N. et al., "The State–of–the–Art Model M–2 Maintenance System," Proceedings of the 1984 National Topical Meeting on Robotics and Remote Handling in Hostile Environments, American Nuclear Society, pp. 59–65.

Batter, James J. et al., "Grope–1: A Computer Display to the Sense of Feel," pp. TA–4–188–TA–4–192.

Gotow, J.K., et al., "Perception of Mechanical Properties at the Man–Machine Interface," IEEE 1987, pp. 688–689.

"Proceedings of the IFIP Congress 65, " International Federation for Information Processing, Information Processing 1965, vol. 3, New York, May 24–29, 1965, pp. 506.

Atkinston, William D. et al, "Computing with Feeling," Comput. & Graphics, vol. 2, No. 2–E, pp. 97–103.

Noll, A. Michael, "Man–Machine Tactile Communication Dissertation," Polytechnic Institute of Brooklyn, Jun. 1971, pp. 1–88.

Ouh–Young, Ming, "Force Display in Molecular Docking," Chapel Hill 1990, pp. 1–85.

Ouh–young, Ming et al., "Using a Manipulator for Force Display in Molecular Docking," IEEE 1988, pp. 1824–1829.

Wiker, Steven F. et al., "Development of Tactile Mice for Blind Access to Computers: Importance of Stimulation Locus, Object Size, and Vibrotactile Display Resolution," Proceedings of the Human Factors Society 35th Annual Meeting 1991, pp. 708–712.

Krueger, Myron W., Artificial Reality 1988, pp. 54–57.

Tavkhelidze, D.S. "Kinematic Analysis of Five–Link Spherical Mechanisms," Mechanism and Machine Theory 1974, vol. 9, pp. 181–190.

"Foot–Operated Mouse," IBM Technical Disclosure Bulletin, Apr. 1986, vol. 28, No. 11.

Slocum, Alexander H., Precision Machine Design, Prentice Hall, 1992, pp. 661–664.

"12–V Voice Coil Motor Driver," Si9961 Jun. 6, 1994, pp. 4–10–4–16.

Schmult, Brian et al., "Application Areas for a Force–Feedback Joystick," ASME 1993, DSC–vol. 49, pp. 47–54.

McAffee, Douglas A., "Teleoperator System/Telerobot Demonstrator: Force Reflecting Hand Controller Equipment Manual," JPL Jan. 1988, pp. 3–8, 11, and A–34.

Russo, Massimo A., "The Design and Implementation of a Three Degree–of–Freedom Force Output Joystick," Dept. of Mechanical Engineering, May 11, 1990, pp. 9–40, 96, 97.

Iwata, Hiroo, "Pen–based Haptic Virtual Environment," Institute of Engineering Mechanics, University of Tsukuba, Japan, pp. 287–292.

Tan, H. et al., "Manual Resolution of Compliance When Work and Force Cues are Minimized," ASME 1993, DSC–vol. 49, pp. 99–104.

Kotoku, Tetsuo, "A Predictive Display with Force Feedback and its Application to Remote Manipulation System with Transmission Time Display," IEEE 1992, Jul. 7–10, 1992, pp. 239–246.

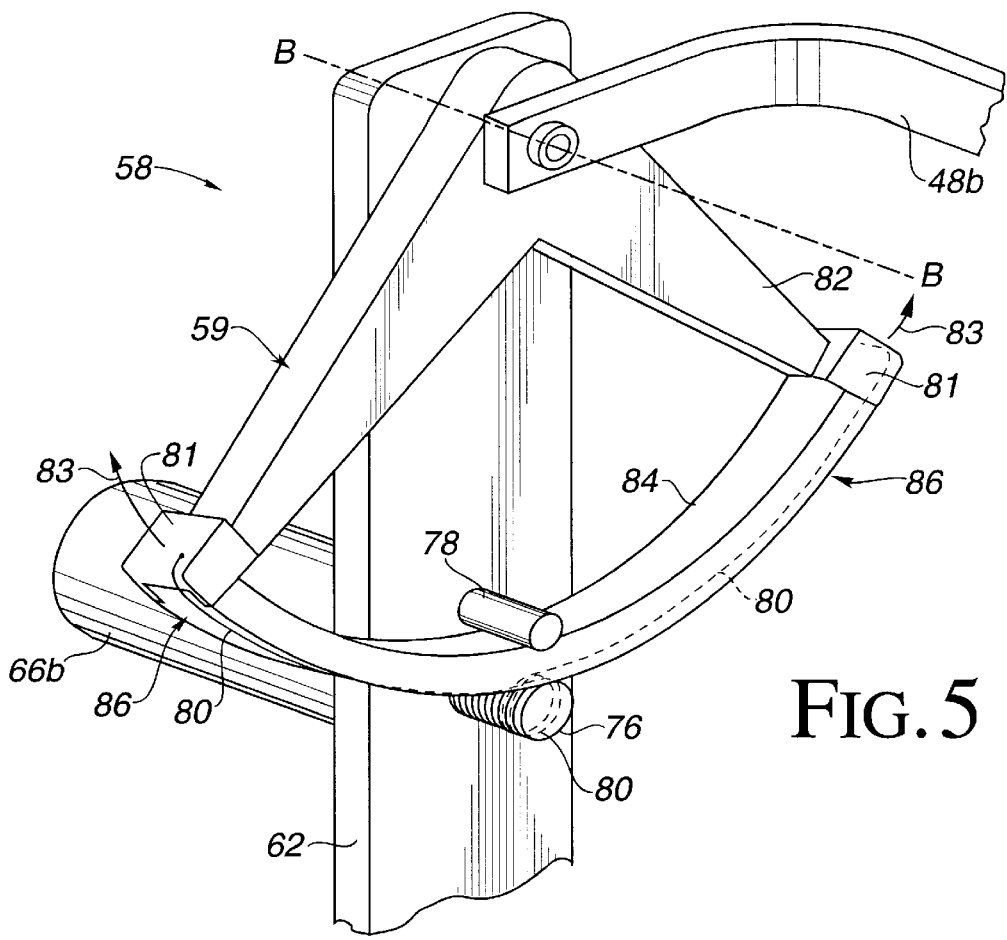
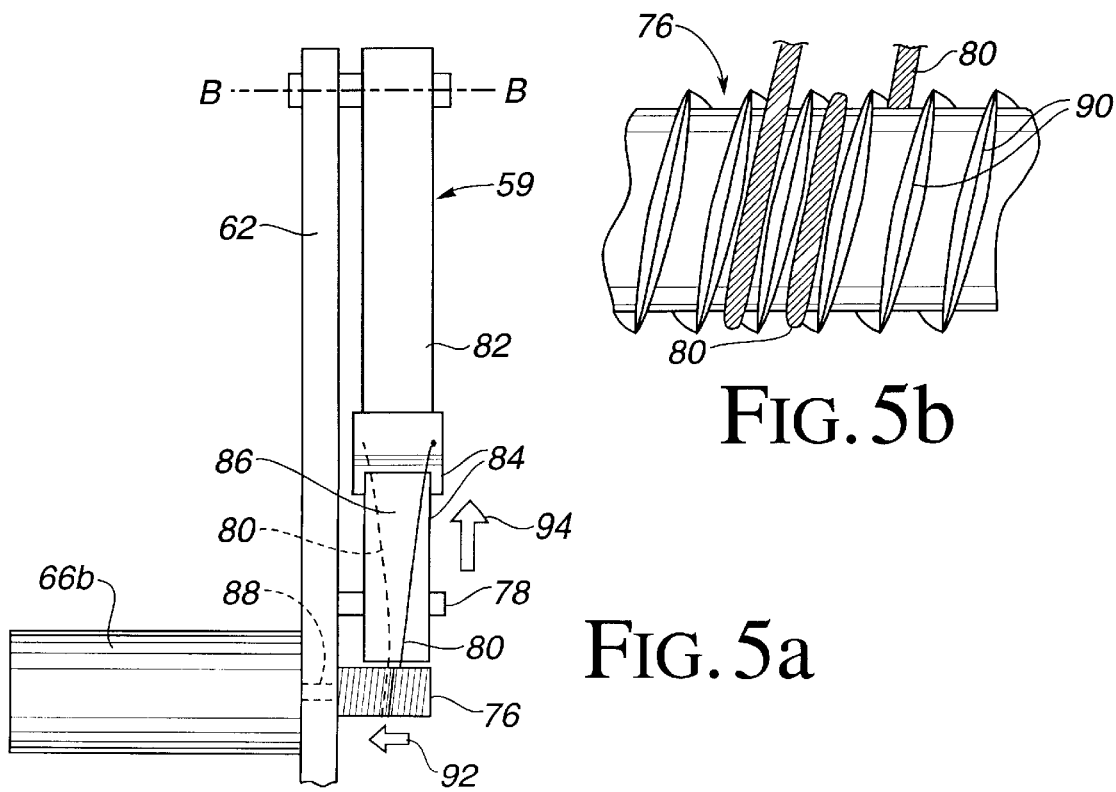
FIG. 5
FIG. 5a
FIG. 5b

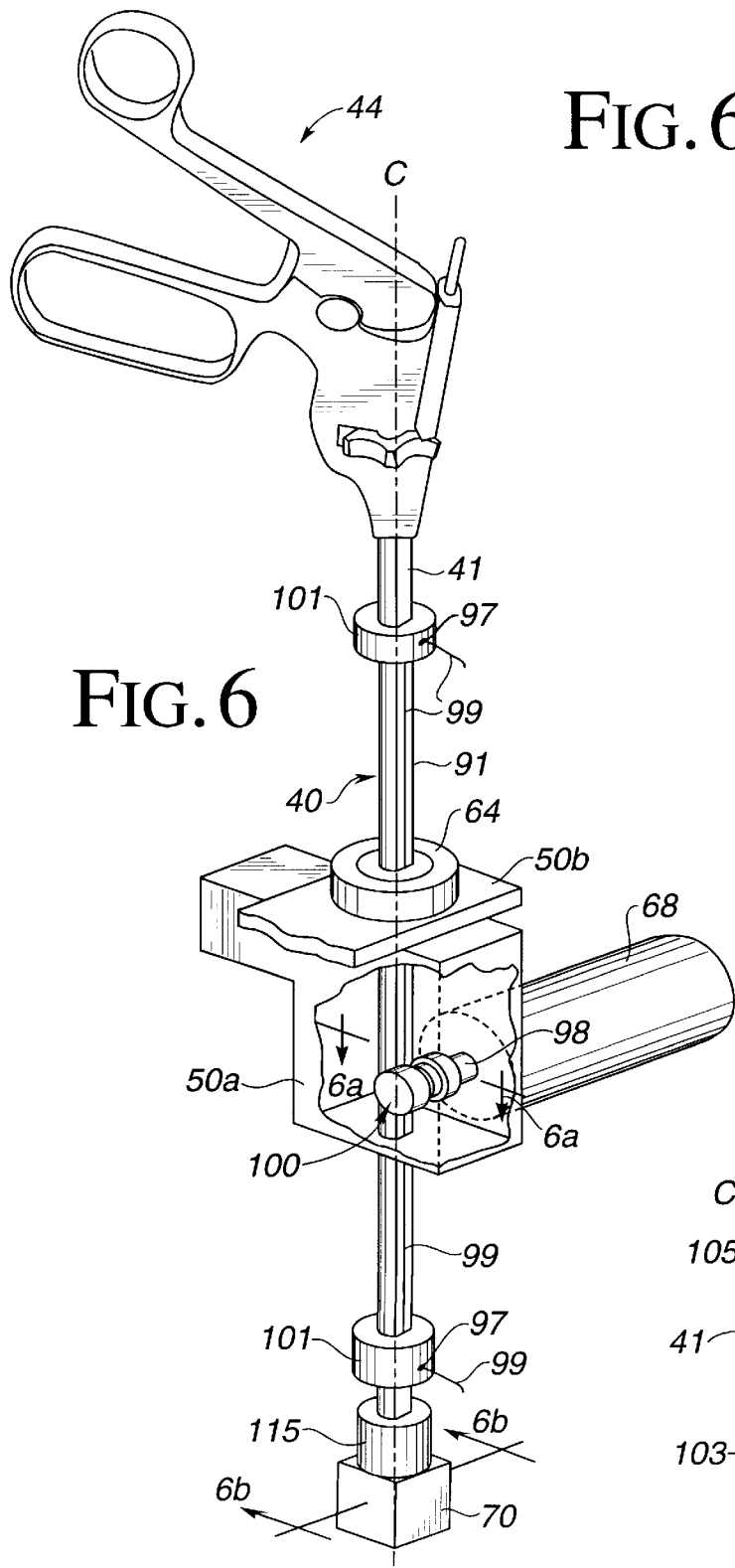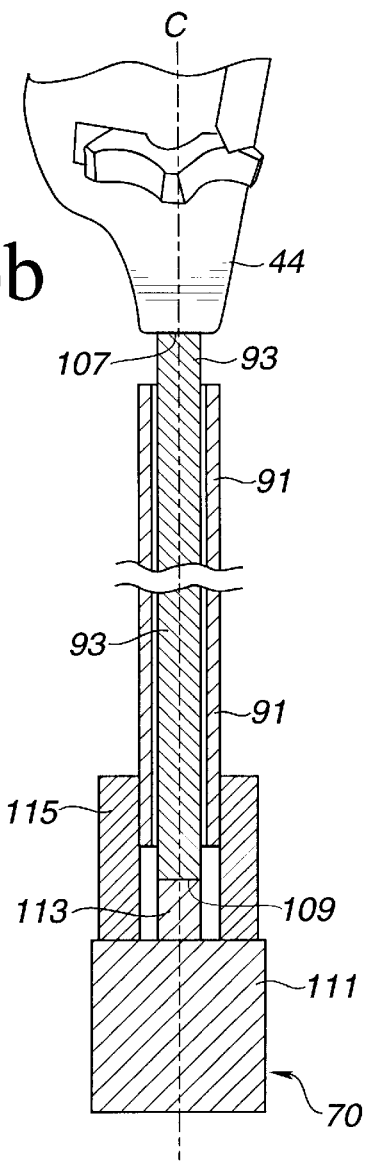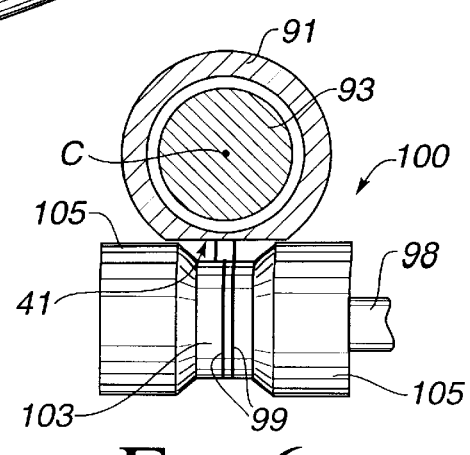
FIG. 6
FIG. 6a
FIG. 6b

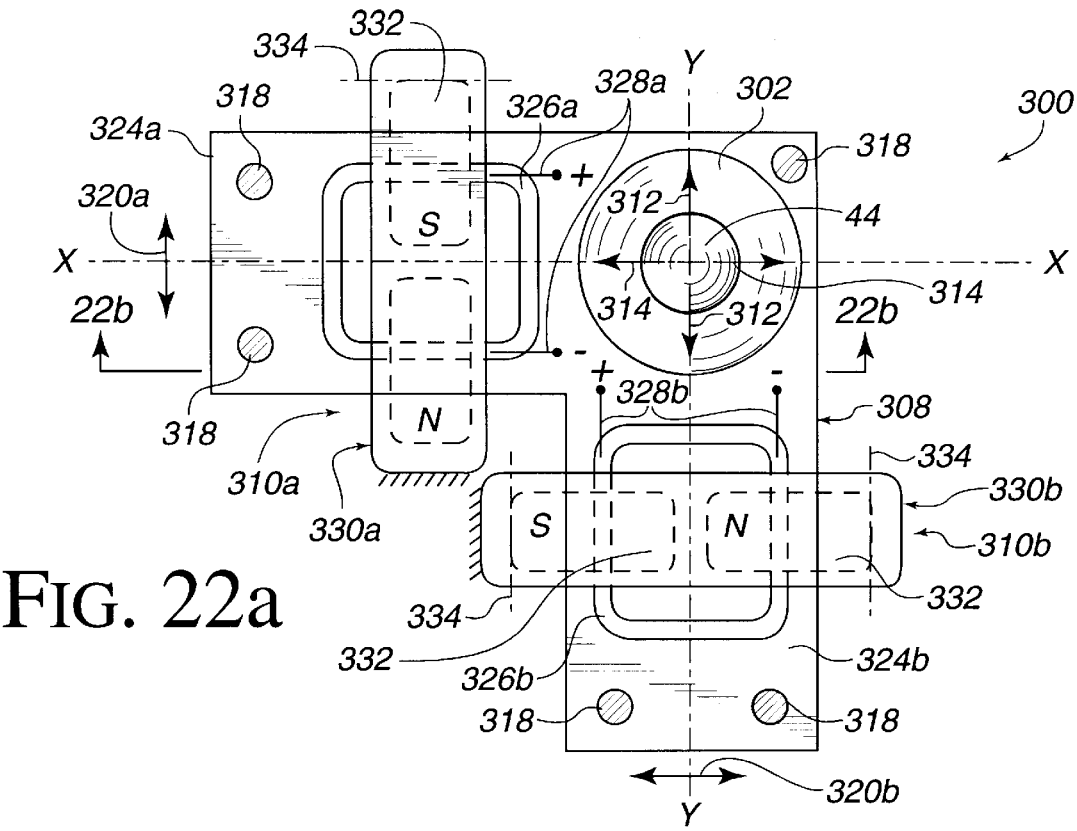
FIG. 22a
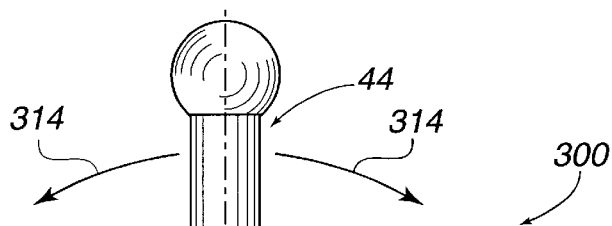
FIG. 22b
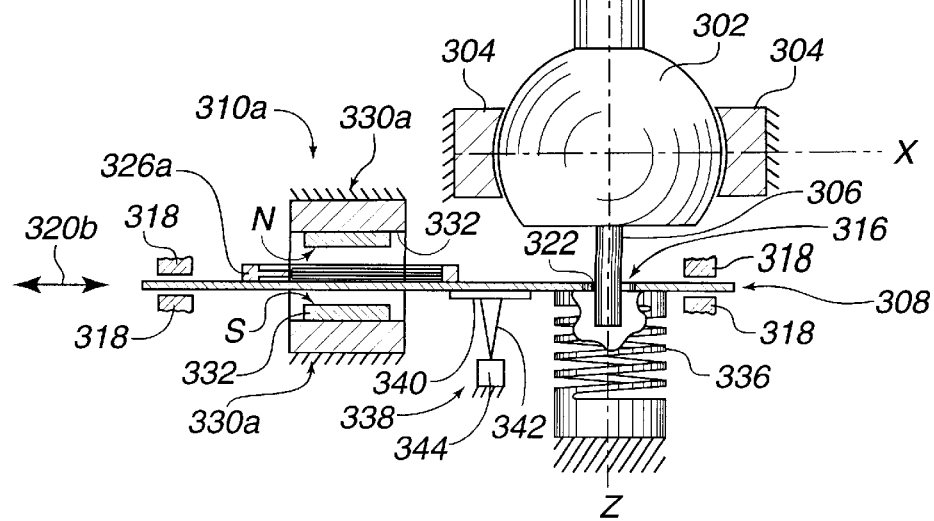

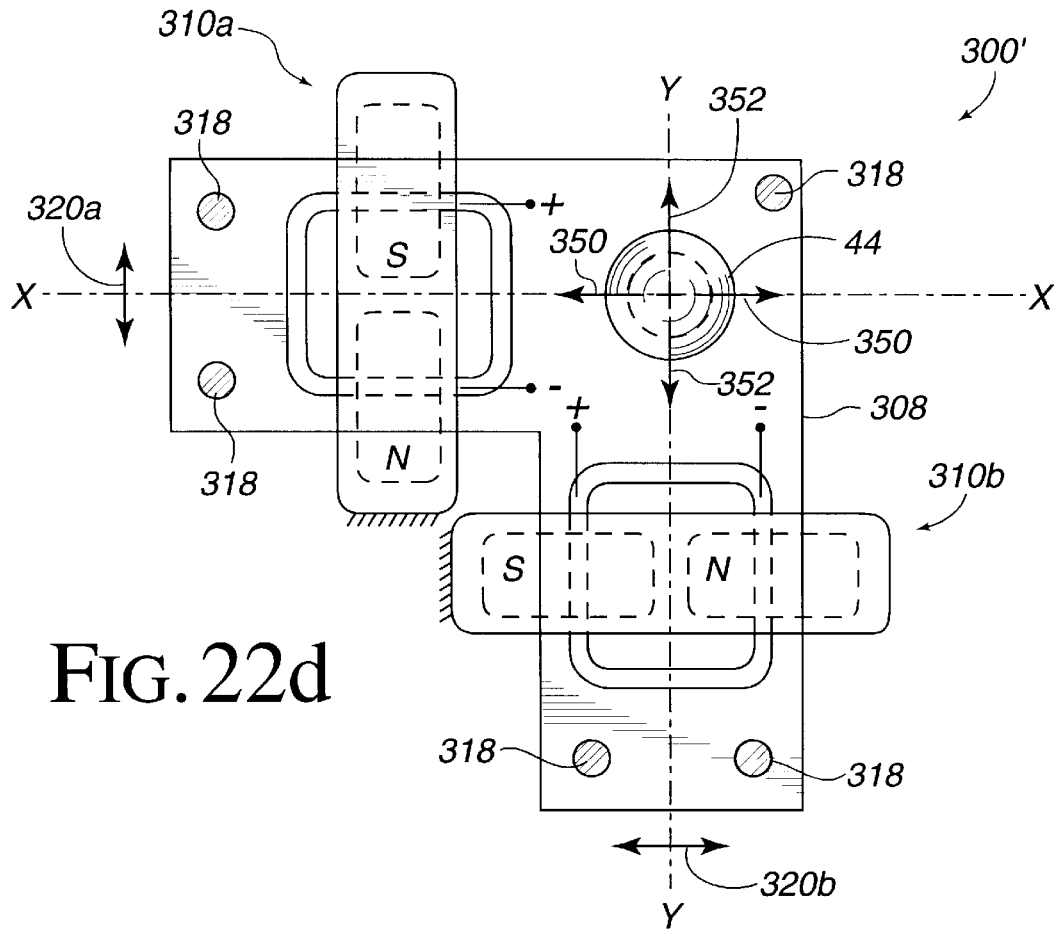
FIG. 22d
FIG. 22e
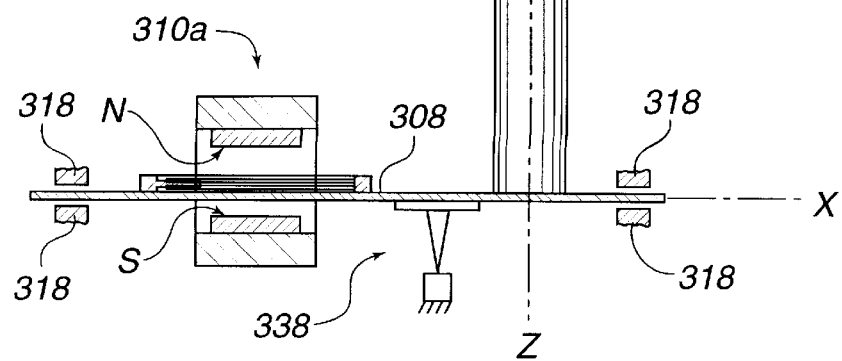

FORCE FEEDBACK INTERFACE DEVICE INCLUDING GROUNDED SENSOR SYSTEM

CROSS REFERENCE TO RELATED APPLICATIONS

This application is a continuation application of prior application Ser. No. 08/560,091 filed on Nov. 17, 1995, now U.S. Pat. No. 5,805,140, which is a continuation-in-part of U.S. patent application Ser. No. 08/374,288 filed Jan. 18, 1995, now U.S. Pat. No. 5,731,804, and a continuation-in-part of U.S. patent application Ser. No. 08/461,170 filed Jun. 5, 1995, now U.S. Pat. No. 5,576,727, which is a continuation of U.S. patent application Ser. No. 08/092,974 filed Jul. 16, 1993, now abandoned, all assigned to the assignee of the present application, and all of which are incorporated herein by reference.

BACKGROUND OF THE INVENTION

The present invention relates generally to interface devices between humans and computers, and more particularly to computer interface devices that provide force feedback to the user.

Virtual reality computer systems provide users with the illusion that they are part of a "virtual" environment. A virtual reality system will typically include a computer processor, such as a personal computer or workstation, specialized virtual reality software, and virtual reality I/O devices such as head mounted displays, sensor gloves, three dimensional ("3D") pointers, etc.

Virtual reality computer systems can be used for training. In many fields, such as aviation and vehicle and systems operation, virtual reality systems have been used successfully to allow a user to learn from and experience a realistic "virtual" environment. The appeal of using virtual reality computer systems for training relates, in part, to the ability of such systems to allow trainees the luxury of confidently operating in a highly realistic environment and making mistakes without "real world" consequences. For example, a virtual reality computer system can allow a doctor-trainee or other human operator or user to "manipulate" a scalpel or probe within a computer-simulated "body", and thereby perform medical procedures on a virtual patient. In this instance, the I/O device which is typically a 3D pointer, stylus, or the like is used to represent a surgical instrument such as a scalpel or probe. As the "scalpel" or "probe" moves within a provided space or structure, results of such movement are updated and displayed in a body image displayed on the screen of the computer system so that the operator can gain the experience of performing such a procedure without practicing on an actual human being or a cadaver. In other applications, virtual reality computer systems allow a user to handle and manipulate the controls of complicated and expensive vehicles and machinery for training and/or entertainment purposes. For example, a pilot or astronaut in training can operate a fighter aircraft or spacecraft by manipulating controls such as a control joystick and other buttons and view the results of controlling the aircraft on a virtual reality simulation of the aircraft in flight. In yet other applications, a user can manipulate objects and tools in the real world, such as a stylus, and view the results of the manipulation in a virtual reality world with a "virtual stylus" viewed on a screen, in 3-D goggles, etc.

For virtual reality systems to provide a realistic (and therefore effective) experience for the user, sensory feedback and manual interaction should be as natural as possible. As virtual reality systems become more powerful and as the number of potential applications increases, there is a growing need for specific human/computer interface devices which allow users to interface with computer simulations with tools that realistically emulate the activities being represented within the virtual simulation. While the state of the art in virtual simulation and medical imaging provides a rich and realistic visual feedback, there is a great need for new human/computer interface tools which allow users to perform natural manual interactions with the computer simulation.

In addition to sensing and tracking a user's manual activity and feeding such information to the controlling computer to provide a 3D visual representation to the user, a human interface mechanism should also provide force or tactile ("haptic") feedback to the user. The need for the user to obtain realistic tactile information and experience tactile sensation is extensive in many kinds of simulation and other applications. For example, in medical/surgical simulations, the "feel" of a probe or scalpel simulator is important as the probe is moved within the simulated body. It would invaluable to a medical trainee to learn how an instrument moves within a body, how much force is required depending on the operation performed, the space available in a body to manipulate an instrument, etc. In simulations of vehicles or equipment, force feedback for controls such as a joystick can be necessary to realistically teach a user the force required to move the joystick when steering in specific situations, such as in a high acceleration environment of an aircraft. In virtual world simulations where the user can manipulate objects, force feedback is necessary to realistically simulate physical objects; for example, if a user touches a pen to a table, the user should feel the impact of the pen on the table. An effective human/computer interface not only acts as an input device for tracking motion, but also as an output device for producing realistic tactile sensations. A "high bandwidth" interface system, which is an interface that accurately responds to signals having fast changes and a broad range of frequencies as well as providing such signals accurately to a control system, is therefore desirable in these and other applications.

In addition, there is a desire to provide force feedback to users of computer systems in the entertainment industry. Joysticks and other interface devices can be used to provide force feedback to a user playing a video game or experiencing a simulation for entertainment purposes. Through such an interface device, a computer system can convey to the user the physical sensation of colliding into a wall, moving through a liquid, driving over a bumpy road, and other sensations. The user can thus experience an entire sensory dimension in the gaming experience that was previously absent. Force feedback interfaces can provide a whole new modality for human-computer interaction.

There are number of devices that are commercially available for interfacing a human with a computer for virtual reality simulations. There are, for example, 2-dimensional input devices such as mice, trackballs, joysticks, and digitizing tablets. However, 2-dimensional input devices tend to be awkward and inadequate to the task of interfacing with 3-dimensional virtual reality simulations. 3-dimensional interface devices are also available. A 3-dimensional human/computer interface tool sold under the trademark Immersion PROBE™ is marketed by Immersion Human Interface Corporation of Santa Clara, Calif., and allows manual control in 3-dimensional virtual reality computer environments. A pen-like stylus allows for dexterous 3-dimensional manipulation in six degrees of freedom, and the position and orientation of the stylus is communicated to a host computer.

The Immersion PROBE, however, does not provide force feedback to a user and thus does not allow a user to experience an entire sensory dimension in virtual reality simulations. Prior art force feedback joysticks provide physical sensations to the user by controlling motors that are coupled to the joystick.

In typical multi-degree of freedom apparatuses that include force feedback, there are several disadvantages. Since actuators which supply force feedback tend to be heavier and larger than sensors, they would provide inertial constraints if added to a device such as the Immersion PROBE. There is also the problem of coupled actuators. In a typical force feedback device, a serial chain of links and actuators is implemented to achieve multiple degrees of freedom in a desired object positioned at the end of the chain, i.e., each actuator is coupled to the previous actuator. The user who manipulates the object must carry the inertia of all of the subsequent actuators and links except for the first actuator in the chain, which is grounded. While it is possible to ground all of the actuators in a serial chain by using a complex transmission of cables or belts, the end result is a low stiffness, high friction, high damping transmission which corrupts the bandwidth of the system, providing the user with an unresponsive and inaccurate interface. These types of interfaces also introduce tactile "noise" to the user through friction and compliance in signal transmission and limit the degree of sensitivity conveyed to the user through the actuators of the device.

Other existing devices provide force feedback to a user. In U.S. Pat. No. 5,184,319, by J. Kramer, an interface is described which provides force and texture information to a user of a computer system. The interface consists of an glove or "exoskeleton" which is worn over the user's appendages, such as fingers, arms, or body. Forces can be applied to the user's appendages using tendon assemblies and actuators controlled by a computer system to simulate force and textual feedback. However, the system described by Kramer is not easily applicable to simulation environments such as those mentioned above where an object is referenced in 3D space and force feedback is applied to the object. The forces applied to the user in Kramer are with reference to the body of the user; the absolute location of the user's appendages are not easily calculated. In addition, the exoskeleton devices of Kramer can be cumbersome or even dangerous to the user if extensive devices are worn over the user's appendages. Furthermore, the devices disclosed in Kramer are complex mechanisms in which many actuators must be used to provide force feedback to the user.

In addition, low-cost and portable mechanical interfaces which can provide force feedback are desirable. For example, personal computers for the home consumer are becoming powerful and fast enough to provide force feedback to the typical mass market consumer. A need is thus arising to be able to manufacture and market force feedback interfaces as cheaply and as efficiently as possible. The cost, complexity, reliability, and size of a force feedback interface for home use should be practical enough to mass produce the devices. In addition, aesthetic concerns such as compactness and operating noise level of a force feedback device are of concern in the home market. Since the prior art feedback interfaces are mainly addressed to specific applications in industry, most force feedback mechanisms are costly, large, heavy, have significant power requirements, are difficult to program for applications. The prior art devices require high speed control signals from a controlling computer for stability, which usually requires more expensive and complex electronics. In addition, the prior art force feedback devices are typically large and noisy. These factors provide many obstacles to the would-be manufacturer of force-feedback interfaces to the home computer market.

Therefore, a less complex, less expensive alternative to a human/computer interface tool having force feedback, lower inertia, higher bandwidth, and less noise is desirable for certain applications.

SUMMARY OF THE INVENTION

The present invention provides a human/computer interface apparatus and method which can provide from one to six degrees of freedom to a user-manipulable object and low cost, highly realistic force feedback to the user of the apparatus. The structure of the apparatus permits transducers to be positioned such that their inertial contribution to the system is very low. A number of the members of the mechanical interface can be manufactured as a single member, providing a low cost interface for a high volume market. In addition, a friction drive mechanism and voice coil actuators provide additional low cost alternatives for the interface.

An interface apparatus and method of the present invention for interfacing the motion of a user-manipulable object with an electrical system includes a user object physically contacted by a user. A gimbal mechanism is coupled to the user object, such as a joystick or a medical tool, and provides at least two degrees of freedom to the user object, where the gimbal mechanism includes multiple members. A selected number of those members are segments formed as a unitary member which provides flex between the selected members. An actuator applies a force along a degree of freedom to the user object in response to electrical signals produced by the electrical system. A sensor detects a position of the user object along the degree of freedom and outputs sensor signals to the electrical system. The actuator and sensor thus provide an electromechanical interface between the user object and the electrical system. An actuator provides force to the user object along each degree of freedom, and the actuators are decoupled from each other.

The gimbal mechanism preferably provides at least two revolute degrees of freedom to the user object about axes of rotation. Alternatively, the gimbal mechanism can provide at least two linear degrees of freedom along linear axes. In a preferred embodiment, the multiple members of the gimbal mechanism are formed as a closed-loop linkage. The linkage can include four members that are flexibly coupled to each other as segments of the unitary member. The four members include first and second extension members and first and second flexible central members, where the central members are each coupled to an extension member and to each other at the user object. A ground member is coupled to a ground surface and is rotatably coupled to the unitary flexible member by bearings. Other embodiments include coupling an object member to the user object and to the central members, and rotating the object member in a third "spin" degree of freedom, where the rotation in the third degree of freedom is allowed by the flexibility of the central members. In yet other embodiments, the ends of the central members are rotatably coupled to the extension members by bearings, and the central members are flexibly coupled to the user object. In another embodiment, the ends of the central members are flexibly coupled to the extension members and the central members are rotatably coupled to the user object by a bearing. In yet another embodiment, a third central member is flexibly coupled between one of the extension members and the user object. A linear axis member can be coupled to the gimbal mechanism to provide the user object with a third linear degree of freedom. A passive damper element can also be coupled to at least one member of the gimbal mechanism to increase dynamic stability of the interface system. Finally, a capstan drive mechanism, including a cable and pully, can used to transmit forces to and from the actuator/sensor and the user with no substantial backlash.

In another preferred embodiment, the interface apparatus interfaces the motion of the user object with the electrical system, which is a host computer. The host computer system can display images to the user on a display screen. A local microprocessor, separate from the host computer and controlled by software instructions, is used to communicate with the host computer via a communication interface by receiving a host command from the host computer. The actuator applies a force to the gimbal mechanism along a degree of freedom to the user object in accordance with a processor command received from the processor. The processor command is derived from the host command. Finally, the sensor detects positions of the user object along a degree of freedom and outputs the sensor signals to the host computer system. The sensor signals include information representative of the position of the user object. Preferably, the sensor is electrically coupled to the processor and outputs the sensor signals to the processor, and the processor sends the sensor signals to the host computer. The processor provides the processor command to the actuator using a processor subroutine selected in accordance with the host command and stored in a memory device. The processor also utilizes the sensor signals to help determine a force output by the actuator. In addition, the processor preferably can use timing information from a clock coupled to the processor to determine the force output by the actuator. The communication interface can include a serial interface which, although relatively slow, may be used to provide accurate force feedback by using the local microprocessor.

In yet another preferred embodiment of an interface apparatus of the present invention, the actuators for applying forces to the user object include voice coil actuators. These actuators apply a current to a wire coil within a magnetic field to produce a force on the coil and a moveable member to which the coil is attached. The produced force has a particular direction depending on the direction of a current flowed through said coil and a magnitude depending on the magnitude of the current. Preferably, an electrical interface is electrically coupled between the voice coil actuators and the electrical system/host computer, and the electrical interface preferably includes a voice coil driver chip for driving the voice coil actuators. The voice coil driver chip preferably has a variable gain of voltage input to current output to provide more realistic and a greater range of forces. In an alternate embodiment, the wire coil includes multiple subcoils that each include a different number of loops. Constant magnitude currents can thus be flowed through selected sub-coils to create different force values on the user object. In addition, the voice coil may includes one coil of wire to apply the force to the user object, and a second coil of wire used as a sensor for sensing a velocity of the user-manipulable object.

In one preferred voice coil actuator interface embodiment, the user object is coupled to a planar member, such as a circuit board. The circuit board is translatable in two degrees of freedom, and this translation causes the user object to move in two user object degrees of freedom. In one embodiment, the user object is coupled to a ball joint that is rotatable in a socket, such that translation of the circuit board causes the ball joint to rotate in the socket and thus causes the user object to pivot in two rotary two degrees of freedom. In another embodiment, the user object is coupled directly to the circuit board and is translated in linear degrees of freedom as the planar member is translated. The coils of wire included in the voice coil actuators can be etched onto the circuit board. In addition, the voice coil driver chips used for driving the voice coil actuators, and other electronic components, can be included on the circuit board.

In another preferred embodiment, the interface apparatus includes a friction drive mechanism coupled between an actuator and a gimbal mechanism of the interface apparatus. Force from the actuator is transmitted to the gimbal mechanism through frictional contact of members of the friction drive mechanism. The friction drive mechanism preferably includes a rotatable drum having a drive bar. A drive roller is coupled to the actuator and frictionally engages the drive bar to rotate the drum and transmit a force to the object in a degree of freedom. Preferably, one or more passive rollers are frictionally engaged with the drive bar on the opposite side of the drive bar to the drive roller, so that a greater compression force is provided between the drive roller and the drive bar. The passive rollers can be spring loaded to the drive roller to provide greater compression force. Preferably, a friction drive mechanism is provided for a second degree of freedom actuator as well. In an alternate embodiment, the friction drive mechanism includes a translatable drum having a drive bar, where the drive roller frictionally engages the drive bar to translate the drum and apply a linear force to the object in a linear degree of freedom.

The interface apparatus of the present invention includes several low cost components that are suitable for providing accurate force feedback for the home market and other markets. The flexible unitary member of the preferred gimbal mechanism can be produced as one part without incurring expenses for bearings and assembly procedures. The embodiments of the present invention including the voice coil actuators utilize readily-available, cheap components that are able to produce realistic forces for the user. The friction drive mechanism of the present invention is able to transmit forces and provide mechanical advantage using low cost parts. These improvements allow a computer system to have more complete and accurate control over a low-cost interface providing realistic force feedback.

These and other advantages of the present invention will become apparent to those skilled in the art upon a reading of the following specification of the invention and a study of the several figures of the drawing.

BRIEF DESCRIPTION OF THE DRAWINGS

FIG. 5 is a perspective detailed view of a capstan drive mechanism used for two degrees of motion in the present invention;

FIG. 5a is a side elevational view of the capstan drive mechanism shown in FIG. 5;

FIG. 5b is a detailed side view of a pulley and cable of the capstan drive mechanism of FIG. 5;

FIG. 6 is a perspective view of a center capstan drive mechanism for a linear axis member of the mechanical apparatus shown in FIG. 3;

FIG. 6a is a cross sectional top view of a pulley and linear axis member used in the capstan drive mechanism of FIG. 6;

FIG. 6b is a cross sectional side view of the linear axis member and transducer shown in FIG. 6;

FIG. 19b is a top plan view of the voice coil actuator of FIG. 19a;

FIGS. 20a–20e are schematic diagrams of an alternate embodiment of the voice coil actuator of FIG. 19a;

FIG. 21b is a side sectional view showing a linear voice coil actuator of FIG. 21a;

FIG. 21c is a perspective view of an alternate embodiment of the interface apparatus of FIG. 21a;

FIG. 22a is a top plan view of an interface apparatus of the present invention having linear voice coil actuators on a circuit board and in which the user object can be moved in rotary degrees of freedom;

FIG. 22b is a side elevational view of the interface apparatus of FIG. 22a;

FIG. 22d is a top plan view of an alternate embodiment of the interface apparatus of FIG. 22a in which the user object can be moved in linear degrees of freedom;

FIG. 22e is a side elevational view of the interface apparatus of FIG. 22c;

DETAILED DESCRIPTION OF PREFERRED EMBODIMENTS

Figure 1:
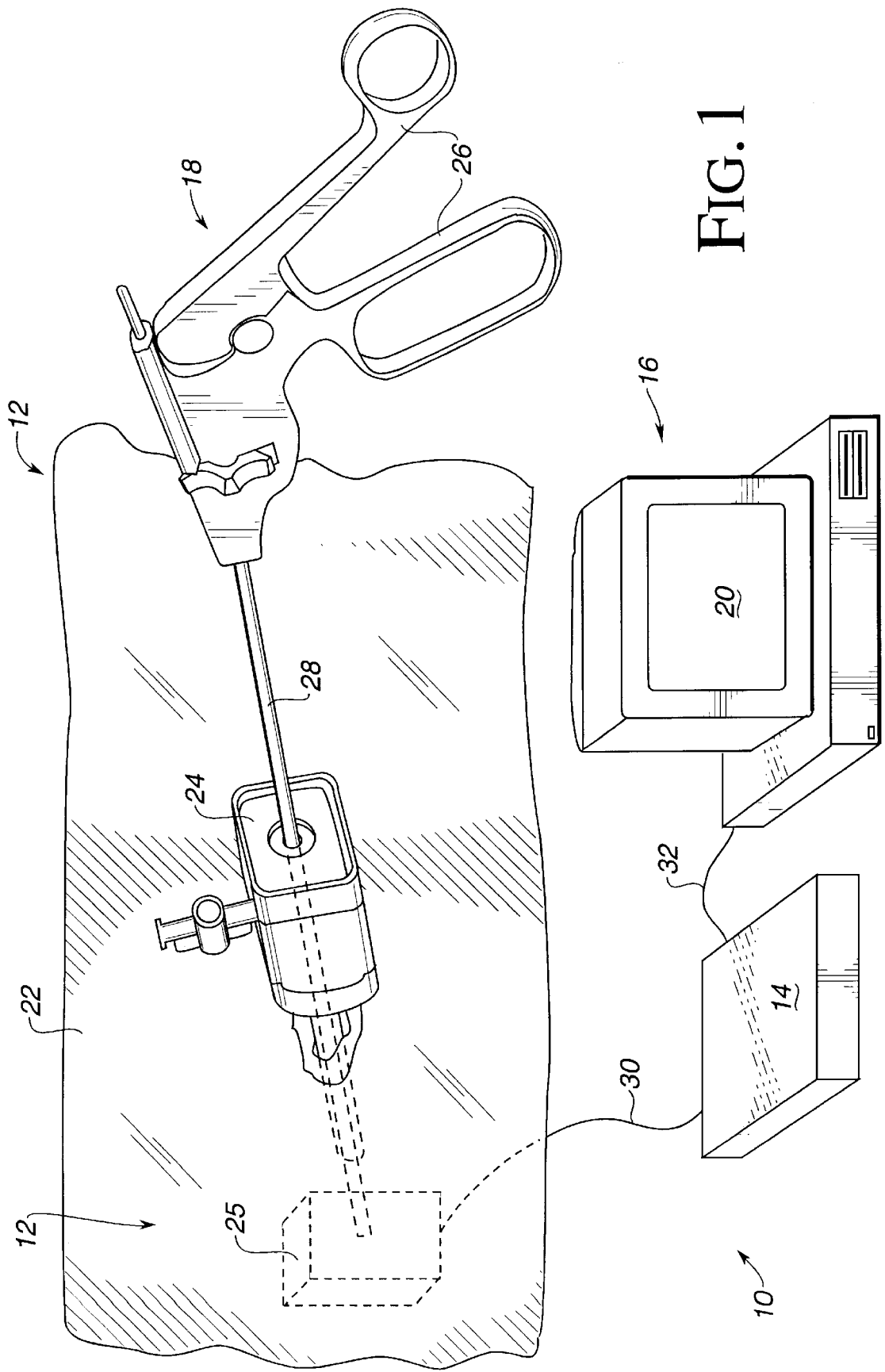
FIG. 1 is a perspective view of a virtual reality system which employs an apparatus of the present invention to interface a laparoscope tool handle with a computer system.

FIG. 1 illustrates an example of the use of the present invention for medical simulation purposes. A virtual reality system 10 used to simulate a medical procedure includes a human/computer interface apparatus 12, an electronic interface 14, and a host computer 16. The illustrated virtual reality system 10 is directed to a virtual reality simulation of a laparoscopic surgery procedure.

The handle 26 of a laparoscopic tool 18 used in conjunction with the present invention is manipulated by an operator and virtual reality images are displayed on a display screen 20 of the digital processing system in response to such manipulations. Display screen 20 can be a standard display screen or CRT, 3-D goggles, or any other visual interface. The digital processing system is typically a host computer 16. Preferably, the host computer is a personal computer or workstation, such as an IBM-PC AT or Macintosh personal computer, or a SUN or Silicon Graphics workstation. For example, the computer 16 can operate under the MS-DOS operating system in conformance with an IBM PC AT standard. Alternatively, host computer system 12 can be one of a variety of home video game systems commonly connected to a television set, such as systems available from Nintendo, Sega, or Sony. In other embodiments, home computer system 12 can be a "set top box" which can be used, for example, to provide interactive television functions to users.

Host computer 16 implements a host application program with which a user is interacting via peripherals and interface device 14. For example, the host application program can be a video game, medical simulation, scientific analysis program, or even an operating system or other application program that utilizes force feedback. Typically, the host application provides images to be displayed on a display output device, as described below, and/or other feedback, such as auditory signals. The medical simulation example of FIG. 1 includes a host medical simulation application program. Such software is commercially available as, for example, Teleos™ from High Techsplanations of Rockville, Md. Suitable software drivers which interface such simulation software with computer input/output (I/O) devices are available from Immersion Human Interface Corporation of Santa Clara, Calif. Alternatively, display screen 20 can display images from a game application program. For example, images describing a point of view from a first-person perspective can be displayed, as in a virtual reality game. Or, images describing a third-person perspective of objects, backgrounds, etc. can be displayed.

One example of a human/interface apparatus 12 as illustrated herein is used to simulate a laparoscopic medical procedure. In addition to the handle of a standard laparoscopic tool 18, the human/interface apparatus 12 may include a barrier 22 and a standard laparoscopic trocar 24 (or a facsimile of a trocar). The barrier 22 is used to represent portion of the skin covering the body of a patient. Trocar 24 is inserted into the body of the virtual patient to provide an entry and removal point from the body of the patient for the laparoscopic tool 18, and to allow the manipulation of the laparoscopic tool. Laparoscopic tools and trocars 24 are commercially available from sources such as U.S. Surgical of Connecticut. Barrier 22 and trocar 24 can be omitted from apparatus 12 in other embodiments. Preferably, the laparoscopic tool 18 is modified; in the preferred embodiment, the shaft is replaced by a linear axis member of the present invention, as described below. In other embodiments, the end of the shaft of the tool (such as any cutting edges) can be removed. The end of the laparoscopic tool 18 is not required for the virtual reality simulation, and is removed to prevent any potential damage to persons or property.

The laparoscopic tool 18 includes a handle or "grip" portion 26 and a shaft portion 28. The shaft portion is an elongated mechanical object and, in particular, is an elongated cylindrical object, described in greater detail below. In one embodiment, the present invention is concerned with tracking the movement of the shaft portion 28 in three-dimensional space, where the movement has been constrained such that the shaft portion 28 has only three or four free degrees of motion. This is a good simulation of the real use of a laparoscopic tool 18 in that once it is inserted into a trocar 24 and through the mechanical apparatus 25, it is limited to about four degrees of freedom. More particularly, the shaft 28 is constrained at some point of along its length such that it can move with four degrees of freedom within the patient's body.

A mechanical apparatus 25 for interfacing mechanical input and output is shown within the "body" of the patient in phantom lines. When a surface is generated on the computer screen, the computer will send feedback signals to the tool 18 and mechanical apparatus 25, which has actuators for generating forces in response to the position of a virtual laparoscopic tool relative to the surface depicted on the computer screen. Force is applied for example, by powering the actuators appropriate to the images portrayed on the screen. Mechanical apparatus 25 is shown in greater detail with respect to FIGS. 2 and 12.

While one embodiment of the present invention will be discussed with reference to the laparoscopic tool 18, it will be appreciated that a great number of other types of objects can be used with the method and apparatus of the present invention. In fact, the present invention can be used with any mechanical object where it is desirable to provide a human/computer interface with one to six degrees of freedom. Such objects may include endoscopic or other similar surgical tools used in medical procedures, catheters, hypodermic needles, wires, fiber optic bundles, styluses, joysticks, screw drivers, pool cues, etc. Some of these other objects are described in detail subsequently.

The electronic interface 14 is a component of the human/computer interface apparatus 12 and may couple the apparatus 12 to the host computer 16. Electronic interface 14 can be included within a housing of mechanical apparatus 25 or be provided as a separate unit, as shown in FIG. 1. More particularly, interface 14 is used in preferred embodiments to couple the various actuators and sensors of apparatus 25 (described in detail below) to computer 16. One suitable embodiment of interface 14 is described in detail with reference to FIG. 9, in which the interface can include a dedicated interface card to be plugged into computer 16. A different embodiment 14' of interface 14 is described in detail with respect to FIG. 20, in which the interface includes a microprocessor local to the apparatus 12 and can be coupled to computer 16 through a slower, serial interface or a parallel interface.

The electronic interface 14 can be coupled to mechanical apparatus 25 of the apparatus 12 by a cable 30 (or may be included within the housing of apparatus 12) and is coupled to the computer 16 by a cable 32 (or may be directly connected to the computer using a interface card). In other embodiments, signals can be sent to and from interface 14 and computer 16 by wireless transmission and reception. In some embodiments of the present invention, interface 14 serves solely as an input device for the computer 16. In other embodiments of the present invention, interface 14 serves solely as an output device for the computer 16. In preferred embodiments of the present invention, the interface 14 serves as an input/output (I/O) device for the computer 16. The interface 14 can also receive inputs from other input devices or controls that are associated with apparatus 12 and can relay those inputs to computer 16. For example, commands sent by the user activating a button on apparatus 12 can be relayed to computer 16 to implement a command or cause the computer 16 to output a command to the apparatus 12. Such input devices are described in greater detail with respect to FIG. 24.

Figure 2:
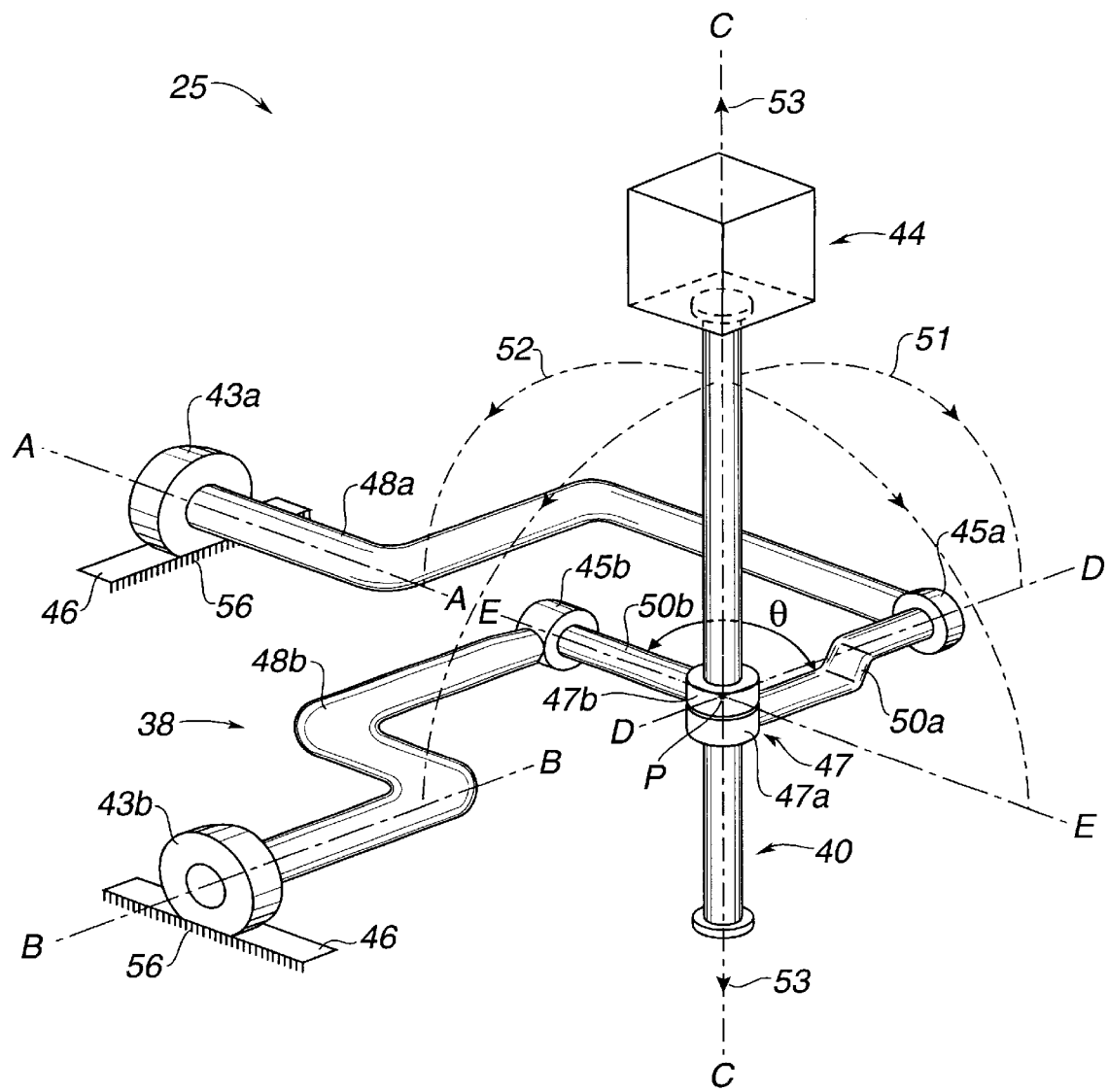
FIG. 2 is a perspective view of a mechanical apparatus of the present invention for providing mechanical input and output to a computer system.

In FIG. 2, a perspective view of mechanical apparatus 25 for providing mechanical input and output in accordance with the present invention is shown. Apparatus 25 includes a gimbal mechanism 38 and a linear axis member 40. A user object 44 is preferably coupled to linear axis member 40.

Gimbal mechanism 38, in the described embodiment, provides support for apparatus 25 on a grounded surface 56 (schematically shown as part of member 46). Gimbal mechanism 38 is preferably a five-member linkage that includes a ground member 46, extension members 48a and 48b, and central members 50a and 50b. Ground member 46 is coupled to a base or surface which provides stability for apparatus 25. Ground member 46 is shown in FIG. 2 as two separate members coupled together through grounded surface 56. The members of gimbal mechanism 38 are rotatably coupled to one another through the use of rotatable bearings or pivots, wherein extension member 48a is rotatably coupled to ground member 46 by bearing 43a and can rotate about an axis A, central member 50a is rotatably coupled to extension member 48a by bearing 45a and can rotate about a floating axis D, extension member 48b is rotatably coupled to ground member 46 by bearing 43b and can rotate about axis B, central member 50b is rotatably coupled to extension member 48b by bearing 45b and can rotate about floating axis E, and central member 50a is rotatably coupled to central member 50b by bearing 47 at a center point P at the intersection of axes D and E. Preferably, central member 50a is coupled to one rotatable portion 47a of bearing 47, and central member 50b is coupled to the other rotatable portion 47b of bearing 47. The axes D and E are "floating" in the sense that they are not fixed in one position as are axes A and B. Axes A and B are substantially mutually perpendicular. As used herein, "substantially perpendicular" will mean that two objects or axis are exactly or almost perpendicular, i.e. at least within five degrees or ten degrees of perpendicular, or more preferably within less than one degree of perpendicular. Similarly, the term "substantially parallel" will mean that two objects or axis are exactly or almost parallel, i.e. are at least within five or ten degrees of parallel, and are preferably within less than one degree of parallel.

Gimbal mechanism 38 is formed as a five member closed chain. Each end of one member is coupled to the end of a another member. The five-member linkage is arranged such that extension member 48a, central member 50a, and central member 50b can be rotated about axis A in a first degree of freedom. The linkage is also arranged such that extension member 48b, central member 50b, and central member 50a can be rotated about axis B in a second degree of freedom.

When object 44 is positioned at the "origin" as shown in FIG. 2, an angle θ between the central members 50a and 50b is about 90 degrees. When object 44 is rotated about one or both axes A and B, central members move in two fashions: rotation about axis D or E by bearing 45b and/or 45a, and rotation about axis C by bearing 47 such that angle θ changes. For example, if the object 44 is moved into the page of FIG. 2 away from the viewer, or out of the plane of the page toward the viewer, then the angle θ will decrease. If the object is moved to the left or right as shown in FIG. 2, the angle θ will increase.

Linear axis member 40 is preferably an elongated rod-like member which is coupled to central member 50a and central member 50b at the point of intersection P of axes A and B. As shown in FIG. 1, linear axis member 40 can be used as shaft 28 of user object 44. In other embodiments, linear axis member 40 is coupled to a different object. Linear axis member 40 is coupled to gimbal mechanism 38 such that it extends out of the plane defined by axis A and axis B. Linear axis member 40 can be rotated about axis A by rotating extension member 48a, central member 50a, and central member 50b in a first revolute degree of freedom, shown as arrow line 51. Member 40 can also be rotated about axis B by rotating extension member 50b and the two central members about axis B in a second revolute degree of freedom, shown by arrow line 52. Being also translatably coupled to the ends of central members 50a and 50b, linear axis member 40 can be linearly translated, independently with respect to the gimbal mechanism 38, along floating axis C, providing a third degree of freedom as shown by arrows 53. Axis C can, of course, be rotated about one or both axes A and B as member 40 is rotated about these axes.

Also preferably coupled to gimbal mechanism 38 and linear axis member 40 are transducers, such as sensors and actuators. Such transducers are preferably coupled at the link points between members of the apparatus and provide input to and output from an electrical system, such as computer 16. Transducers that can be used with the present invention are described in greater detail with respect to FIG. 3.

User object 44 is coupled to apparatus 25 and is preferably an interface object for a user to grasp or otherwise manipulate in three dimensional (3D) space. One example of a user object 44 is the grip 26 of a laparoscopic tool 18, as shown in FIG. 1. Shaft 28 of tool 18 can be implemented as part of linear axis member 40. Other examples described in subsequent embodiments include a stylus and joystick. User object 44 may be moved in all three degrees of freedom provided by gimbal mechanism 38 and linear axis member 40 and additional degrees of freedom as described below. As user object 44 is moved about axis A, floating axis D varies its position, and as user object 44 is moved about axis B, floating axis E varies its position. The floating axes E and D are coincident with the fixed axes A and B, respectively, when the user object is in a center position as shown in FIG. 2.

Figure 3:
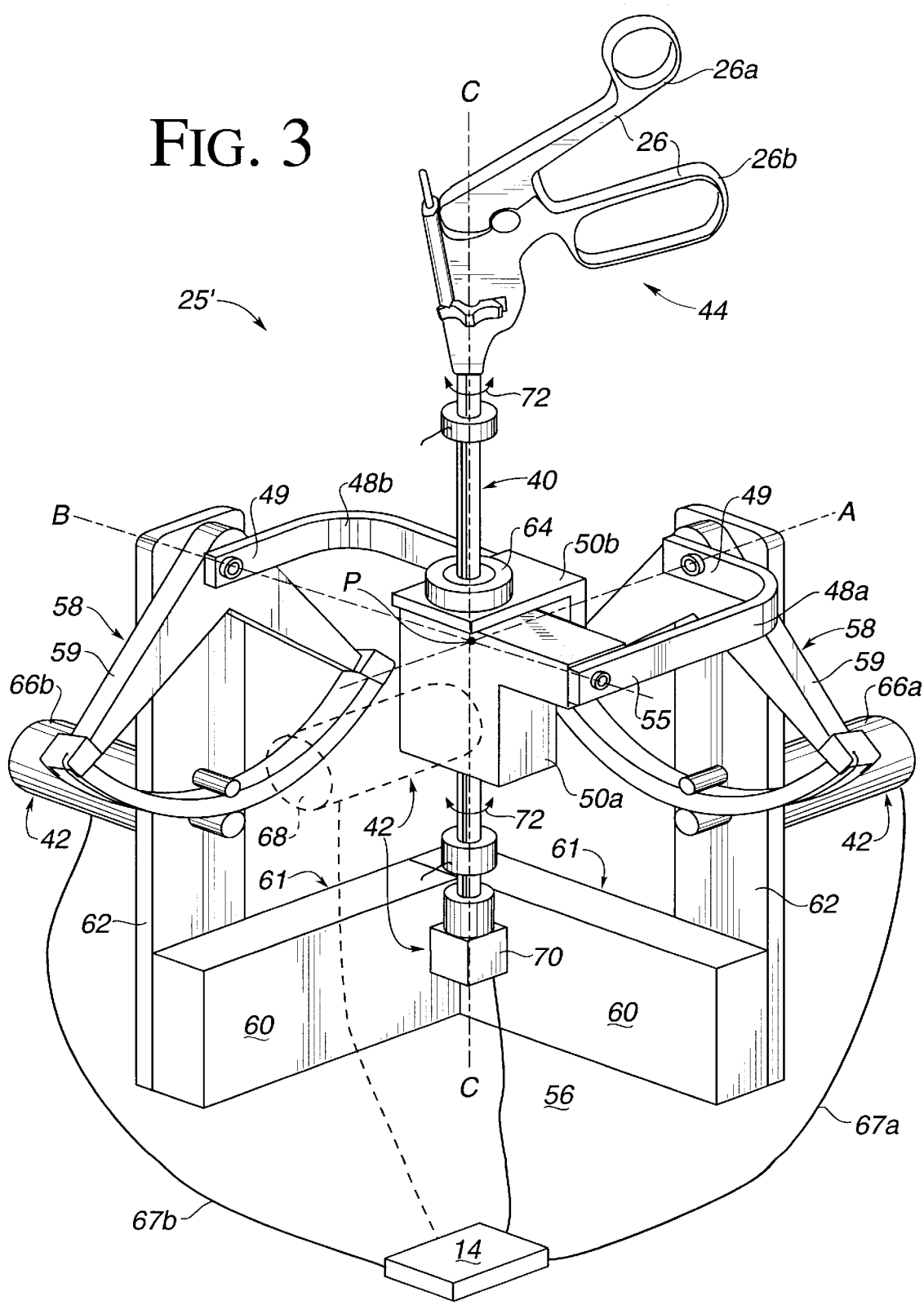
FIG. 3 is a perspective front view of a preferred embodiment of the mechanical apparatus of FIG. 2.
Figure 4:
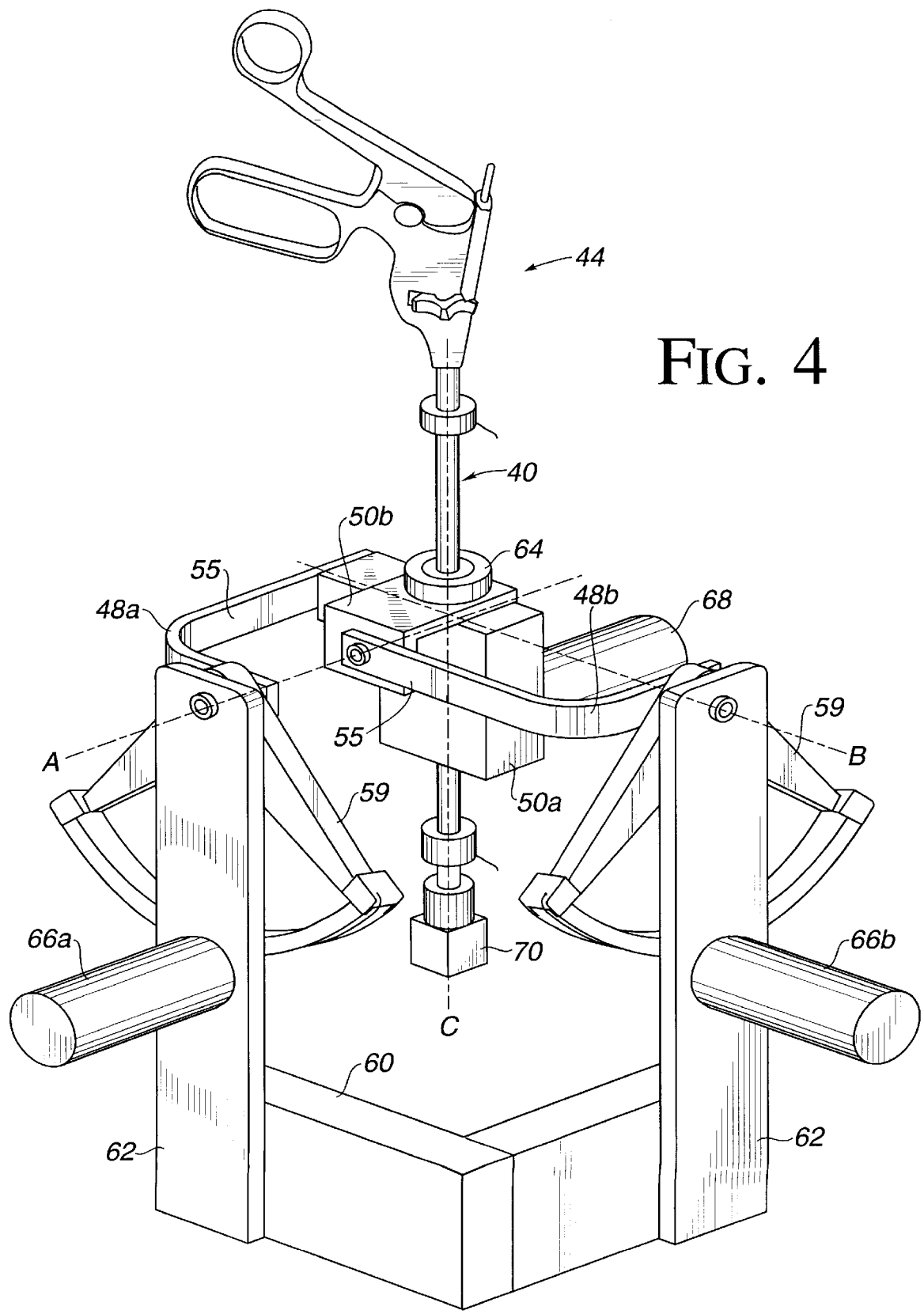
FIG. 4 is a perspective rear view of the embodiment of the mechanical apparatus of FIG. 3.

FIGS. 3 and 4 are perspective views of a specific embodiment of a mechanical apparatus 25' for providing mechanical input and output to a computer system in accordance with the present invention. FIG. 3 shows a front view of apparatus 25', and FIG. 4 shows a rear view of the apparatus. Apparatus 25' includes a gimbal mechanism 38, a linear axis member 40, and transducers 42. A user object 44, shown in this embodiment as a laparoscopic instrument having a grip portion 26, is coupled to apparatus 25'. Apparatus 25' operates in substantially the same fashion as apparatus 25 described with reference to FIG. 2.

Gimbal mechanism 38 provides support for apparatus 25' on a grounded surface 56, such as a table top or similar surface. The members and joints ("bearings") of gimbal mechanism 38 are preferably made of a lightweight, rigid, stiff metal, such as aluminum, but can also be made of other rigid materials such as other metals, plastic, etc. Gimbal mechanism 38 includes a ground member 46, capstan drive mechanisms 58, extension members 48a and 48b, central drive member 50a, and central link member 50b. Ground member 46 includes a base member 60 and vertical support members 62. Base member 60 is coupled to grounded surface 56 and provides two outer vertical surfaces 61 which are in a substantially perpendicular relation which each other. A vertical support member 62 is coupled to each of these outer surfaces of base member 60 such that vertical members 62 are in a similar substantially 90-degree relation with each other.

A capstan drive mechanism 58 is preferably coupled to each vertical member 62. Capstan drive mechanisms 58 are included in gimbal mechanism 38 to provide mechanical advantage without introducing friction and backlash to the system. A capstan drum 59 of each capstan drive mechanism is rotatably coupled to a corresponding vertical support member 62 to form axes of rotation A and B, which correspond to axes A and B as shown in FIG. 1. The capstan drive mechanisms 58 are described in greater detail with respect to FIG. 5.

Extension member 48a is rigidly coupled to capstan drum 59 and is rotated about axis A as capstan drum 59 is rotated. Likewise, extension member 48b is rigidly coupled to the other capstan drum 59 and can be rotated about axis B. Both extension members 48a and 48b are formed into a substantially 90-degree angle with a short end 49 coupled to capstan drum 59. Central drive member 50a is rotatably coupled to a long end 55 of extension member 48a and extends at a substantially parallel relation with axis B. Similarly, central link member 50b is rotatably coupled to the long end of extension member 48b and extends at a substantially parallel relation to axis A (as better viewed in FIG. 4). Central drive member 50a and central link member 50b are rotatably coupled to each other at the center of rotation of the gimbal mechanism, which is the point of intersection P of axes A and B. Bearing 64 connects the two central members 50a and 50b together at the intersection point P.

Gimbal mechanism 38 provides two degrees of freedom to an object positioned at or coupled to the center point P of rotation. An object at or coupled to point P can be rotated about axis A and B or have a combination of rotational movement about these axes.

Linear axis member 40 is a cylindrical member that is preferably coupled to central members 50a and 50b at intersection point P. In alternate embodiments, linear axis member 40 can be a non-cylindrical member having a cross-section of, for example, a square or other polygon. Member 40 is positioned through the center of bearing 64 and through holes in the central members 50a and 50b. The linear axis member can be linearly translated along axis C, providing a third degree of freedom to user object 44 coupled to the linear axis member. Linear axis member 40 can preferably be translated by a transducer 42 using a capstan drive mechanism similar to capstan drive mechanism 58. The translation of linear axis member 40 is described in greater detail with respect to FIG. 6.

Transducers 42 are preferably coupled to gimbal mechanism 38 to provide input and output signals between mechanical apparatus 25' and computer 16. In the described embodiment, transducers 42 include two grounded transducers 66a and 66b, central transducer 68, and shaft transducer 70. The housing of grounded transducer 66a is preferably coupled to vertical support member 62 and preferably includes both an actuator for providing force in or otherwise influencing the first revolute degree of freedom about axis A and a sensor for measuring the position of object 44 in or otherwise influenced by the first degree of freedom about axis A, i.e., the transducer 66a is "associated with" or "related to" the first degree of freedom. A rotational shaft of actuator 66a is coupled to a pulley of capstan drive mechanism 58 to transmit input and output along the first degree of freedom. The capstan drive mechanism 58 is described in greater detail with respect to FIG. 5. Grounded transducer 66b preferably corresponds to grounded transducer 66a in function and operation. Transducer 66b is coupled to the other vertical support member 62 and is an actuator/sensor which influences or is influenced by the second revolute degree of freedom about axis B.

Grounded transducers 66a and 66b are preferably bi-directional transducers which include sensors and actuators. The sensors are preferably relative optical encoders which provide signals to measure the angular rotation of a shaft of the transducer. The electrical outputs of the encoders are routed to computer interface 14 via buses 67a and 67b and are detailed with reference to FIG. 9. Other types of sensors can also be used, such as potentiometers, etc. In addition, it is also possible to use non-contact sensors at different positions relative to mechanical apparatus 25. For example, a Polhemus (magnetic) sensor can detect magnetic fields from objects; or, an optical sensor such as lateral effect photo diode includes a emitter/detector pair that detects positions of the emitter with respect to the detector in one or more degrees of freedom; for example, a photo diode by Hamamatsu Co., part S1743, can be used. These types of sensors are able to detect the position of object 44 in particular degrees of freedom without having to be coupled to a joint of the mechanical apparatus. Alternatively, sensors can be positioned at other locations of relative motion or joints of mechanical apparatus 25.

It should be noted that the present invention can utilize both absolute and relative sensors. An absolute sensor is one which the angle of the sensor is known in absolute terms, such as with an analog potentiometer. Relative sensors only provide relative angle information, and thus require some form of calibration step which provide a reference position for the relative angle information. The sensors described herein are primarily relative sensors. In consequence, there is an implied calibration step after system power-up wherein the sensor's shaft is placed in a known position within the apparatus 25' and a calibration signal is provided to the system to provide the reference position mentioned above. All angles provided by the sensors are thereafter relative to that reference position. Such calibration methods are well known to those skilled in the art and, therefore, will not be discussed in any great detail herein.

Transducers 66a and 66b also preferably include actuators. These actuators can be of two types: active actuators and passive actuators. Active actuators include linear current control motors, stepper motors, pneumatic/hydraulic active actuators, and other types of actuators that transmit a force to move an object. For example, active actuators can drive a rotational shaft about an axis in a rotary degree of freedom, or drive a linear shaft along a linear degree of freedom. Active transducers of the present invention are preferably bidirectional, meaning they can selectively transmit force along either direction of a degree of freedom. For example, DC servo motors can receive force control signals to control the direction and torque (force output) that is produced on a shaft. In the described embodiment, active linear current control motors, such as DC servo motors, are used. The control signals for the motor are produced by computer interface 14 on control buses 67a and 67b and are detailed with respect to FIG. 9. The motors may include brakes which allow the rotation of the shaft to be halted in a short span of time. Also, the sensors and actuators in transducers 42 can be included together as a sensor/actuator pair transducers. A suitable transducer for the present invention including both an optical encoder and current controlled motor is a 20 W basket wound servo motor manufactured by Maxon.

In alternate embodiments, other types of active motors can also be used, such as a stepper motor, brushless DC motors, pneumatic/hydraulic actuators, a torquer (motor with limited angular range), or a voice coil, which are well known to those skilled in the art. Voice coils are described in greater detail with respect to FIG. 18. Stepper motors and the like are not as well suited because stepper motor control involves the use of steps or pulses which can be felt as pulsations by the user, thus corrupting the virtual simulation. The present invention is better suited to the use of linear current controlled motors, which do not have this noise.

Passive actuators can also be used in transducers 66a, 66b, and 68. Magnetic particle brakes, friction brakes, or pneumatic/hydraulic passive actuators can be used in addition to or instead of a motor to generate a damping resistance or friction in a degree of motion. An alternate preferred embodiment only including passive actuators may not be as realistic as an embodiment including motors; however, the passive actuators are typically safer for a user since the user does not have to fight generated forces. Passive actuators typically can only provide bidirectional resistance to a degree of motion. A suitable magnetic particle brake for interface device 14 is available from Force Limited, Inc. of Santa Monica, Calif.

In other embodiments, all or some of transducers 42 can include only sensors to provide an apparatus without force feedback along designated degrees of freedom. Similarly, all or some of transducers 42 can be implemented as actuators without sensors to provide only force feedback.

In addition, in some embodiments, passive (or "viscous") damper elements can be provided on the bearings of apparatus 25 to remove energy from the system and intentionally increase the dynamic stability of the mechanical system. This may have the side effect of degrading the bandwidth of the system; however, if other factors such as the speed of processor 410 (see FIG. 24), rate of actuator control, and position sensing resolution already degrade the bandwidth, then such dampers may be acceptable. For example, inexpensive plastic dampers, such as rotational dampers produced by Fastex/Deltar, can be placed at desired bearing positions and have one end grounded. In other embodiments, this passive damping can be introduced by using the back electromotive force (EMF) of the actuators 42 to remove energy from the system. This can also be accomplished by using a shunt resistor coupled across the terminals of a motor or the coils of a voice coil actuator. Also, passive brakes, as mentioned above, can be used. In addition, in the voice coil embodiments (see FIGS. 18–22), multiple wire coils can be provided, where some of the coils can be used to provide back EMF and damping forces.

Central transducer 68 is coupled to central drive member 50a and preferably includes an actuator for providing force in the linear third degree of freedom along axis C and a sensor for measuring the position of object 44 along the third degree of freedom. The rotational shaft of central transducer 68 is coupled to a translation interface coupled to central drive member 50a which is described in greater detail with respect to FIG. 6. In the described embodiment, central transducer 68 is an optical encoder and DC servo motor combination similar to the actuators 66a and 66b described above.

The transducers 66a, 66b and 68 of the described embodiment are advantageously positioned to provide a very low amount of inertia to the user handling object 44. Transducer 66a and transducer 66b are decoupled, meaning that the transducers are both directly coupled to ground member 46 which is coupled to ground surface 56, i.e. the ground surface carries the weight of the transducers, not the user handling object 44. The weights and inertia of the transducers 66a and 66b are thus substantially negligible to a user handling and moving object 44. This provides a more realistic interface to a virtual reality system, since the computer can control the transducers to provide substantially all of the forces felt by the user in these degrees of motion. Apparatus 25' is a high bandwidth force feedback system, meaning that high frequency signals can be used to control transducers 42 and these high frequency signals will be applied to the user object with high precision, accuracy, and dependability. The user feels very little compliance or "mushiness" when handling object 44 due to the high bandwidth. In contrast, in typical prior art arrangements of multi-degree of freedom interfaces, one actuator "rides" upon another actuator in a serial chain of links and actuators. This low bandwidth arrangement causes the user to feel the inertia of coupled actuators when manipulating an object.

Central transducer 68 is positioned near the center of rotation of two revolute degrees of freedom. Though the transducer 68 is not grounded, its central position permits a minimal inertial contribution to the mechanical apparatus 25' along the provided degrees of freedom. A user manipulating object 44 thus will feel minimal internal effects from the weight of transducers 66a, 66b and 68.

Shaft transducer 70 preferably includes a sensor and is provided in the described embodiment to measure a fourth degree of freedom for object 44. Shaft transducer 70 is preferably positioned at the end of linear axis member 40 that is opposite to the object 44 and measures the rotational position of object 44 about axis C in the fourth degree of freedom, as indicated by arrow 72. Shaft transducer 70 is described in greater detail with respect to FIG. 6 and 6b. Preferably, shaft transducer 72 is implemented using an optical encoder similar to the encoders described above. A suitable input transducer for use in the present invention is an optical encoder model SI marketed by U.S. Digital of Vancouver, Wash. In the described embodiment, shaft transducer 70 only includes a sensor and not an actuator. This is because for typical medical procedures, which is one intended application for the embodiment shown in FIGS. 3 and 4, rotational force feedback to a user about axis C is typically not required to simulate actual operating conditions. However, in alternate embodiments, an actuator such as a motor can be included in shaft transducer 70 similar to transducers 66a, 66b, and 68.

Object 44 is shown in FIGS. 3 and 4 as a grip portion 26 of a laparoscopic tool similar to the tool shown in FIG. 1. Shaft portion 28 is implemented as linear axis member 40. A user can move the laparoscopic tool about axes A and B, and can translate the tool along axis C and rotate the tool about axis C. The movements in these four degrees of freedom will be sensed and tracked by computer system 16. Forces can be applied preferably in the first three degrees of freedom by the computer system to simulate the tool impacting a portion of subject body, experiencing resistance moving through tissues, etc.

Optionally, additional transducers can be added to apparatus 25' to provide additional degrees of freedom for object 44. For example, a transducer can be added to grip 26 of laparoscopic tool 18 to sense when the user moves the two portions 26a and 26b relative to each other to simulate extending the cutting blade of the tool. Such a laparoscopic tool sensor is described in U.S. Pat. No. 5,623,582, filed Jul. 14, 1994 and entitled "Method and Apparatus for Providing Mechanical I/O for Computer Systems" assigned to the assignee of the present invention and incorporated herein by reference in its entirety.

FIG. 5 is a perspective view of a capstan drive mechanism 58 shown in some detail. As an example, the drive mechanism 58 coupled to extension arm 48b is shown; the other capstan drive 58 coupled to extension arm 48a is substantially similar to the mechanism presented here. Capstan drive mechanism 58 includes capstan drum 59, capstan pulley 76, and stop 78. Capstan drum 59 is preferably a wedge-shaped member having leg portion 82 and a curved portion 84. Other shapes of member 59 can also be used. Leg portion 82 is pivotally coupled to vertical support member 62 at axis B (or axis A for the opposing capstan drive mechanism). Extension member 48b is rigidly coupled to leg portion 82 such that when capstan drum 59 is rotated about axis B, extension member 48b is also rotated and maintains the position relative to leg portion 82 as shown in FIG. 5. Curved portion 84 couples the two ends of leg portion 82 together and is preferably formed in an arc centered about axis B. Curved portion 84 is preferably positioned such that its bottom edge 86 is about 0.030 inches above pulley 76.

Cable 80 is preferably a thin metal cable connected to curved portion 84 of the capstan drum. Other types of durable cables, cords, wire, etc. can be used as well. Cable 80 is attached at a first end to curved portion 84 near an end of leg portion 82 and is drawn tautly against the outer surface 86 of curved portion 84. Cable 80 is wrapped around pulley 76 a number of times and is then again drawn tautly against outer surface 86. The second end of cable 80 is firmly attached to the other end of curved portion 84 near the opposite leg of leg portion 82. The cable transmits rotational force from pulley 76 to the capstan drum 59, causing capstan drum 59 to rotate about axis B as explained below. The cable also transmits rotational force from drum 59 to the pulley and transducer 66b. The tension in cable 80 should be at a level so that negligible backlash or play occurs between capstan drum 59 and pulley 76. Preferably, the tension of cable 80 can be adjusted by pulling more (or less) cable length through an end of curved portion 84. Caps 81 on the ends of curved portion 84 can be used to easily tighten cable 80. Each cap 81 is preferably tightly coupled to cable 80 and includes a pivot and tightening screw which allow the cap to move in a direction indicated by arrow 83 to tighten cable 80.

Capstan pulley 76 is a threaded metal cylinder which transfers rotational force from transducer 66b to capstan drum 59 and from capstan drum 59 to transducer 66b. Pulley 76 is rotationally coupled to vertical support member 62 by a shaft 88 (shown in FIG. 5a) positioned through a bore of vertical member 62 and rigidly attached to pulley 76. Transducer 66b is coupled to pulley 76 by shaft 88 through vertical support member 62. Rotational force is applied from transducer 66b to pulley 76 when the actuator of transducer 66b rotates the shaft. The pulley, in turn, transmits the rotational force to cable 80 and thus forces capstan drum 59 to rotate in a direction about axis B. Extension member 48b rotates with capstan drum 59, thus causing force along the second degree of freedom for object 44. Note that pulley 76, capstan drum 59 and extension member 48b will only actually rotate if the user is not applying the same amount or a greater amount of rotational force to object 44 in the opposite direction to cancel the rotational movement. In any event, the user will feel the rotational force along the second degree of freedom in object 44 as force feedback.

The capstan mechanism 58 provides a mechanical advantage to apparatus 25' so that the force output of the actuators can be increased. The ratio of the diameter of pulley 76 to the diameter of capstan drum 59 (i.e. double the distance from axis B to the bottom edge 86 of capstan drum 59) dictates the amount of mechanical advantage, similar to a gear system. In the preferred embodiment, the ratio of drum to pulley is equal to 15:1, although other ratios can be used in other embodiments.

Similarly, when the user moves object 44 in the second degree of freedom, extension member 48b rotates about axis B and rotates capstan drum 59 about axis B as well. This movement causes cable 80 to move, which transmits the rotational force to pulley 76. Pulley 76 rotates and causes shaft 88 to rotate, and the direction and magnitude of the movement is detected by the sensor of transducer 66b. A similar process occurs along the first degree of freedom for the other capstan drive mechanism 58. As described above with respect to the actuators, the capstan drive mechanism provides a mechanical advantage to amplify the sensor resolution by a ratio of drum 59 to pulley 76 (15:1 in the preferred embodiment).

Stop 78 is rigidly coupled to vertical support member 62 a few millimeters above curved portion 84 of capstan drum 59. Stop 78 is used to prevent capstan drum 59 from moving beyond a designated angular limit. Thus, drum 59 is constrained to movement within a range defined by the arc length between the ends of leg portion 82. This constrained movement, in turn, constrains the movement of object 44 in the first two degrees of freedom. In the described embodiment, stop 78 is a cylindrical member inserted into a threaded bore in vertical support member 62.

FIG. 5a is a side elevational view of capstan mechanism 58 as shown in FIG. 5. Cable 80 is shown routed along the bottom side 86 of curved portion 84 of capstan drum 59. Cable 80 is preferably wrapped around pulley 76 so that the cable is positioned between threads 90, i.e., the cable is guided by the threads as shown in greater detail in FIG. 5b. As pulley 76 is rotated by transducer 66b or by the manipulations of the user, the portion of cable 80 wrapped around the pulley travels closer to or further from vertical support member 62, depending on the direction that pulley 76 rotates. For example, if pulley 76 is rotated counterclockwise (when viewing the pulley as in FIG. 5), then cable 80 moves toward vertical support member 62 as shown by arrow 92. Capstan drum 59 also rotates clockwise as shown by arrow 94. The threads of pulley 76 are used mainly to provide cable 80 with a better grip on pulley 76. In alternate embodiments, pulley 76 includes no threads, and the high tension in cable 80 allows cable 80 to grip pulley 76.

Capstan drive mechanism 58 is advantageously used in the present invention to provide transmission of forces and mechanical advantage between transducers 66a and 66b and object 44 without introducing substantial compliance, friction, or backlash to the system. A capstan drive provides increased stiffness, so that forces are transmitted with negligible stretch and compression of the components. The amount of friction is also reduced with a capstan drive mechanism so that substantially "noiseless" tactile signals can be provided to the user. In addition, the amount of backlash contributed by a capstan drive is also negligible. "Backlash" is the amount of play that occurs between two coupled rotating objects in a gear or pulley system. Two gears, belts, or other types of drive mechanisms could also be used in place of capstan drive mechanism 58 in alternate embodiments to transmit forces between transducer 66a and extension member 48b. However, gears and the like typically introduce some backlash in the system. In addition, a user might be able to feel the interlocking and grinding of gear teeth during rotation of gears when manipulating object 44; the rotation in a capstan drive mechanism is much less noticeable.

FIG. 6 is a perspective view of central drive member 50a and linear axis member 40 shown in some detail. Central drive member 50a is shown in a partial cutaway view to expose the interior of member 50a. Central transducer 68 is coupled to one side of central drive member 50a. In the described embodiment, a capstan drive mechanism is used to transmit forces between transducer 68 and linear axis member 40 along the third degree of freedom. A rotatable shaft 98 of transducer 68 extends through a bore in the side wall of central drive member 50a and is coupled to a capstan pulley 100. Pulley 100 is described in greater detail below with respect to FIG. 6a.

Linear axis member 40 preferably includes an exterior sleeve 91 and an interior shaft 93 (described with reference to FIG. 6b, below). Exterior sleeve 91 is preferably a partially cylindrical member having a flat 41 provided along its length. Flat 41 prevents sleeve 91 from rotating about axis C in the fourth degree of freedom described above. Linear axis member 40 is provided with a cable 99 which is secured on each end of member 40 by tension caps 101. Cable 99 preferably runs down a majority of the length of exterior sleeve 91 on the surface of flat 41 and can be tightened, for example, by releasing a screw 97, pulling an end of cable 99 until the desired tension is achieved, and tightening screw 97. Similarly to the cable of the capstan mechanism described with reference to FIG. 5, cable 99 should have a relatively high tension.

As shown in FIG. 6a, cable 99 is wrapped a number of times around pulley 100 so that forces can be transmitted between pulley 100 and linear axis member 40. Pulley 100 preferably includes a central axle portion 103 and end lip portions 105. Exterior sleeve 91 is preferably positioned such that flat 41 of the sleeve is touching or is very close to lip portions 105 on both sides of axle portion 103. The cable 99 portion around pulley 100 is wrapped around central axle portion 103 and moves along portion 103 towards and away from shaft 98 as the pulley is rotated clockwise and counterclockwise, respectively. The diameter of axle portion 103 is smaller than lip portion 105, providing space between the pulley 100 and flat 41 where cable 99 is attached and allowing free movement of the cable. Pulley 100 preferably does not include threads, unlike pulley 76, since the tension in cable 99 allows the cable to grip pulley 100 tightly. In other embodiments, pulley 100 can be a threaded or unthreaded cylinder similar to capstan pulley 76 described with reference to FIG. 5.

Using the capstan drive mechanism, transducer 68 can translate linear axis member 40 along axis C when the pulley is rotated by the actuator of transducer 68. Likewise, when linear axis member 40 is translated along axis C by the user manipulating object 44, pulley 100 and shaft 98 are rotated;

this rotation is detected by the sensor of transducer 68. The capstan drive mechanism provides low friction and smooth, rigid operation for precise movement of linear axis member 40 and accurate position measurement of the member 40.

Other drive mechanisms can also be used to transmit forces to linear axis member and receive positional information from member 40 along axis C. For example, a drive wheel made of a rubber-like material or other frictional material can be positioned on shaft 98 to contact linear axis member 40 along the edge of the wheel. The wheel can cause forces along member 40 from the friction between wheel and linear axis member. Such a drive wheel mechanism is disclosed in the abovementioned application Ser. No. 08/275,120 as well as in U.S. Pat. No. 5,623,512, filed Nov. 23, 1994 and entitled "Method and Apparatus for Providing Mechanical I/O for Computer Systems Interfaced with Elongated Flexible Objects" assigned to the assignee of the present invention and incorporated herein by reference in its entirety. Linear axis member 40 can also be a single shaft in alternate embodiments instead of a dual part sleeve and shaft.

Referring to the cross sectional side view of member 40 and transducer 70 shown in FIG. 6b, interior shaft 93 is positioned inside hollow exterior sleeve 91 and is rotatably coupled to sleeve 91. A first end 107 of shaft 93 preferably extends beyond sleeve 91 and is coupled to object 44. When object 44 is rotated about axis C, shaft 93 is also rotated about axis C in the fourth degree of freedom within sleeve 91. Shaft 93 is translated along axis C in the third degree of freedom when sleeve 91 is translated. Alternatively, interior shaft 93 can be coupled to a shaft of object 44 within exterior sleeve 91. For example, a short portion of shaft 28 of laparoscopic tool 18, as shown in FIG. 1, can extend into sleeve 91 and be coupled to shaft 93 within the sleeve, or shaft 28 can extend all the way to transducer 70 and functionally be used as shaft 93.

Shaft 93 is coupled at its second end 109 to transducer 70, which, in the preferred embodiment, is an optical encoder sensor. The housing 111 of transducer 70 is rigidly coupled to exterior sleeve 91 by a cap 115, and a shaft 113 of transducer 70 is coupled to interior shaft 93 so that transducer 70 can measure the rotational position of shaft 93 and object 44. In alternate embodiments, an actuator can also be included in transducer 70 to provide rotational forces about axis C to shaft 93.

Figure 7:
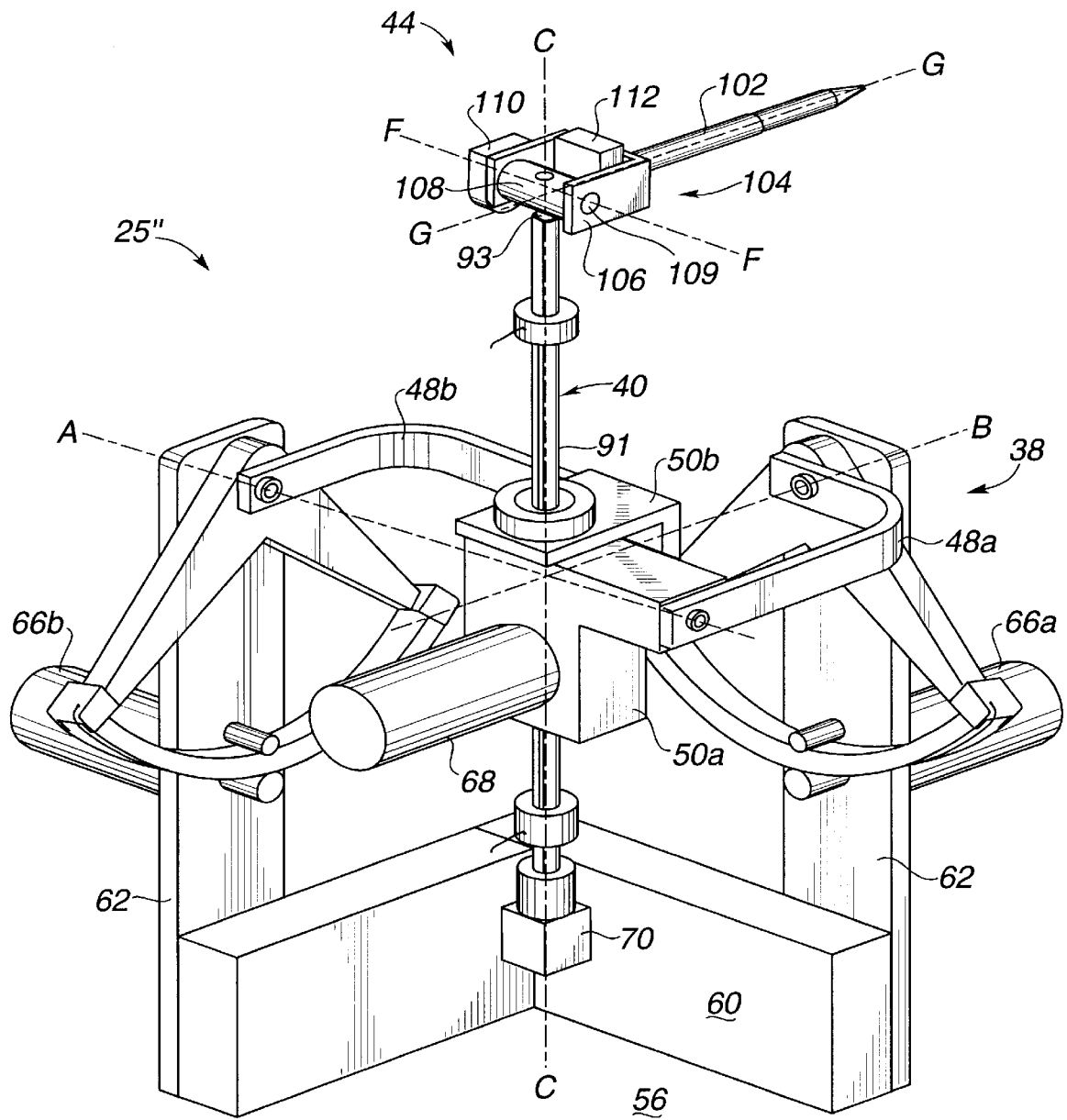
FIG. 7 is a perspective view of an embodiment of the apparatus of FIG. 2 having a stylus object for the user.

FIG. 7 is a perspective view of an alternate embodiment of the mechanical apparatus 25" and user object 44 of the present invention. Mechanical apparatus 25" shown in FIG. 7 operates substantially the same as apparatus 25' shown in FIGS. 3 and 4. User object 44, however, is a stylus 102 which the user can grasp and move in six degrees of freedom. By "grasp", it is meant that users may releasably engage a grip portion of the object in some fashion, such as by hand, with their fingertips, or even orally in the case of handicapped persons. Stylus 102 can be sensed and force can be applied in various degrees of freedom by a computer system and interface such as computer 16 and interface 14 of FIG. 1. Stylus 102 can be used in virtual reality simulations in which the user can move the stylus in 3D space to point to objects, write words, drawings, or other images, etc. For example, a user can view a virtual environment generated on a computer screen or in 3D goggles. A virtual stylus can be presented in a virtual hand of the user. The computer system tracks the position of the stylus with sensors as the user moves it. The computer system also provides force feedback to the stylus when the user moves the stylus against a virtual desk top, writes on a virtual pad of paper, etc. It thus appears and feels to the user that the stylus is contacting a real surface.

Stylus 102 preferably is coupled to a floating gimbal mechanism 104 which provides two degrees of freedom in addition to the four degrees of freedom provided by apparatus 25' described with reference to FIGS. 3 and 4. Floating gimbal mechanism 104 includes a U-shaped member 106 which is rotatably coupled to an axis member 108 by a shaft 109 so that U-shaped member 106 can rotate about axis F. Axis member 108 is rigidly coupled to linear axis member 40. In addition, the housing of a transducer 110 is coupled to U-shaped member 106 and a shaft of transducer 110 is coupled to shaft 109. Shaft 109 is preferably locked into position within axis member 108 so that as U-shaped member 106 is rotated, shaft 109 does not rotate. Transducer 110 is preferably a sensor, such as an optical encoder as described above with reference to transducer 70, which measures the rotation of U-shaped member 106 about axis F in a fifth degree of freedom and provides electrical signals indicating such movement to interface 14.

Stylus 102 is preferably rotatably coupled to U-shaped member 106 by a shaft (not shown) extending through the U-shaped member. This shaft is coupled to a shaft of transducer 112, the housing of which is coupled to U-shaped member 106 as shown. Transducer 112 is preferably a sensor, such as an optical encoder as described above, which measures the rotation of stylus 102 about the lengthwise axis G of the stylus in a sixth degree of freedom.

In the described embodiment of FIG. 7, six degrees of freedom of stylus 102 are sensed. Thus, both the position (x, y, z coordinates) and the orientation (roll, pitch, yaw) of the stylus can be detected by computer 16 to provide a highly realistic simulation. Other mechanisms besides the floating gimbal mechanism 104 can be used to provide the fifth and sixth degrees of freedom. In addition, forces can be applied in three degrees of freedom for stylus 102 to provide 3D force feedback. In alternate embodiments, actuators can also be included in transducers 70, 110, and 112. However, actuators are preferably not included for the fourth, fifth, and sixth degrees of freedom in the described embodiment, since actuators are typically heavier than sensors and, when positioned at the locations of transducers 70, 100, and 112, would create more inertia in the system. In addition, the force feedback for the designated three degrees of freedom allows impacts and resistance to be simulated, which is typically adequate in many virtual reality applications. Force feedback in the fourth, fifth, and sixth degrees of freedom would allow torques on stylus 102 to be simulated as well, which may or may not be useful in a simulation.

Figure 8:
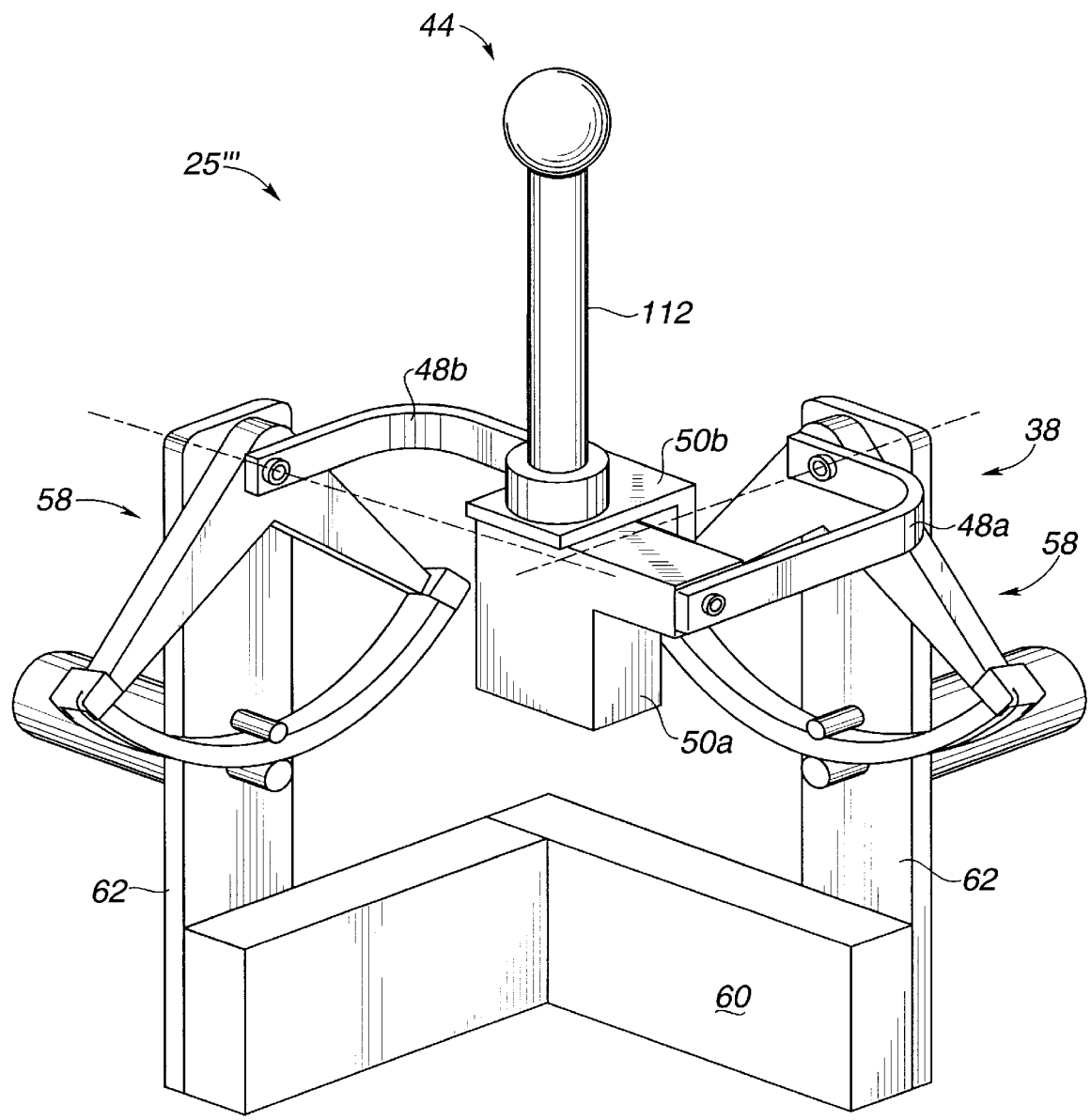
FIG. 8 is a perspective view of an embodiment of the apparatus of FIG. 2 having a joystick object for the user.

FIG. 8 is a perspective view of a second alternate embodiment of the mechanical apparatus 25''' and user object 44 of the present invention. Mechanical apparatus 25''' shown in FIG. 8 operates substantially the same as apparatus 25' shown in FIGS. 3 and 4. User object 44, however, is a joystick 112 which the user can preferably move in two degrees of freedom. Joystick 112 can be sensed and force can be applied in both degrees of freedom by a computer system and interface similar to computer system 16 and interface 14 of FIG. 1. In the described embodiment, joystick 112 is coupled to cylindrical fastener 64 so that the user can move the joystick in the two degrees of freedom provided by gimbal mechanism 38 as described above. Linear axis member 40 is not typically included in the embodiment of FIG. 8, since a joystick is not usually translated along an axis C. However, in alternate embodiments, joystick 112 can be coupled to linear axis member 40 similarly to stylus 102 as shown in FIG. 7 to provide a third degree of freedom. In yet other embodiments, linear axis member 40 can rotate about axis C and transducer 70 can be coupled to apparatus 25''' to provide a fourth degree of freedom. Finally, in other embodiments, a floating gimbal mechanism as shown in FIG. 7, or a different mechanism, can be added to the joystick to allow a five or six degrees of freedom.

Joystick 112 can be used in virtual reality simulations in which the user can move the joystick to move a vehicle, point to objects, control a mechanism, etc. For example, a user can view a virtual environment generated on a computer screen or in 3D goggles in which joystick 112 controls an aircraft. The computer system tracks the position of the joystick as the user moves it around with sensors and updates the virtual reality display accordingly to make the aircraft move in the indicated direction, etc. The computer system also provides force feedback to the joystick, for example, when the aircraft is banking or accelerating in a turn or in other situations where the user may experience forces on the joystick or find it more difficult to steer the aircraft.

Figure 9:
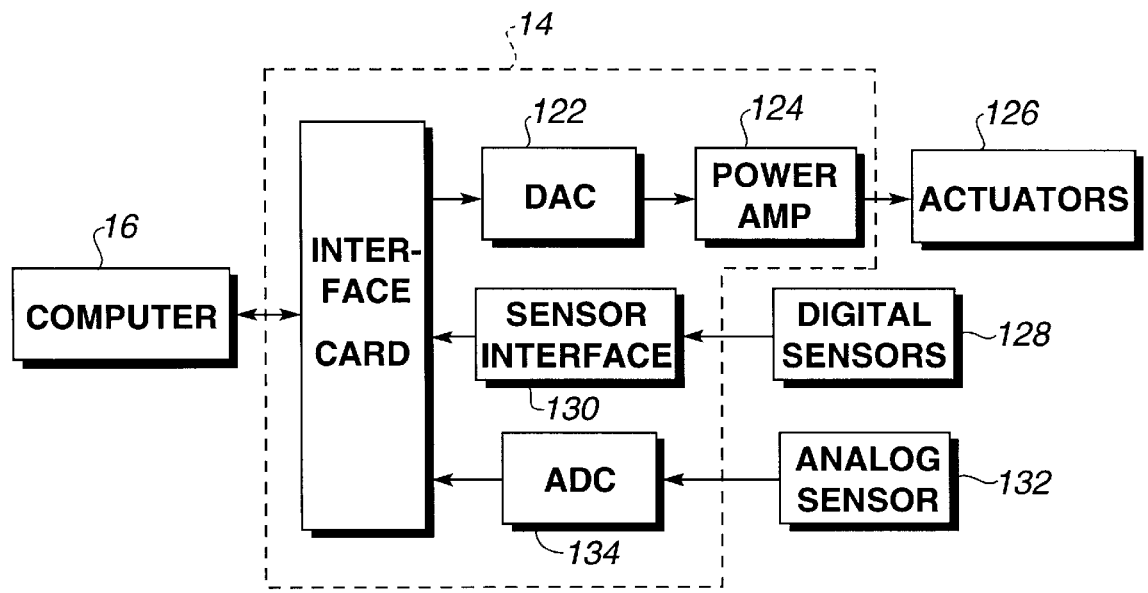
FIG. 9 is a block diagram of a computer and the interface between the computer and the mechanical apparatus of FIG. 2.

FIG. 9 is a schematic view of a computer 16 and an interface circuit 120 that may be used in interface 14 to send and receive signals from mechanical apparatus 25. Interface circuit 120 includes computer 16, interface card 120, DAC 122, power amplifier circuit 124, digital sensors 128, and sensor interface 130. Optionally included are analog sensors 132 instead of or in addition to digital sensors 128, and ADC 134. In this embodiment, the interface 14 between computer 16 and mechanical apparatus 25 as shown in FIG. 1 can be considered functionally equivalent to the interface circuits enclosed within the dashed line in FIG. 14. Other types of interfaces 14 can also be used. For example, another type of interface circuit is described below with respect to FIG. 20.

Interface card 120 can be implemented as a standard card which fits into an interface slot of computer 16. For example, if computer 16 is an IBM-compatible X86 computer, interface card 14 can be implemented as an ISA or other well-known standard interface card which plugs into the motherboard of the computer and provides input and output ports connected to the main data bus of the computer.

Digital to analog converter (DAC) 122 is coupled to interface card 120 and receives a digital signal from computer 16. DAC 122 converts the digital signal to analog voltages which are then sent to power amplifier circuit 124. A DAC circuit suitable for use with the present invention is described with reference to FIG. 10. Power amplifier circuit 124 receives an analog low-power control voltage from DAC 122 and amplifies the voltage to control actuators 126. Power amplifier circuit 124 is described in greater detail with reference to FIG. 11. Actuators 126 are preferably DC servo motors incorporated into the transducers 66a, 66b, and 68, and any additional actuators, as described with reference to the embodiments shown in FIGS. 3, 7, and 8 for providing force feedback to a user manipulating object 44 coupled to mechanical apparatus 25.

Digital sensors 128 provide signals to computer 16 relating the position of the user object 44 in 3D space. In the preferred embodiments described above, sensors 128 are relative optical encoders, which are electro-optical devices that respond to a shaft's rotation by producing two phase-related signals. In the described embodiment, sensor interface circuit 130, which is preferably a single chip, receives the signals from digital sensors 128 and converts the two signals from each sensor into another pair of clock signals, which drive a bi-directional binary counter. The output of the binary counter is received by computer 16 as a binary number representing the angular position of the encoded shaft. Such circuits, or equivalent circuits, are well known to those skilled in the art; for example, the Quadrature Chip LS7166 from Hewlett Packard, California performs the functions described above. Each sensor 28 can be provided with its own sensor interface, or one sensor interface may handle data from multiple sensors. For example, the electronic interface described in U.S. Pat. No. 5,576,727, describes a sensor interface including a separate processing chip dedicated to each sensor that provides input data.

Analog sensors 132 can be included instead of digital sensors 128 for all or some of the transducers of the present invention. For example, a strain gauge can be connected to measure forces on object 44 rather than positions of the object. Also, velocity sensors and/or accelerometers can be used to directly measure velocities and accelerations on object 44. Analog sensors 132 can provide an analog signal representative of the position/velocity/acceleration of the user object in a particular degree of freedom. An analog to digital converter (ADC) can convert the analog signal to a digital signal that is received and interpreted by computer 16, as is well known to those skilled in the art. The resolution of the detected motion of object 44 would be limited by the resolution of the ADC.

Figure 10:
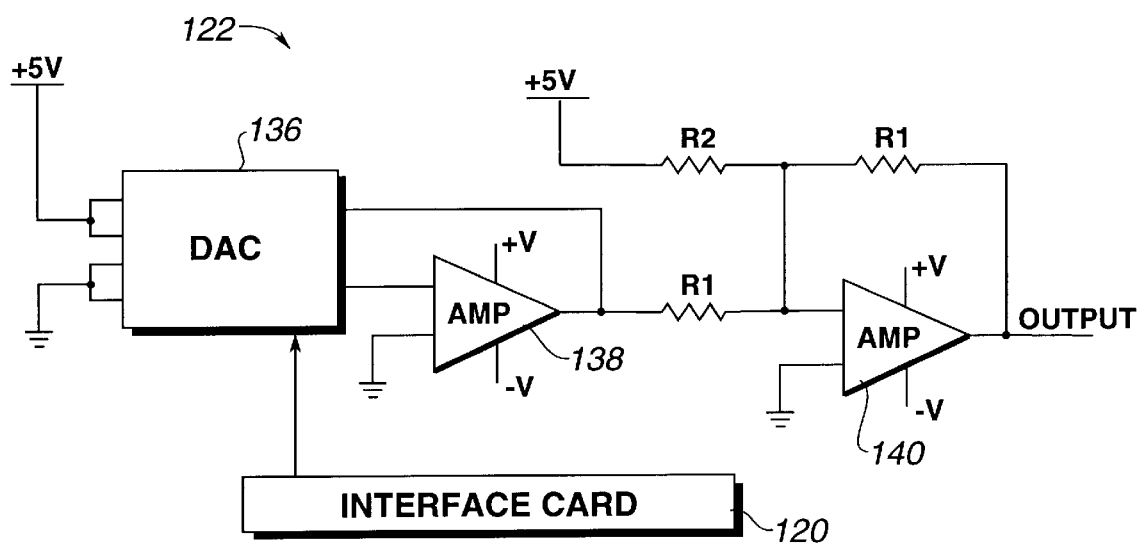
FIG. 10 is a schematic diagram of a suitable circuit for a digital to analog controller of the interface of FIG. 9.

FIG. 10 is a schematic view of a DAC circuit 122 of FIG. 9 suitable for converting an input digital signal to an analog voltage that is output to power amplifier circuit 124. In the described embodiment, circuit 122 includes a parallel DAC 136, such as the DAC1220 manufactured by National Semiconductor, which is designed to operate with an external generic op amp 138. Op amp 138, for example, outputs a signal from zero to −5 volts proportional to the binary number at its input. Op amp 140 is an inverting summing amplifier that converts the output voltage to a symmetrical bipolar range. Op amp 140 produces an output signal between −2.5 V and +2.5 V by inverting the output of op amp 138 and subtracting 2.5 volts from that output; this output signal is suitable for power amplification in amplification circuit 124. As an example, R1=200 kΩ and R2=400 kΩ. Of course, circuit 122 is intended as one example of many possible circuits that can be used to convert a digital signal to a desired analog signal.

Figure 11:
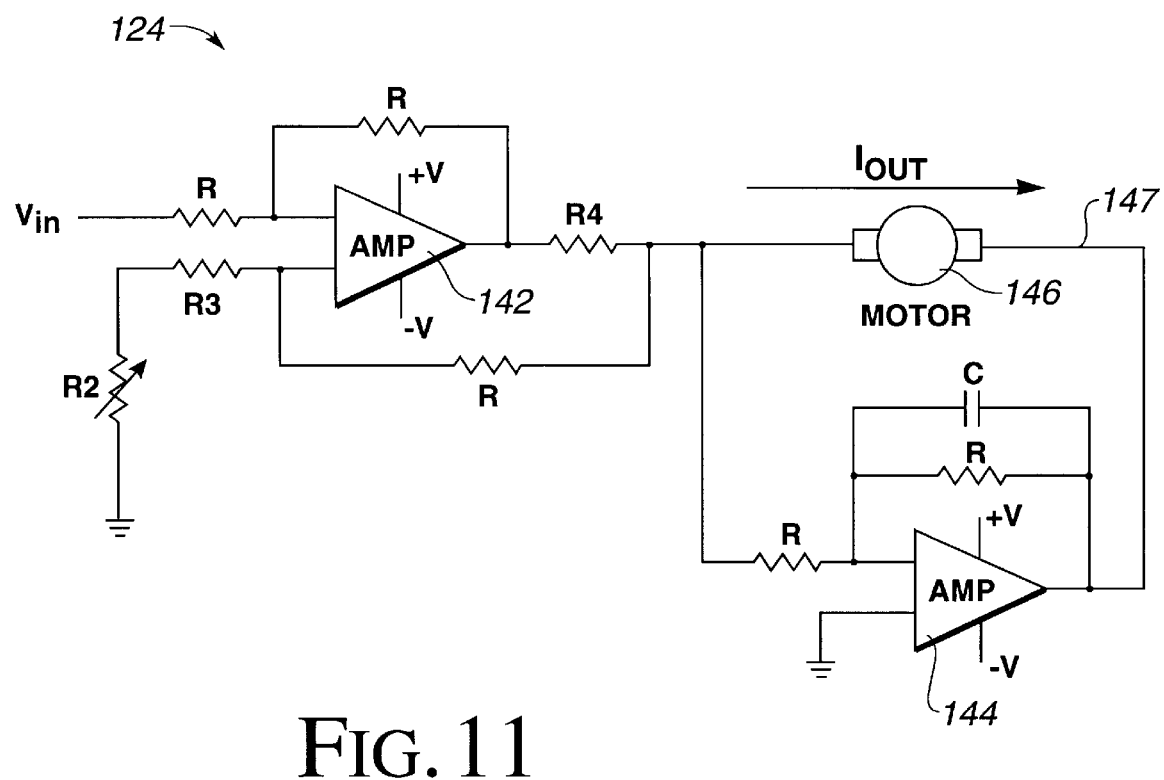
FIG. 11 is a schematic diagram of a suitable power amplification circuit for powering the actuators of the present invention as shown in FIG. 9.

FIG. 11 is a schematic view of a power amplifier circuit 124 suitable for use in the interface circuit 14 shown in FIG. 9. Power amplifier circuit receives a low power control voltage from DAC circuit 122 to control high-power, current-controlled servo motor 126. The input control voltage controls a transconductance stage composed of amplifier 142 and several resistors. The transconductance stage (commonly referred to as a Howland current pump) produces an output current proportional to the input voltage to drive motor 126 while drawing very little current from the input voltage source. The second amplifier stage, including amplifier 144, resistors, and a capacitor C, provides additional current capacity by enhancing the voltage swing of the second terminal 147 of motor 146. As example values for circuit 124, R=10 kΩ, R2=500 Ω, R3=9.75 kΩ, and R4=1 Ω. Of course, circuit 124 is intended as one example of many possible circuits that can be used to amplify voltages to drive actuators 126.

Figure 12:
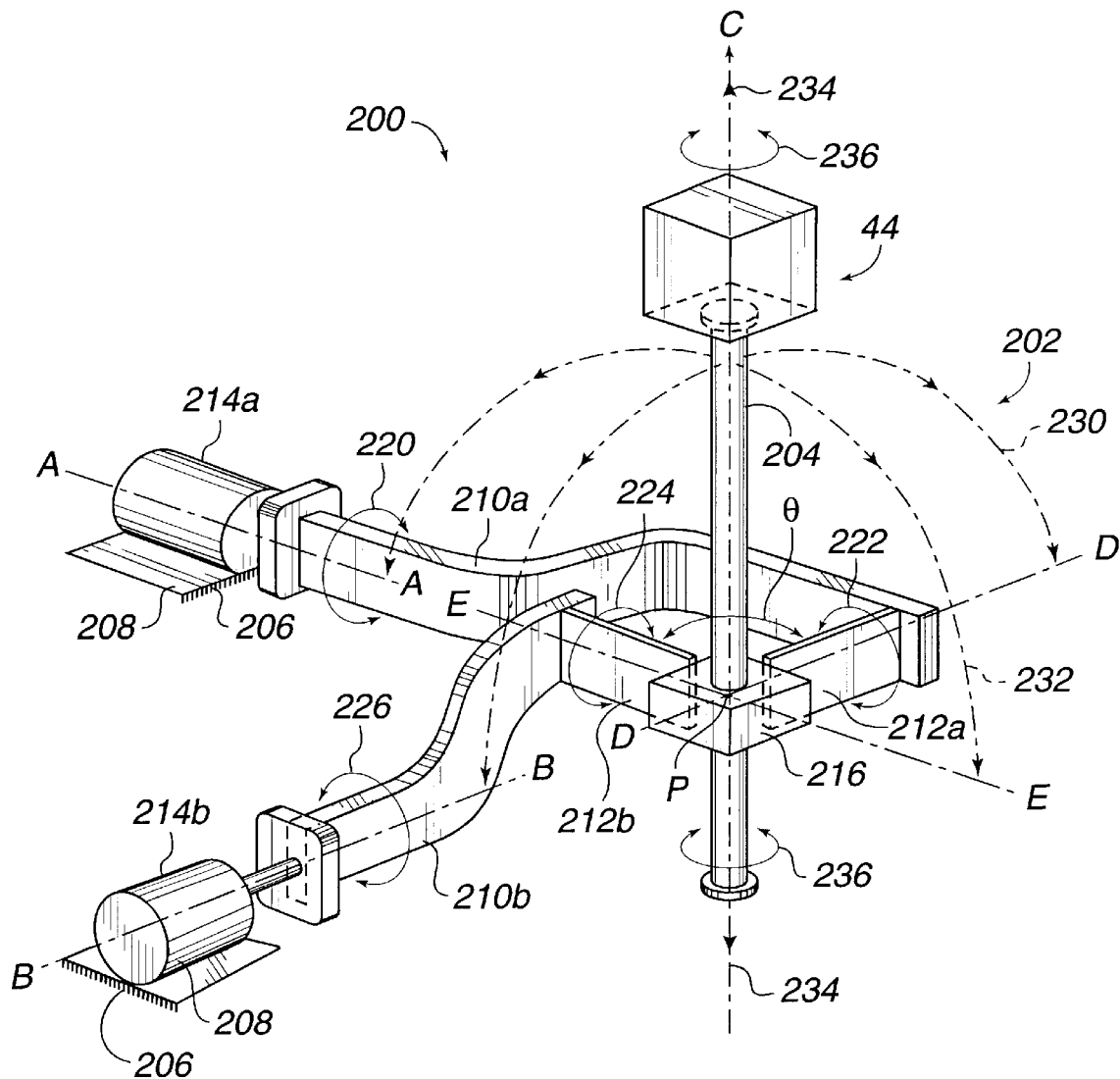
FIG. 12 is a perspective view of an alternate embodiment of the mechanical apparatus of FIG. 2 including flexible members.

FIG. 12 is a perspective view of an alternate embodiment 200 of the mechanical interface apparatus 25 of the present invention. Apparatus 200 includes a gimbal mechanism 202 and an optional linear axis member 204. User object 44 is preferably coupled to linear axis member 204. Alternatively, user object 44 can be coupled directly to the gimbal mechanism 202.

Gimbal mechanism 202 is similar in some respects to gimbal mechanism 38 as described above with reference to FIG. 2. Gimbal mechanism 202 can be supported on a grounded surface 206 (schematically shown as part of ground member 208). Grounded surface 206 can be a tabletop or other fixed, stable surface. The grounded surface can also be fixed relative to only apparatus 200 such that the grounded surface and apparatus 200 can be moved by user as an entire unit.

Gimbal mechanism 202 preferably includes a multi-segment flexure that is rotatably coupled to a ground member 208. Gimbal mechanism 202 includes a ground member 208, extension members 210a and 210b, and central members 212a and 212b. Ground member 208, shown schematically, is coupled to grounded surface 206 which provides stability for apparatus 200. Ground member 208 is shown in FIG. 12 as two separate symbols coupled together through grounded surface 206, but ground member 208 can be considered to be one "member" that is grounded. An example of a ground member 208 including members 60 and 62 is shown above in FIG. 3. It should be noted that members 210a, 210b, 212a, and 212b are referred to herein as "members" due to the similarity of the rotatably-coupled members described with reference to FIG. 2. However, these "members" of gimbal 202 can be considered "segments" of a "multi-segment flexure" or a "unitary member," that is rotatably coupled to ground member 208.

The central members 212a and 212b are flexible members having a torsion flex (twist) and bending compliance so that the object 44 can be moved in two or three degrees of freedom about axes A, B, and C, as explained below. Axes A and B are fixed in position with respect to the ground surface 206 (i.e., grounded) and are substantially mutually perpendicular. As described above with reference to FIG. 2, floating axes C, D and E are not fixed in one position as are axes A and B. Floating axes D and E are coincident with axes B and A, respectively, when the user object 44 is in a central position as shown in FIG. 12. Floating axis C preferably extends approximately through the point of intersection P of axes A and B.

Extension member 210a is rotatably coupled to ground member 206 at a first end. In the example of FIG. 12, a rotary bearing 214a is provided between the extension member 210a and ground member 206 such that the extension member 210a is rotatable about grounded axis A. For example, bearing 214a can be part of a transducer 42 as described above, such as an actuator and/or a sensor. Such a transducer, for example, includes a rotatable shaft to which the extension member 210a can be rigidly coupled. Extension member 210a is a rigid member similar to the extension member 48a as shown with respect to FIG. 2, and can be made of a material such as rigid plastic, metal, or the like. Extension member 210a rotates about axis A as shown by arrow 220.

The second end of extension member 210a is rigidly coupled to a first end of central member 212a. Central member 212a is aligned parallel with a floating axis D and is made of a material such as flexible plastic, rubber, metal, or the like, that provides torsion flex (twist) and bending in a particular desired degree of freedom. Compliance or flex can also be provided with spring members and the like. Herein, the term "flex" is intended to refer to any sort of flexibility in a member or segment. Types of flex described herein include twist (torsion flex) and bending. Twist is the torque twisting motion about a member's lengthwise axis, and bending is the relative movement of the two ends of a member towards or away from each other.

In the described embodiment, central member 212a can flex about the floating axis D. As shown in FIG. 12, central member 212a is relatively narrow in the dimension that the central member is to flex, and relatively wide in the dimensions in which the central member is desired to remain rigid. Since the central member 212a has a relatively large width in the dimensions of axes C and D, the member will not easily flex in those dimensions. However, the central member 212a has a relatively small width in the dimension of a floating axis E, and is thus compliant in that dimension. This allows the central member 212a to twist about floating axis D, as shown by arrow 222, when object 44 is rotated about axis D. This twisting motion substitutes for the rotary motion of central member 50a about axis D as allowed by rotary bearing 45a, as described above for FIG. 2. In addition to twisting about axis D, central member 212a can bend in the plane of axes D and E. This bending motion substitutes for the rotary motion of the central member 50a about axis C as allowed by rotary bearing 47, as explained with respect to FIG. 2. Since central member 212a can flex, this member is "flexibly coupled" to extension member 210a. In other embodiments, central members 212a and 212b can be provided with other geometries that allow the twisting and bending motions described above.

In the described embodiment, the second end of central member 212a is rigidly coupled to object member 216, which is positioned about at the center point P at the intersection of axes D and E. Object member 216 can support linear axis member 204 or user object 44. The size and shape of object member 216 can vary widely in different embodiments. Object member 216 preferably includes an aperture through which a linear axis member 204 or user object 44 can translate. In alternate embodiments where object 44 does not translate, object member 216 can be omitted and the second end of central member 212a and the first end of central member 212b can be directly and rigidly coupled to the user object 44, which can be placed at about the center point P at the intersection of the axes D and E. For example, in a joystick embodiment having two degrees of freedom, a joystick handle can be coupled directly to central members 212a and 212b (shown in FIG. 13).

Central member 212b is similar to central member 212a and includes a first end that is rigidly coupled to object 216. Central member 212b is preferably aligned with floating axis E and is narrow in the dimension of axis D and wide in the dimensions of axes E and C. This allows the central member 212b to twist about floating axis E, as indicated by arrow 224. Central member 212b may also bend in the plane of axes D and E. A first end of extension member 210b is rigidly coupled to the second end of central member 212b. Extension member 210b is rigid similarly to extension member 210a and extends in a fashion such that the second end of the extension member 210b is positioned on axis B. A rotatable bearing 214b is rotatably coupled to the second end of extension member 210b, thus allowing extension member 210b to rotate about axis B as indicated by arrow 226. As for bearing 214a, bearing 214b can be part of a transducer such as a actuator or sensor. Bearing 214b is rigidly coupled to ground member 208 to complete the closed loop of members.

Gimbal mechanism 202 is formed as a closed chain or "flexure" of five "members." Each end of one member is coupled to the end of another member. The flexure is arranged such that extension member 210a, central member 212a, and central member 212b can be rotated about axis A in a first degree of freedom. The linkage is also arranged such that extension member 210b, central member 212b, and central member 212a can be rotated about axis B in a second degree of freedom. In this sense, the gimbal mechanism 202 is similar to mechanism 38 shown in FIG. 2. When object 44 is moved, the bending ability of the central members 212a and 212b cause the angle θ between the central members to increase or decrease. For example, in the origin position shown in FIG. 12, the angle θ is about 90 degrees. If object 44 is moved such that the top of linear axis member 204 moves away from the viewer ("into" the paper) or toward the viewer (out of the paper), then the angle θ between central members will decrease. Likewise, if the top of linear axis member 204 is moved to the sides as shown in FIG. 12, then the angle θ will increase.

A major difference of the present embodiment from the embodiment of FIG. 2 is that members 210a, 210b, 212a and 212b can be provided as a "unitary member," where these four members are formed and produced coupled together as segments of a single part or "flexure." Gimbal mechanism 202 can thus also be considered a closed loop two member linkage, where one member is a complex unitary member (including these four segments) and the other member is ground member 208 that is rotatably coupled to the unitary member.

Since the members 210a, 210b, 212a, and 212b are formed as a unitary part, bearings or joints between these members do not need to be separately manufactured and the extensive assembly process for these members is not necessary. In contrast, the embodiment of FIG. 2 requires joints between equivalent members to these four members to be produced and for these joints and members to be assembled and fastened together. In consequence, the gimbal mechanism 202 is significantly less expensive to produce than the mechanism 25 of FIG. 2. This allows the mechanical apparatus 200 to be manufactured and provided to the high-volume consumer market while still providing an accurate and realistic force feedback interface to the user. In other embodiments, some of the members 210a, 210b, 212a, and 212b can be formed together as unitary members and some members can be formed separately. For example, extension member 210a and central member 212a can be formed together as segments of one unitary member, while extension member 210b and central member 212b can be formed together as segments of a second unitary member. Alternatively, central members 212a and 212b can be formed together as a unitary member (with or without object member 216 formed between them). Linear axis member 204 is preferably an elongated rod-like member which is translatably coupled to central member 212a and central member 212b near the point of intersection P of axes D and E, and is similar to linear axis member 40 described with reference to FIG. 2. Linear axis member 204 can be used as the object 44 or as part of the object 44, as in shaft 28 of user object 44 as shown in FIG. 1, or as a joystick handle, pool cue, etc. In other embodiments, linear axis member 204 can be coupled between an object 44 and gimbal mechanism 202. Linear axis member 204 is coupled to gimbal mechanism 202 such that it extends out of the plane defined by floating axis D and floating axis E. Linear axis member 204 can be rotated about axis E by rotating extension member 210a, central member 212a, and central member 212b in a first revolute degree of freedom, shown as arrow line 230. Member 204 can also be rotated about axis D by rotating extension member 212b and the two central members about axis D in a second revolute degree of freedom, shown by arrow line 232.

Being translatably coupled to object member 216 (or the ends of central members 210a and 210b), linear axis member 204 can be linearly and independently translated along floating axis C with respect to the gimbal mechanism 202, thus providing a third linear degree of freedom as shown by arrows 234. Axis C can, of course, be rotated about one or both axes A and B as member 204 is rotated about these axes. A transducer can also be coupled to linear axis member 204 for the linear degree of freedom along axis C. The transducer can include an actuator for applying forces in the linear degree of freedom, and/or a sensor for detecting the position of the linear axis member in the linear degree of freedom. Such transducers are described in greater detail in the above embodiments.

In addition, a rotary fourth degree of freedom can be provided to linear axis member 204 (and/or object 44) by rotating or "spinning" the linear axis member about axis C, as indicated by arrow 236. This fourth degree of freedom can be provided by spinning linear axis member 204 within a rotatable bearing of object member 216. Alternatively, a more limited form of spin can be provided by bending the central members to spin the entire object 44 and object member 216. This is described in greater detail with respect to FIG. 13. In addition, transducers can be provided to apply forces and/or sense motion in the rotary fourth degree of freedom, as described in previous embodiments.

Also preferably coupled to gimbal mechanism 202 and linear axis member 204 are transducers, such as sensors and actuators. Such transducers are preferably included as part of the bearings 214a and 214b and provide input to and output from an electrical system, such as computer 16. Transducers that can be used with the present invention are described above with respect to FIG. 3. In addition, strain gauges can be used on the flexible members of the present embodiment (and other embodiments having flexible members) to measure the degree of bending and flex of a selected member. For example, the strain gauge can be placed over the length of a central member 212a or 212b to measure the member's position or the force applied to the member.

User object 44 is coupled to gimbal mechanism 202 either directly or via linear axis member 204. One possible user object 44 is the grip 26 of a laparoscopic tool 18, as shown in FIG. 1, where the shaft 28 of tool 18 can be implemented as part of linear axis member 40. Other examples of user objects include a joystick, as described below.

Figure 13:
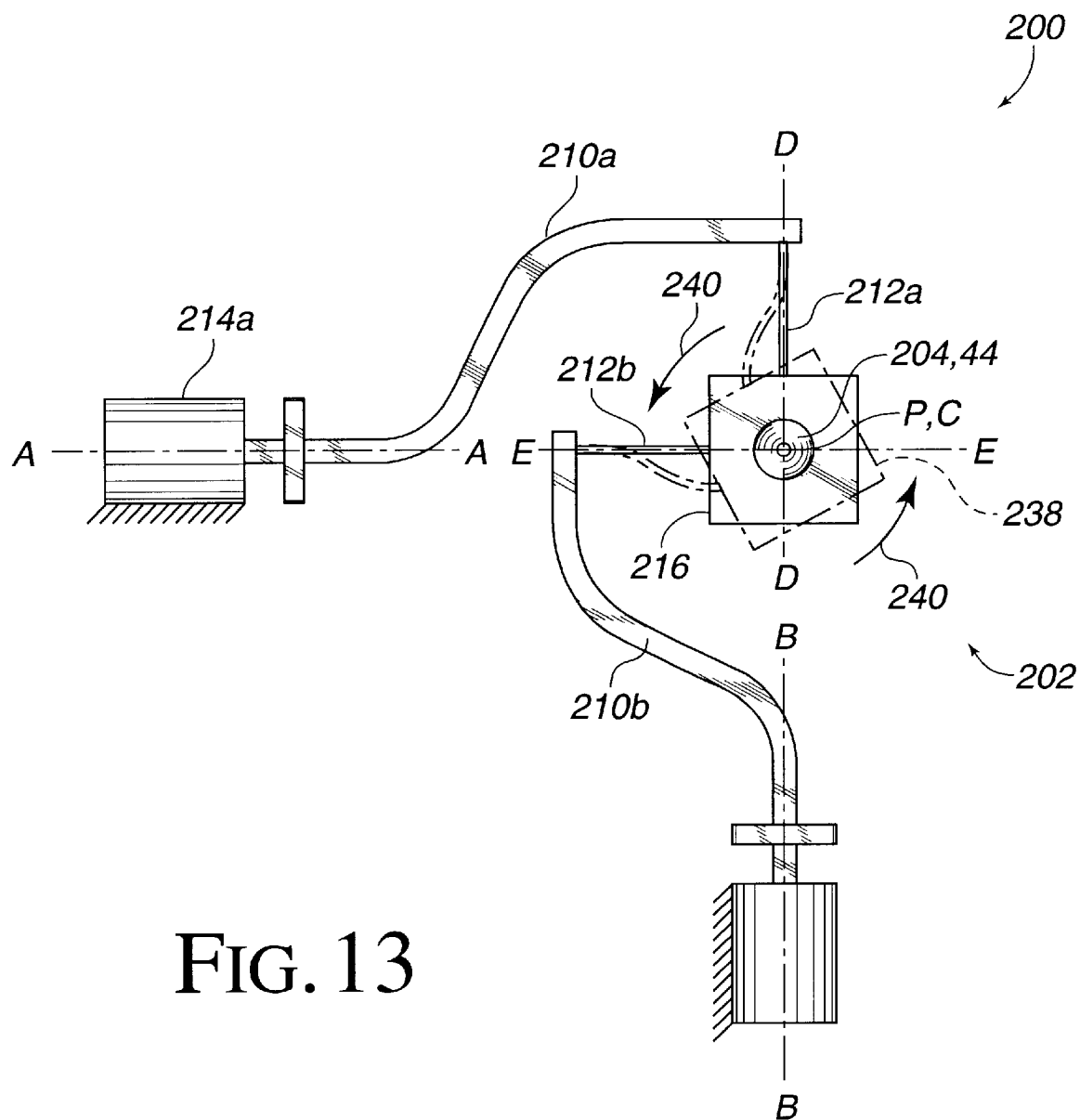
FIG. 13 is a top plan view of the mechanical apparatus of FIG. 12.

FIG. 13 is a top plan view of mechanical apparatus 200 of FIG. 12. Axes A and B are shown substantially perpendicular to each other. If linear axis member 204 is rotatably coupled to object member 216, then a fourth degree of freedom about axis C can be provided. However, in other embodiments, linear axis member 204 can be rigidly coupled to object member 216 in the degree of freedom providing the spin about axis C. This spin can still be provided by flexing central members 212a and 212b. This is shown in FIG. 13, where the solid line representation of object member 216 and central members 212a and 212b show these members in a center, neutral position. Dashed line representation 238 shows object member 216 in a rotated position after the object member 216 and linear axis member 204 have been rotated counterclockwise as shown by arrows 240. Central members 212a and 212b have flexed to allow this rotation to take place, as shown by the dotted lines. Thus, depending on the particular flexibility of central members 212a and 212b, the linear axis member 204 and object 44 can be rotated in a limited amount clockwise or counterclockwise about axis C.

In should be noted that, in some embodiments, the linear axis member 204 can be translatable in a third degree of freedom while being "rigidly" coupled to the object member 216 with respect to the fourth degree of freedom (spin). This would allow the linear axis member to be translated along axis C but would prevent the linear axis member from spinning independently of the object member. Such an embodiment can be implemented, for example, by including one or more grooves within the central aperture of the object member 216 oriented along axis C. The linear axis member could include a corresponding number of catch members that engage the grooves to allow translation but not rotation with respect to the object member 216.

Figure 14:
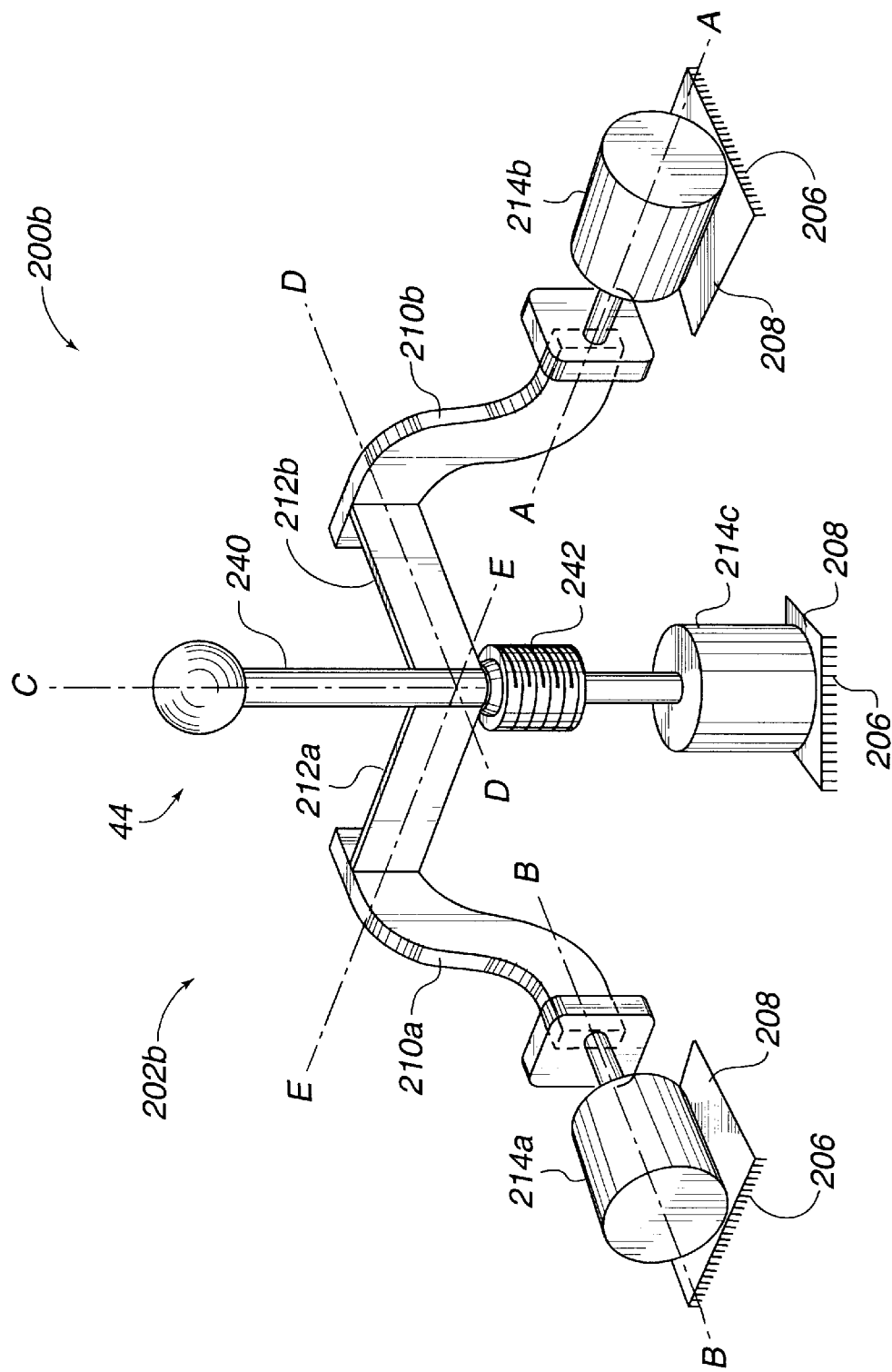
FIG. 14 is a perspective view of a second alternate embodiment of the mechanical apparatus of FIG. 12.

FIG. 14 is a perspective view of an alternate embodiment 200b of the mechanical apparatus 200 shown in FIG. 12. Apparatus 200b includes a gimbal mechanism 202b that is similar to gimbal mechanism 202 and includes ground member 208 (shown schematically coupled to ground surface 206), rigid extension members 210a and 210b, and flexible central members 212a and 212b. In the embodiment of FIG. 14, however, central member 212a and central member 212b are rigidly coupled to object 44, which is shown as a joystick 240. Object 44 thus may not translate along axis C in this embodiment. Object 44, however, can rotate in a limited angular range about axis C as explained above with reference to FIG. 13. In addition, the extension members 210a and 210b of mechanism 202b are shown in a slightly different position to those of mechanism 202. Extension member 210b has been "flipped" to be coupled to object 44 via central member 212b on the opposite side of the object. Either this configuration or the configuration shown in FIG. 12 may be used without significant functional differences.

Furthermore, an additional transducer 214c is shown coupled to one end of the object 44. Transducer 214c is preferably grounded to ground member 208 (or a different member that is coupled to ground). Transducer 214c can include an actuator, such as a motor or brake, for imparting forces on object 44 in the rotary degree of freedom about axis C, and/or a sensor for detecting the motion and position of object 44 in the same rotary degree of freedom. These components are described in greater detail in the above embodiments. This embodiment thus can provide three grounded actuators, which provides more accurate force feedback since the actuators are not carrying the weight of any other actuators. Transducer 214c is coupled to object 44 by a torsion resistant flexure 242, which flexes to allow the object 44 to rotate about axes A and B but does not flex about axis C (i.e., resists torsion forces). Flexure 242 may rotate with a shaft of transducer 214c and thus allow the object 44 to rotate about axis C. The flexure may relay forces and positions of object 44 about axis C even when the flexure is in a flexed position. Such a flexure can take many possible forms, such as a coil or spring, as are well known to those skilled in the art. The grounded transducer 214c and flex coupling 242 can also be coupled to object 44 in other embodiments disclosed herein. In yet other embodiments, torsion resistant flexure 242 can couple object 44 directly to ground member 208 (or ground surface 206), i.e., transducer 214c is omitted. In such an embodiment, object 44 cannot rotate about axis C due to the flexure's resistance to motion in that degree of freedom.

In addition, in other embodiments having a user object 44 translatable along axis C, the torsion resistant flexure 242 can allow such translation. Flexure 242 can be hollow, e.g., the interior space of a coil or spring. A linear axis member 204 or other thin object 44 can be translated through the hollow portion of the flexure 242.

In yet other embodiments in which object 44 does not translate along axis C, object 44, such as a joystick handle, can be extended and coupled to ground member 208 or ground surface 206. For example, a ball joint can be used to provide freedom of motion to object 44 and yet stabilize the object. A sphere, or a portion of a sphere, can be provided on the end of object 44 and fitted to a receiving socket positioned on ground surface 206, as is well known to those skilled in the art. Such a joint is shown and described with reference to FIGS. 22a and 22b. The ball joint allows object 44 to be moved about either axis D or E.

Figure 15:
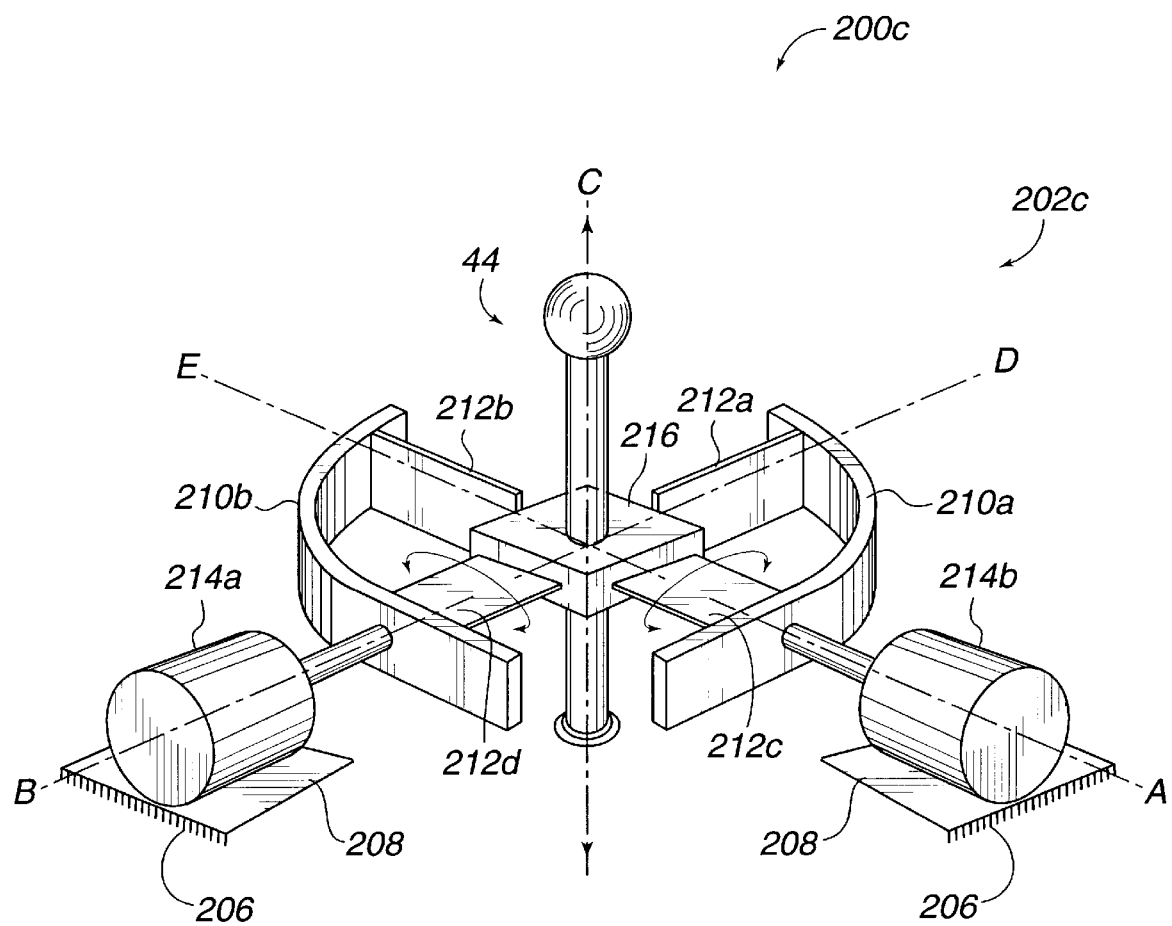
FIG. 15 is a perspective view of a third alternate embodiment of the mechanical apparatus of FIG. 12.

FIG. 15 is a perspective view of a third embodiment 200c of the mechanical apparatus 200 shown in FIG. 12. Apparatus 200c includes a gimbal mechanism 202c that includes ground member 208 (shown schematically coupled to ground surface 206) and rigid extension members 210a and 210b, similar to equivalent members shown in FIGS. 12 and 14. Gimbal mechanism 202c also includes three flexible central members 212a, 212b, and 212c. Central members 212a and 212b are similar to the central members described above with respect to FIGS. 12 and 13, where the members are both wide in the dimension of axis C and narrow in the respective dimensions in which the members may be twisted, i.e., central member 212a has a small width in the dimension of axis A so that the member can be twisted about axis B and bent in the plane of axes D and E. Central members 212a and 212b couple the object 44 to the extension members 210a and 210b and allow the object 44 to rotate about axes A and B (and floating axes D and E).

Central member 212c is coupled between object member 216 (or object 44) and extension member 210a along axis A and floating axis E. Member 212c is flexible like members 212a and 212b, but has a small width in the dimension of the C axis and a relatively large width in the dimensions of axes A and B. These dimensions allow flexible member 212c to twist about axes E and A and bend in the plane of axes A and C. Since flexible member 212a also twists about axes A and E, object 44 can be rotated about axes A and E. However, the relatively large width of flexible member 212c in the plane defined by axes A and B prevents object member 216 from rotating about axis C. This structure provides more stiffness and stability to object 44 in the object's rotation about axes A and E.

Alternatively, a flexible member 212d can be provided instead of flexible member 212c. Member 212d couples object member 216 and object 44 to extension member 210a on the opposite side of object 44 from flexible member 212b. Member 212d is wide in the dimensions of axes A and B and narrow in the dimension of axis C. Member 212d may twist about axes B and D, and bend in the plane of axes B and C, thus providing object 44 a rotary degree of freedom about axes B and D. The larger width of member 212d in the A-B plane prevents object member 216 from rotating about axis C. Typically, only member 212d or 212c is necessary for stability reasons. Both members 212c and 212d can be provided in alternate embodiments.

Figure 16:
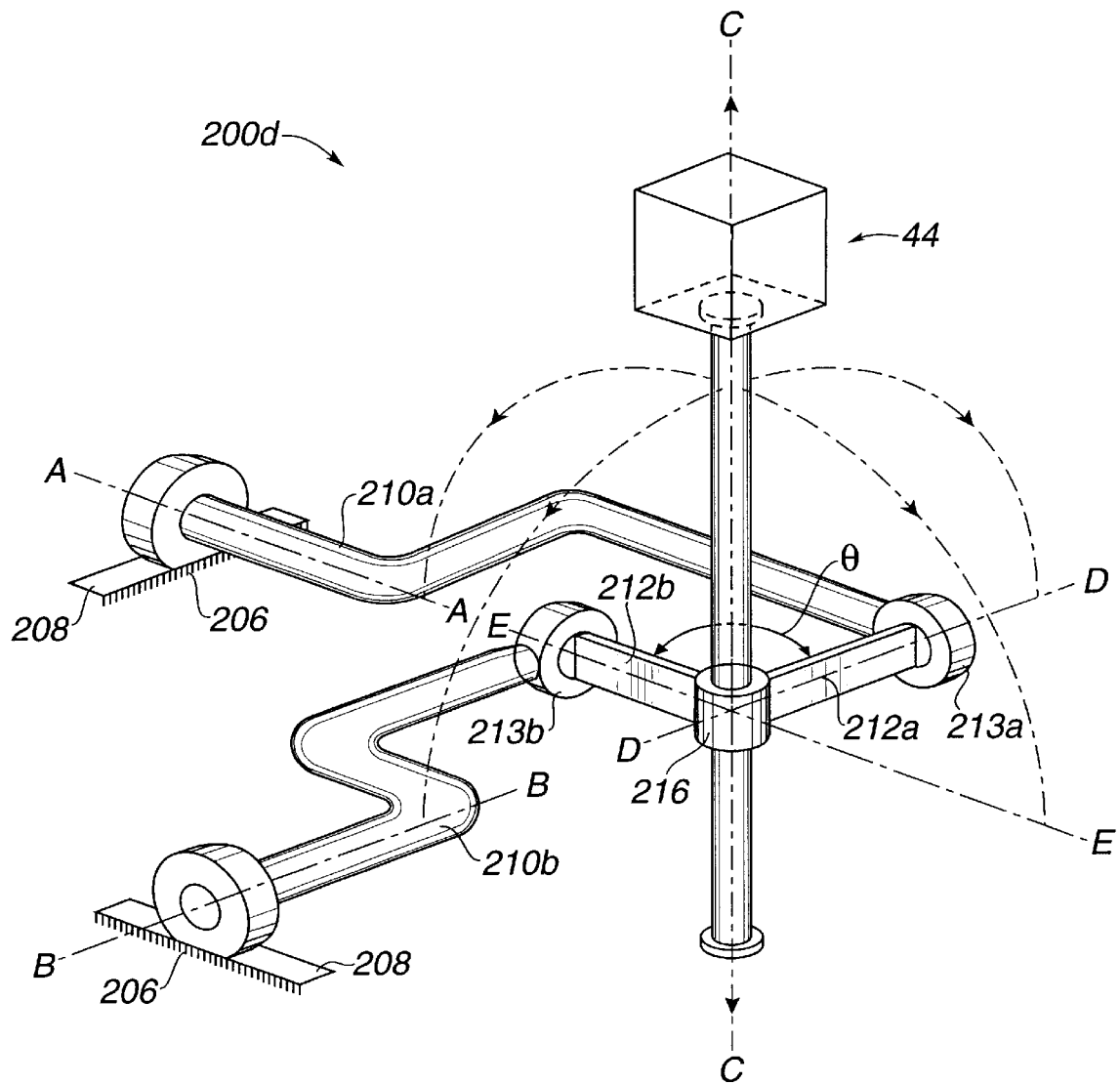
FIG. 16 is a perspective view of a fourth alternate embodiment of the mechanical apparatus of FIG. 12.

Since object member 216 cannot flexibly rotate about axis C in this embodiment, object 44 can be rotatably coupled to object member 216 to allow the object 44 to spin about axis C, if desired. In other embodiments where object 44 is not desired to spin, the object 44 can be directly coupled to flexible members 212a–c. In the embodiment of FIG. 15, object 44 can also be translated along axis C in a linear degree of freedom, as described above with respect to FIG. 12. A third grounded transducer 214c can also be coupled to object 44 as shown in FIG. 14. FIG. 16 is a perspective view of a fourth embodiment 200d of the mechanical apparatus 200 shown in FIG. 12. Apparatus 200d includes a gimbal mechanism 202d that includes ground member 208 (shown schematically coupled to ground surface 206) and rigid extension members 210a and 210b. These members are similar to the equivalent members as described above with respect to FIG. 2. Gimbal mechanism 202d also includes two flexible central members 212a and 212b. Central members 212a and 212b are similar to the central members described above with respect to FIGS. 12 and 13, where the members are both wide in the dimension of axis C and narrow in the respect dimensions in which the members may be rotated. Central members 212a and 212b couple the object 44 to the extension members 210a and 210b and allow the object 44 to rotate about axes A and B (and floating axes D and E).

A difference in the embodiment of FIG. 16 is that flexible members 212a and 212b are rigidly coupled to object 44 (or object member 216) and are rotatably coupled to extension members 210a and 210b, respectively, by bearings 213a and 213b. This allows the flexible members to bend and change the angle θ with respect to each other due to flexure when object 44 is rotated about axes A and B. However, since the flexible members 212a and 212b are rotatably coupled to the extension members, they will not twist when object 44 is moved, but will rotate. The flexure only comes into effect at the ends of flexible members 212a and 212b that are coupled to object 44 or object member 216. This configuration is a compromise between the configurations of FIGS. 2 and 12 and provides more parts and assembly complexity than the embodiment of FIG. 12 due to the extra required bearings 213a and 213b. However, this embodiment allows the flexible members 212a and 212b to rotate more easily and thus provides more realistic force feedback to the user.

Figure 17:
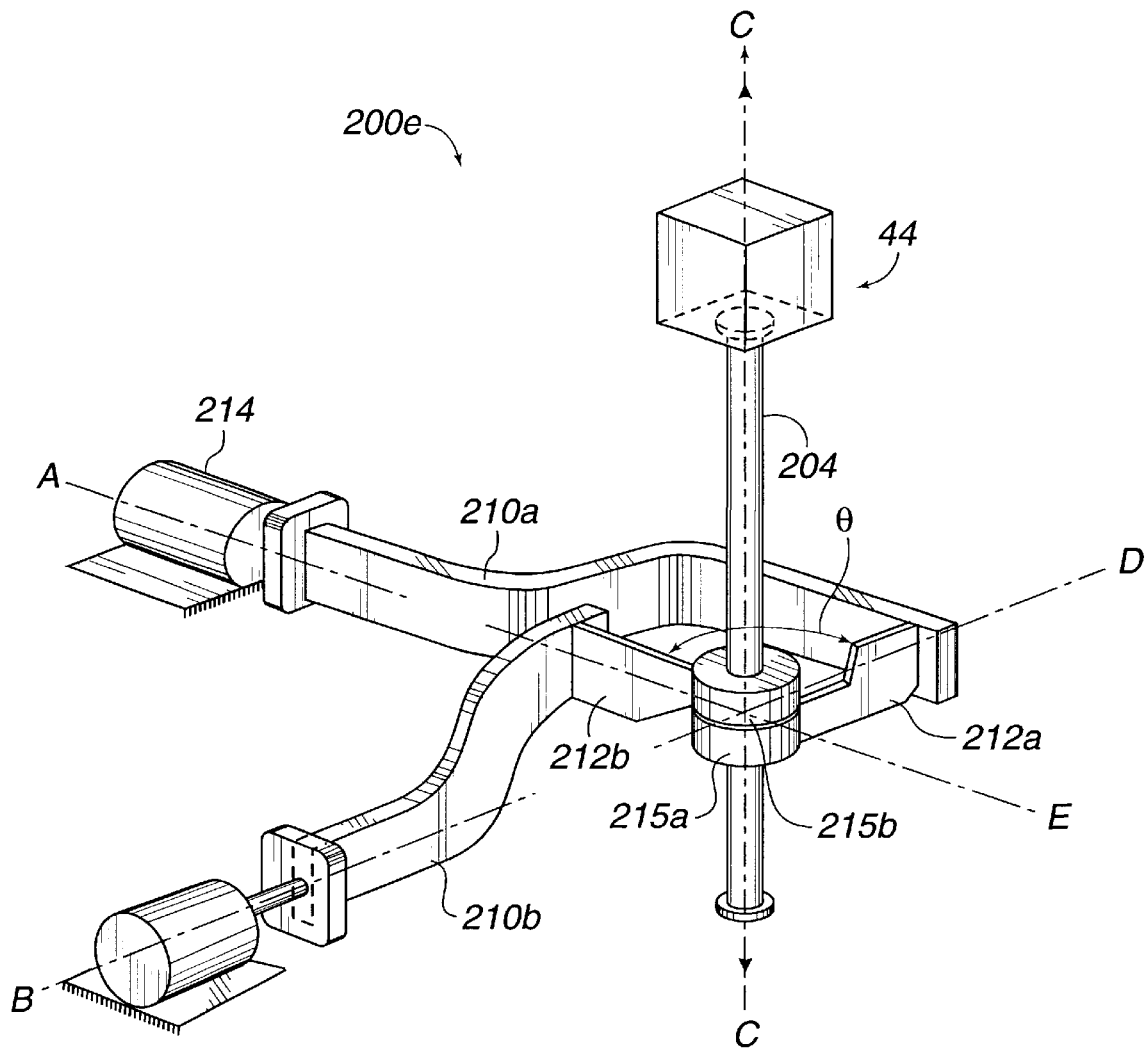
FIG. 17 is a perspective view of a fifth alternate embodiment of the mechanical apparatus of FIG. 12.

FIG. 17 is a perspective view of a fifth embodiment 200e of the mechanical apparatus 200 shown in FIG. 12. Apparatus 200e includes a gimbal mechanism 202e which includes a ground member 208, extension members 210a and 210b, and flexible central members 212a and 212b coupled together similarly to the above embodiments. In most respects, apparatus 200e functions similarly to apparatus 200 of FIG. 12. Flexible members 212a and 212b are rigidly coupled to extension members 210a and 210b, respectively, as in the embodiment of FIG. 12. However, the flexible members are rotatably coupled to object 44 via bearing 215. Bearing 215 provides a rotatable connection between central members 212a and 212b and to object 44 (or linear axis member 204), thus allowing the object or linear axis member to rotate or spin about axis C. When the object 44 is rotated about axes A and B (and D and E), the angle θ between the central members changes due to rotation of bearing 215 instead of due to the bending of the members. The flexible members 212a and 212b twist due to being rigidly coupled to bearing 215 and extension members 210a and 210b. This configuration, like the configuration of FIG. 16, is a compromise between the embodiments of FIGS. 2 and 12 which is more costly than the embodiment of FIG. 12, but also provides more realistic forces to the user.

Figure 18:
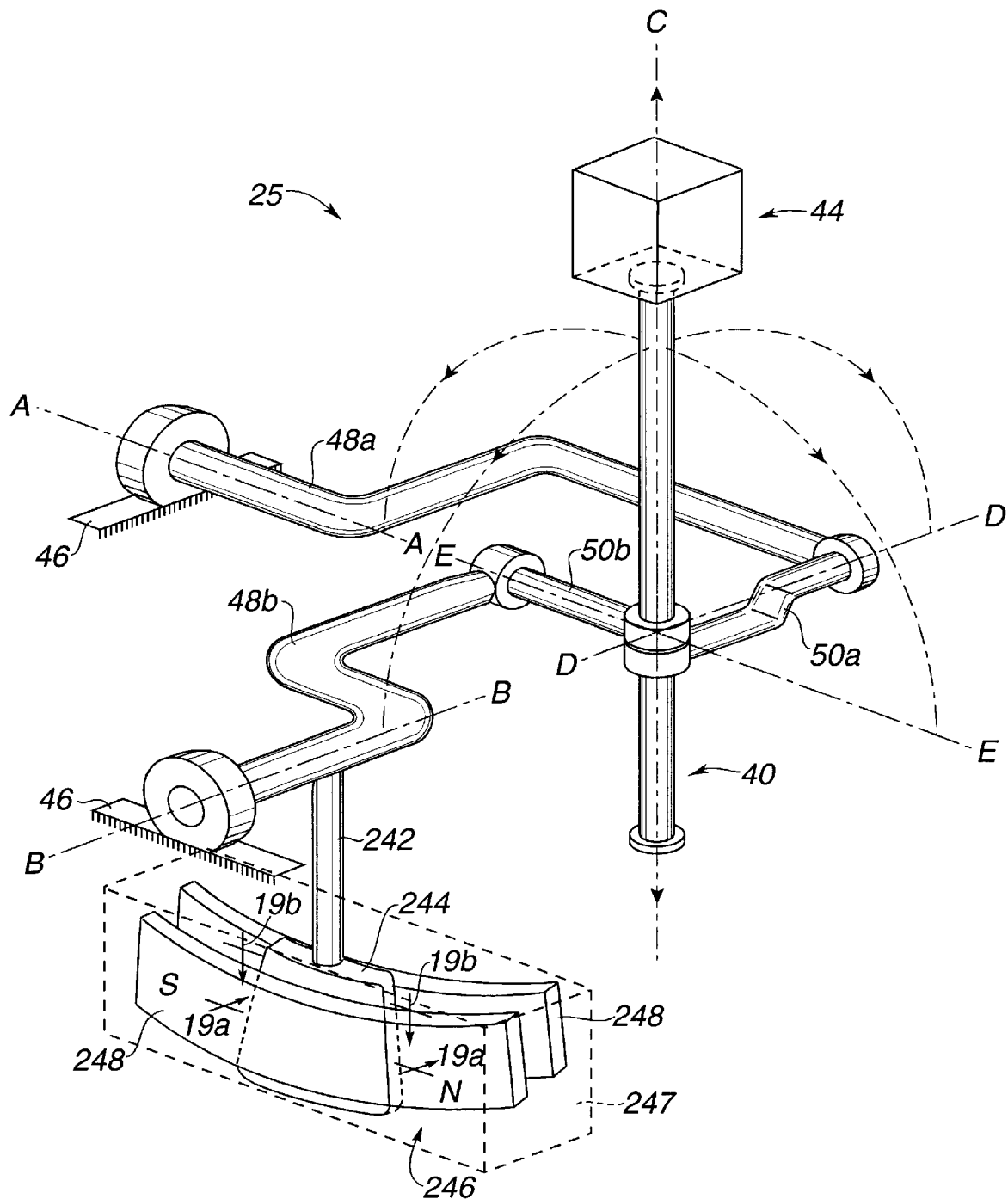
FIG. 18 is a perspective view of the mechanical apparatus of FIG. 2 including a voice coil actuator.

FIG. 18 is a perspective view of mechanical apparatus 25 (or 200) in which a voice coil actuator 240 acts as an actuator 126 to apply forces to object 44 in a degree of freedom. Voice coil actuators have been used in the prior art in a single degree of freedom for disk drives and similar rotating devices. Voice coil actuator 240 includes a pendulum shaft 242, a pendulum head 244, a magnetic assembly 246, and a magnetic flux guide 247. Pendulum shaft 242 is rigidly coupled to extension member 48a such that when extension member 48a rotates about axis B, pendulum shaft 242 also rotates about axis B. Pendulum head 244 is coupled to shaft 242 and rotates with the shaft. Pendulum head 244 is positioned between two magnets 248 of magnet guide 246. Preferably, pendulum head extends out from and is exposed partially on both sides of the magnet assembly 246.

Figure 19A:
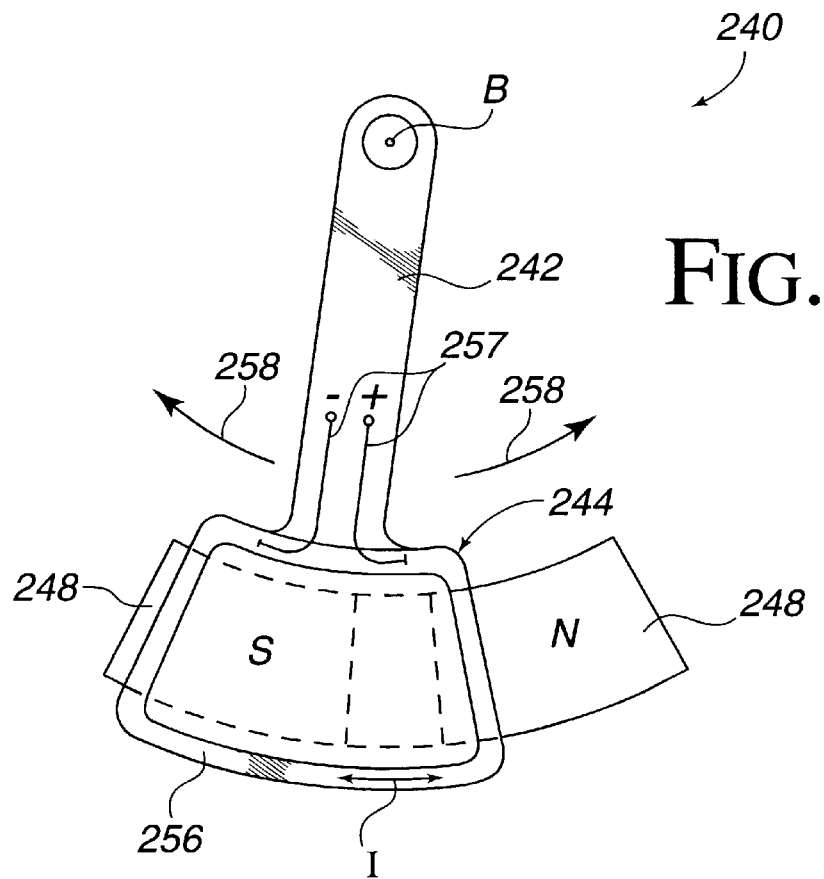
FIG. 19a is a side sectional view of the voice coil actuator of FIG. 18.
Figure 19B:
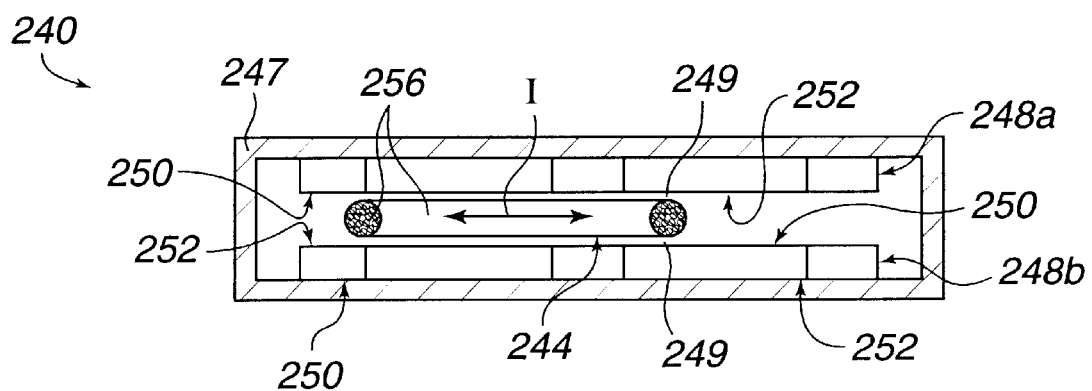

As shown in the side sectional view of FIG. 19a and the top sectional view of FIG. 19b, pendulum head 244 is positioned between magnets 248a and 248b and is thus affected by the magnetic fields of both magnets. Magnets 248a and 248b each include north polarity surfaces 250 and south polarity surfaces 252, thus providing four magnetic polarities to the interior region 255 of the guide 47 (opposite polarities are provided on opposing surfaces of magnets 248). In alternate embodiments, four different magnets can be provided (two north polarity magnets, and two south polarity magnets.) In yet another embodiment, one magnet 248a or 248b can be provided, and the other magnet can be a similarly-shaped piece of metal that provides a flux return path. Preferably, a small amount of space 249 is provided between the magnet surfaces and the pendulum head 244. Magnetic flux guide 247 is a housing that allows magnetic flux to travel from one end of the magnets 248 to the other end, as is well known to those skilled in the art.

Pendulum head 244 includes a coil of wire 256 which is preferably wound around the perimeter of the pendulum head. An electric current I is flowed through the coil 256 via electrical connections 257. As is well known to those skilled in the art, the electric current in the coil generates a magnetic field. The magnetic field from the coil then interacts with the magnetic fields generated by magnets 248 to produce a motion. The motion or torque of the pendulum head 244 is indicated by arrows 258. The magnitude or strength of the torque is dependent on the magnitude of the current that is applied to the coil. Likewise, the direction of the torque depends on the direction of the current to the coil. The operation and implementation of such pendulum movement from magnetic fields is well known to those skilled in the art.

Thus, by applied a desired current magnitude and direction, force can be applied to pendulum head 244, thereby applying force to pendulum shaft 242 and torque to extension member 48a. This in turn applies a force to object 44 in the rotary degree of freedom about axis B (and axis D). The voice coil actuator thus may be provided as a substitute for other actuators such as DC motors and brakes having rotatable shafts. A voice coil actuator can be provided for each degree of freedom of mechanical apparatus to which force is desired to be applied. For example, a second voice coil 240 is preferably coupled to extension member 48a in a similar manner to apply forces to object 44 in the rotary degree of freedom about axes A and E. In addition, the other embodiments of mechanical apparatus 25 as shown in FIGS. 12-17 can use the voice coil actuator 240 as an actuator. Also, other known mechanical interface devices, such as slotted yoke mechanisms or other gimbal mechanisms, can use voice coils to provide force feedback to a user of the interface in desired degrees of freedom.

In addition, the voice coil actuator 240 can be used as a sensor. A second coil, having an appropriate number of loops, can be placed on pendulum head 244. Motion about axis B within magnetic field induces a voltage across the second coil. The voltage can be sensed across this second coil. This voltage is proportional to the rotational velocity of the pendulum head 244. From this derived velocity, acceleration or position of the pendulum head can be derived using timing information, for example, from a clock (described below). Alternatively, the coil 256 can be used for both applying forces and sensing velocity, as is well known to those skilled in the art.

The voice coil actuator 240 has several advantages. One is that a limited angular range is defined for a particular degree of freedom of object 44 by the length of the magnetic assembly 246. In many interface devices, such as joysticks, such a limited angular range is desired to limit the movement of object 44. Also, the voice coil actuator provides good mechanical advantage due to the larger radius of the magnetic assembly 246. Thus, when using voice coil actuators for transducers 42, a capstan drive as described above with respect to FIG. 5, or friction drive as described below, are not necessary. Also, control of the voice coil actuator is simpler than other actuators since output torque is a linear function of input coil current. In addition, since voice coil actuators do not require mechanical or electrical commutation as do other types of motors, the voice coil actuator has a longer life expectancy, less maintenance, and quiet operation. The actuation is frictionless, resulting in greater haptic fidelity. Finally, the parts for voice coil actuators are inexpensive to produce and are readily available, resulting in a low cost way to provide realistic force feedback.

Alternatively, a linear voice coil can be used to provide forces in and detect motion in a linear degree of freedom. A linear voice coil has magnets similar to magnets 248 described above, except that they form a linear channel through which a coil head (similar to pendulum head 244) translates. Such a linear voice coil is described with reference to FIGS. 21*a*–*b* and 22*a*–*e* and can be used, for example, with the translating motion of linear axis member 40 or 204 and/or object 44 along axis C.

FIGS. 20*a*–20*e* are schematic views of an alternate embodiment 240' of a voice coil actuator for use in the present invention. Pendulum head 244' is an alteration of the pendulum head 244 of FIGS. 19*a* and 19*b*. Coil 260 is positioned around the perimeter of pendulum head 244' and includes multiple separate "sub-coils" of wire. Terminals 261 include a set of terminals for each different sub-coil in pendulum head 244'. These different sub-coils are shown in FIGS. 20*b*–20*e*.

Figure 20A:
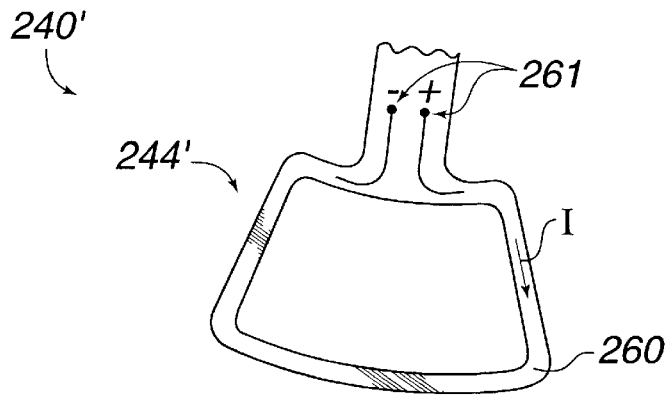
Figure 20B:
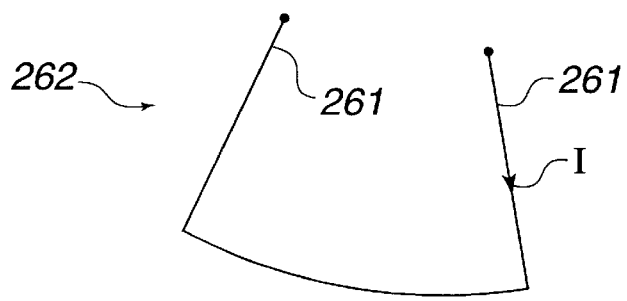
Figure 20C:
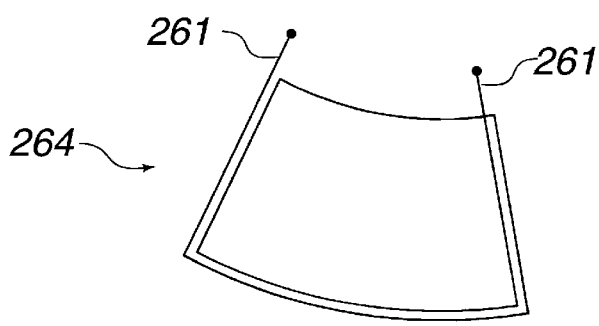
Figure 20D:
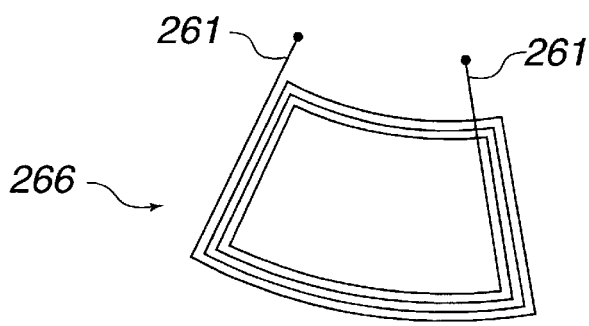
Figure 20E:
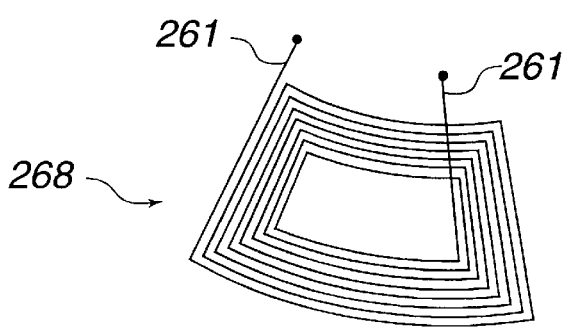

FIG. 20*b* shows one sub-coil 262 that forms one loop around the perimeter of head 244'. FIG. 20*c* shows a sub-coil 264 that forms two loops, and FIG. 20*d* shows a sub-coil 266 that forms four loops. Finally, FIG. 20*e* shows a sub-coil 268 that forms eight loops of wire. All of these sub-coils can be provided on pendulum 244' as coil 260. Each sub-coil shown in FIGS. 20*b*–20*e* includes its own set of terminals 261 to be connected to a source of current I.

Using, for example, the four different sub-coils shown in FIGS. 20*b*–20*e*, different magnetic fields can be induced for the pendulum head 244' and thus different torques can be applied to the pendulum. A fixed current can be selectively provided to each sub-coil using one or more switches connected to the sub-coils. Since the magnetic fields from selected sub-coils will interact to create larger or smaller magnetic fields, a variety of different torques can be provided. There are four different sub-coils, where each sub-coil produces a torque that is a factor of 2 greater than the previous coil. Thus, a total of $2^4=16$ different torques can be produced with a constant-magnitude current in each sub-coil. Since the direction of the current can be switched to create torques in the opposite direction, the total number of torques that can be produced is equal to 31. In other embodiments, a different number of sub-coils can be used. Reduced to a general rule, a voice coil actuator having N sub-coils, each of which can be driven in one of three states (positive polarity, 0, negative polarity) can produce $2^{N+1}-1$ torque values.

This scheme is readily applicable to a digital system using on and off switches. For example, each sub-coil can be provided with a set of four switches (commonly referred to as an "H-bridge") to select the direction of the current in the sub-coil. An advantage of this alternate embodiment is that the current magnitudes need not be varied, allowing for less complex electronics and a scheme easily adaptable to digital signals.

In other embodiments, additional sets of coils can be provided to create additional torque values. For example, another set of four sub-coils, identical to the set described above, can be added to coil 260 and oriented so that the second set of sub-coils creates torques in the opposite direction to the first set. With additional coils, the number of switches can be reduced. In yet other embodiments, the coils can be provided as traces on a printed circuit board for easy manufacture.

Figure 21A:
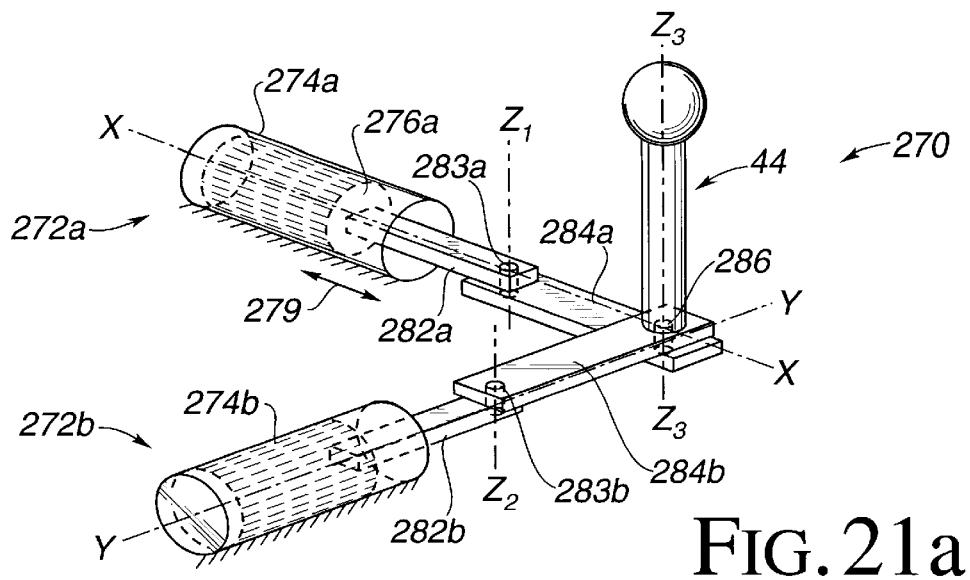
FIG. 21a is a perspective view of an interface apparatus of the present invention including linear voice coil actuators.

FIG. 21*a* is a perspective view of an interface system 270 in which two linear degrees of freedom are provided to user object 44 and linear voice coil actuators 272*a* and 272*b* are used to apply forces to the user object. Computer 16 (not shown) is preferably coupled to the voice coil actuators to apply current as desired.

Figure 21B:
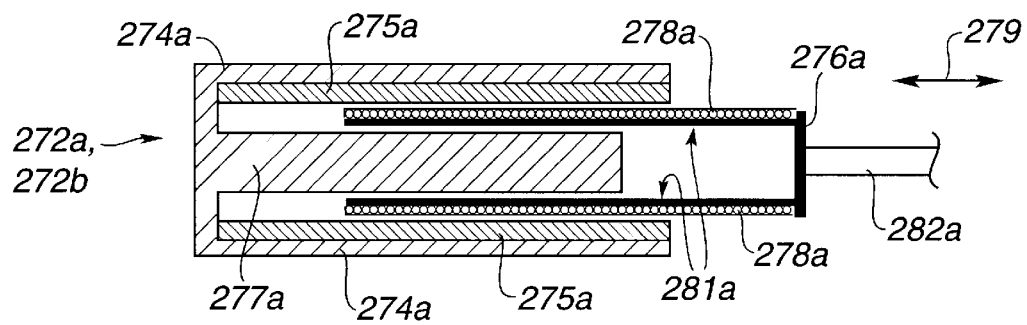

A side sectional view of an example of a linear voice coil actuator 272*a* is shown in FIG. 21*b*. Linear voice coil actuator 272*a* is a grounded actuator and include a cylindrical magnetic flux housing 274*a* and a coil head 276*a*. Housing 274*a* can be made of iron or other ferrous metal and includes a radially polarized, tubular magnet 275*a* (which, alternatively, can be made up of multiple, smaller magnets) positioned along the inside length of the housing and which are radially magnetized. In addition, a core portion 277*a* of housing 274*a* preferably extends down the center of housing 274*a* through the center of coil head 276*a*. Coil head 276*a* includes a coil 278*a* which is wrapped around the coil head, similar to the coil 256 of FIG. 19*a*. An optional coil support 281 a can be provided around which to wrap coil 278*a*. The coil head 276*a* moves within the housing 274*a* along a linear degree of freedom, indicated by arrows 279, when a current is flowed through coil 278*a*, similarly as described above. The direction of the coil head 276*a* depends on the direction of the applied current. In addition, the linear voice coil actuator can be used to sense the position of coil head 276*a* along the linear degree of freedom by sensing velocity as described above with reference to FIG. 19*a* and 19*b*. Alternately, separate linear motion sensors can be coupled to the object 44 or other members; such linear sensors are well known to those skilled in the art. In other embodiments, the coil head 276*a* can be made longer than the housing 274*a*. Linear voice coil actuators are well known to those skilled in the art and are described in *Precision Machine Design*, by Alexander Slocum, Prentice Hall, 1992, page 64.

Referring back to FIG. 21*a*, coil head 276*a* is preferably coupled to a first end of a shaft 282*a*, and a second end of shaft 282*a* is coupled to a first end of a joint member 284*a*. A rotary joint 283*a* couples shaft 282*a* to joint member 284*a* and allows joint member 284*a* to rotate about floating axis $Z_1$. A second end of joint member 284*a* is rotatably coupled to a second end of joint member 284*b* by a rotary joint 286. User object 44 is preferably coupled to joint member 284*b* (or, alternatively, 284*a*). Linear voice coil actuator 272*b* has equivalent components to actuator 272*a* as shown in FIG. 21*b*. Joint member 284*b* can thus rotate about floating axis $Z_2$. The second end of joint member 284*b* is rotatably coupled to the second end of joint member 284*a* by rotary joint 286, which provides an axis of rotation $Z_3$.

Object 44 can be translated by a user along linear axis X or linear axis Y, or along a combination of these axes. When object 44 is moved along axis X toward or away from housing 274a, then coil head 276a, shaft 282a, and joint member 284a are correspondingly moved toward or away from housing 274a and retain the same relative position as shown in FIG. 21a. However, joint member 284b rotates about floating axis $Z_2$ and floating axis $Z_3$ in accordance with the movement of joint member 284a. Likewise, when object 44 is moved along axis Y toward or away from housing 272b, then coil head 276b, shaft 282b, and joint member 284b are correspondingly moved toward or away from housing 272b and retain the relative positions as shown in FIG. 21a. Joint member 284a rotates about floating axes $Z_1$ and $Z_3$ in accordance with the movement of joint member 284b. When object 44 is moved simultaneously along both axes X and Y (e.g., object 44 is moved diagonally), then both joint members 284a and 284b rotate about their respective axes and axis $Z_3$.

Shafts 282a and 282b and joint members 284a and 284b can be rectilinear members that may be rotatably coupled to each other at flat surfaces of the members with rotary couplings or hinges 283a, 283b, and 286. In the described embodiment, one joint member 284a is coupled under shaft 282a and the other joint member 284b is coupled over shaft 282b. Alternatively, the shafts and joint members can be coupled together in many different configurations.

Figure 21C:
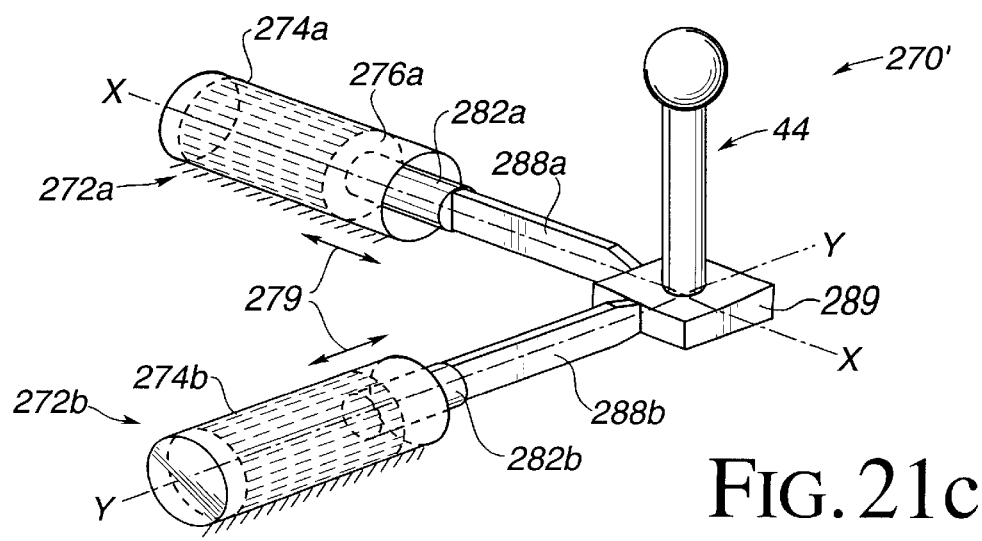

FIG. 21c is a schematic diagram of an alternate embodiment 270' of the interface system 270 shown in FIG. 21a. In FIG. 21c, two linear voice coil actuators 272a and 272b as shown in FIG. 21a are included to apply forces and sense positions in two linear degrees of freedom to object 44. Voice coil actuator 272a includes housing 274a, coil head 276a, and shaft 282a, and actuator 272b includes equivalent components. Computer 16 (not shown) is preferably coupled to the voice coil actuators to apply current as desired.

As in FIG. 21a, coil heads 276a and 276b translate along linear degrees of freedom, indicated by arrows 279, within housings 274a and 274b, respectively. Current can be applied by computer 16 to apply force to the coil heads or sense velocity.

Shaft 282a is coupled to a flexible member 288a. Flexible members 288a and 288b are preferably made of a resilient material such as flexible plastic, rubber, metal, or the like and can flex similarly to the flexible members described above with respect to FIG. 12. As described above, flexible members 288a and 288b are preferably narrow in the dimension that the rod is to bend, and wide in the dimensions in which the rod is to remain rigid. Shaft 282a is a rigid member that couples member 288a to coil head 276a, and can be provided with different lengths in different embodiments. Flexible member 288a is rigidly coupled to an object member 289 at the other end of the flexible member. Member 289 can be a part of object 44 or a platform or other base for supporting object 44. Shaft 282b is coupled to object 44 through flexible member 288b in a similar manner. Flexible member 288b is coupled to object member 289 at its other end.

Object 44 can be moved by a user along linear axis X or linear axis Y. Flexible members 288a and 288b flex (bend) appropriately as the object is moved. For example, if object 44 and member 289 are moved along axis X, flexible member 288a does not bend since the direction of movement is directed down (substantially parallel to) the longitudinal axis of flexible member 288a. However, since housing 274b is grounded and fixed in place relative to object 44, flexible member 288a bends toward or away from actuator 272a (depending on the object's direction along axis X) to allow the translation of object 44. This occurs when the direction of movement of object 44 is substantially perpendicular to the longitudinal axis of flexible member 288a. Likewise, when object 44 is translated along axis Y in the other linear degree of freedom, flexible member 288b does not flex since the direction of movement is directed substantially parallel to the longitudinal axis of flexible member 288b. Flexible member 288a, however, bends toward or away from actuator 272b to allow the translation of object 44. When object 44 is moved simultaneously along both axes X and Y (e.g., object 44 is moved diagonally), then both flexible members 288a and 288b flex in conjunction with the movement. It should be noted that the flexible members 288a and 288b do not need to twist (i.e. provide torsion flex) like the flexible members of FIG. 12. Only a bending motion is required of members 288a and 288b in the embodiment of FIG. 21c.

FIG. 22a is a top plan view and FIG. 22b is a side elevational view of an interface apparatus 300 including voice coil actuators similar to those described above with reference to FIGS. 18, 19a, and 19b. Interface apparatus 300 includes user object 44, a ball joint 302, a socket 304, a drive pin 306, a circuit board 308, and voice coil actuators 310a and 310b. User object 44 is shown as a joystick that is coupled to ball joint 302. User object 44 has two rotary degrees of freedom about axis X and axis Y, respectively, as indicated by arrows 312 and 314. These degrees of freedom result from ball joint 302 rotating within socket 304. Socket 304 is grounded and remains stationary relative to user object 44, ball joint 302, and the other moving components of apparatus 300. Ball socket 302 is shown as a partial sphere with a portion of the sphere cut off. Other similar types of joints can be used in other embodiments.

Drive pin 306 is coupled to ball joint 302 and extends along an axis Z out of the plane defined by axes X and Y. Drive pin 306 extends through an aperture 316 in a circuit board 308. Preferably, a grommet 322 made of rubber or a similar compliant material is positioned between the drive pin 306 and the circuit board 308. Alternatively, open space can be provided between the pin and the board. Circuit board 308 is positioned in a plane substantially parallel to the X-Y plane and floats, i.e., circuit board 308 is not grounded. Board 308 is preferably guided by guides 318, which serve to keep circuit board 308 substantially within the plane parallel to the X-Y plane and allow the circuit board to translate in that plane, as shown by arrows 320. Guides 318 are shown as round, cylindrical members, but have a variety of shapes in alternate embodiments. In this embodiment, circuit board 308 translates in linear degrees of freedom, while user object 44 rotates in rotary degrees of freedom.

Circuit board 308 is provided in a substantially right-angle orientation having one extended portion 324 at 90 degrees from the other extended portion 324b. In alternate embodiments, circuit board 308 can be provided as other shapes. Voice coil actuators 310a and 310b are positioned on circuit board 308 such that one actuator 310a is provided on portion 324a and the other actuator is provided on portion 324b. Wire coil 326a of actuator 310a is coupled to portion 324a of circuit board 308. Preferably, wire coil 324a includes at least two loops and is etched onto board 308 as a printed circuit board trace using well-known techniques. Terminals 328a are coupled to actuator drivers of actuator interface 414, as described below, so that computer 16 (or microprocessor 410) can control the direction and/or magnitude of the current in wire coil 326a. In alternate embodiments, additional coils can be provided on portion 324a for sensing velocity and/or implementing the alternate embodiment of FIGS. 20a–20e.

Voice coil actuator 310a also includes a magnet assembly 330a, which preferably includes four magnets 332 and is grounded. Alternatively, two magnets with two polarities each can be included. Each magnet has a north polarity N and a south polarity S on opposing sides of the magnet. Opposite polarities of magnets 332 face each other such that coil 326a is positioned between opposing polarities on either side of the coil. The magnetic fields from magnets 332 interact with the magnetic field produced from wire coil 326a when current is flowed in coil 326a similarly as described above with reference to FIGS. 19a and 19b to produce a linear force to circuit board 308 in a direction parallel to axis Y, as shown by arrow 320a. The circuit board 308 and wire coil 326a are moved parallel to axis Y until coil 326a is moved out from under the magnet 332 on the side where the coil was moved. For example, circuit board 308 can be moved to the limits shown by dotted lines 334. Alternatively, physical stops can be positioned at the edges of the board 308 to provide this movement limit. When circuit board 308 translates along axis Y due to forces generated by voice coil actuator 310a, drive pin 306 is also moved through contact with board 308 (and grommet 322). This, in turn, rotates ball joint 302 within socket 304 and moves user object 44 so that the user feels the forces in the rotary degree of freedom about axis X, as shown by arrows 312. The movement of user object 44 can be limited by stops positioned outside the edge of circuit board 308 and/or by stops placed on ball joint 302 to limit the movement of object 44.

Voice coil actuator 310a can also be used, as described in above embodiments, to sense the velocity of circuit board 308 along axis Y as the user moves user object 44 about axis X and to derive position and other values from that velocity. However, since the voice coil actuators produce analog sensor values, subject to noise, and the filtering of such noise typically requires expensive components, it is preferred that separate digital sensors be used to sense the position, motion, etc. of object 44 for low cost interface devices. For example, a lateral effect photo diode sensor 338 can be used. Sensor 338 can include a rectangular detector 340 positioned in a plane parallel to the X-Y plane onto which a beam of energy 342 is emitted from a grounded emitter 344. The position of the circuit board 308, and thus the position of object 44, can be determined by the location of the beam 342 on the detector. Alternatively, other types of sensors can be used, such as an optical encoder having a rotating shaft coupled to a roller that is frictionally engaged with circuit board 308.

Voice coil actuator 310b operates similarly to actuator 310a. A current is flowed through coil 326b to induce magnetic forces that translate circuit board 308 in a direction parallel to axis X, as shown by arrow 320b. This moves drive pin 306 and causes forces to be applied to user object 44 in the rotary degree of freedom about axis Y, as shown by arrows 314. A separate sensor can also be provided for the motion of object 44 about axis Y, or a single sensor 338 can be used to detect motion in both degrees of freedom.

Figure 22C:
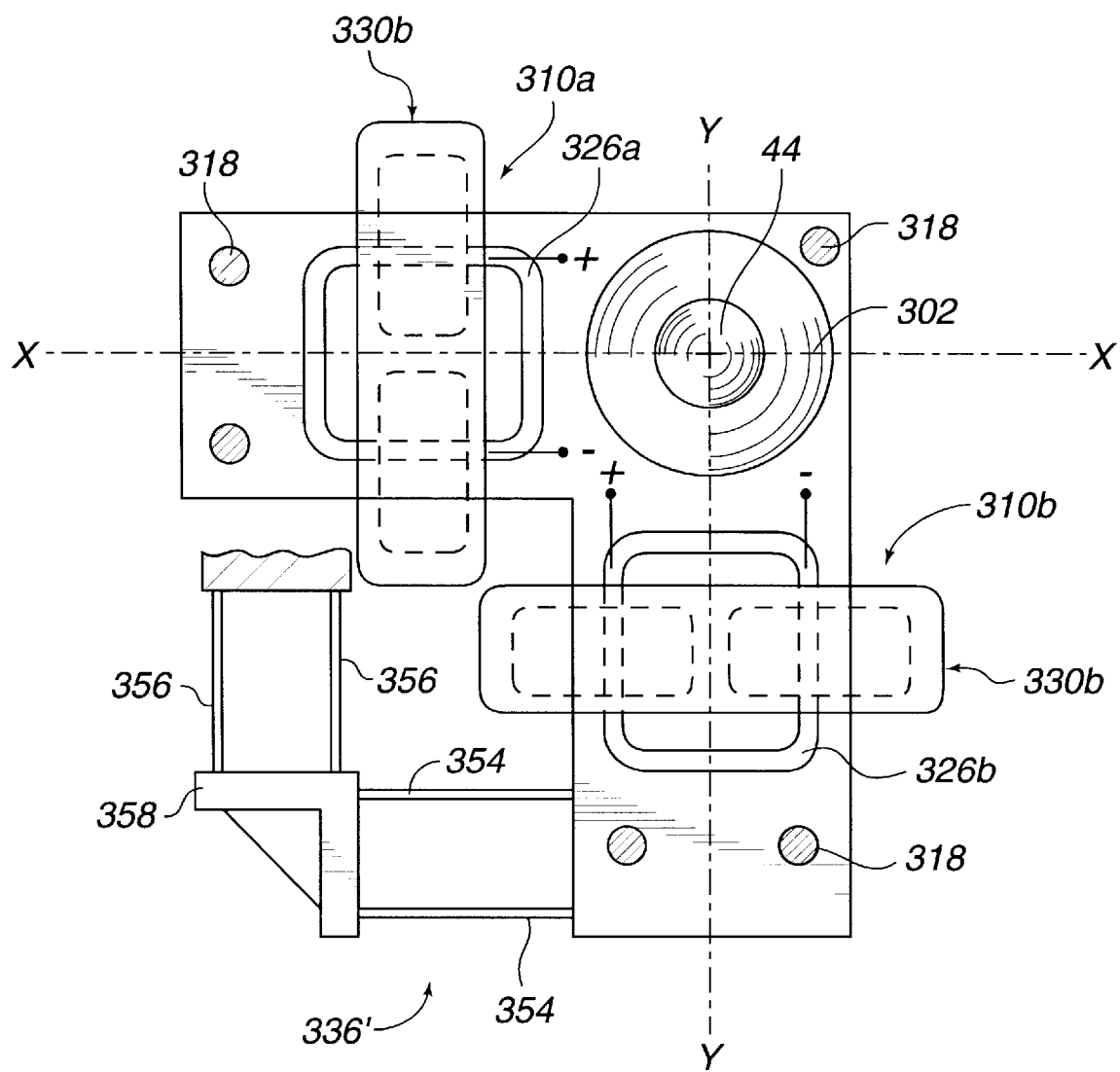
FIG. 22c is a top plan view of an alternate embodiment of the interface apparatus of FIG. 22a using a different anti-rotation flexure.

Optionally, an anti-rotation flexure 336 can be coupled between a grounded surface and circuit board 308. This flexure 336 preferably prevents board 308 from rotating about axis Z in the plane parallel to the X-Y plane. In addition, flexure 336 can provide a restoring force through circuit board 308 to object 44 to bring the object back to a center position as shown in FIG. 22b when no other forces are being applied to the object. Flexure 336 can be a helical spring-like member (as shown), an Oldham style shaft coupling (allowing slotted movement), or a flexure assembly similar to the one shown in FIG. 22c. The flexure can take other forms in other embodiments.

The embodiment of FIGS. 22a and 22b has several advantages. One is that the coils 326a and 326b can be etched directly onto circuit board 308, thus avoiding assembly time in wrapping a separate wire. In addition, the preferred voice coil driver chips (described with reference to FIG. 24), as well as other electronic components of interface 14 or 14', can be coupled directly to circuit board 308 and interconnected with traces on board 308. This provides a simple and low cost method to manufacture and provide the electronic components of the interface apparatus.

FIG. 22c is a top plan view of an alternate embodiment of the interface apparatus 300 shown in FIG. 22a, in which a different anti-rotation flexure 336' is used instead of the helical flexure 336 shown in FIG. 22b. Anti-rotation flexure 336' includes flexible members 354 oriented in the direction of axis X, flexible members 356 oriented in the direction of axis Y, and a rigid L-shaped member 358. Members 354 are coupled to circuit board 308 on one end and to L-shaped member 358 on the other end. Members 356 are coupled to L-shaped member 358 on one end and to ground on the other end. Members 354 and 356 can be narrow in one dimension and relatively wide in the other dimensions, similar to flexible members 212a and 212b shown in FIG. 12, so that the members can bend within the X-Y plane.

The flexure 336' allows the circuit board 308 to move along the axes X and Y, but prevents the circuit board 308 from rotating within the X-Y plane. Flexure 336' is more complex to implement than the helical flexure 336, but provides less resistance to the circuit board's motion along the X and Y axes and thus allows more accurate force feedback.

FIGS. 22d and 22e show an alternate embodiment 300' of the interface apparatus 300 shown in FIGS. 22a and 22b. Interface apparatus 300' provides two linear degrees of freedom to object 44 so that the user can translate object 44 along the X axis, along the Y axis, or along both axes (diagonal movement). Apparatus 300' includes a circuit board 308 that includes voice coil actuators 310a and 310b and guides 318. These components operate substantially similar to the equivalent components in apparatus 300.

A main difference between the embodiments of FIGS. 22a–b and FIGS. 22d–e is that object 44 is rigidly coupled to circuit board 308. Thus, when circuit board 308 is translated along axis X and/or axis Y, shown by arrows 320a and 320b, object 44 is translated in the same directions, as shown by arrows 350 and 352, respectively, providing the object with linear degrees of freedom. Thus, both user object 44 and circuit board 308 move in linear degrees of freedom. This is unlike the apparatus 300, in which the linear motion of circuit board 308 was converted into rotary degrees of freedom for object 44 by ball joint 302.

Figure 23A:
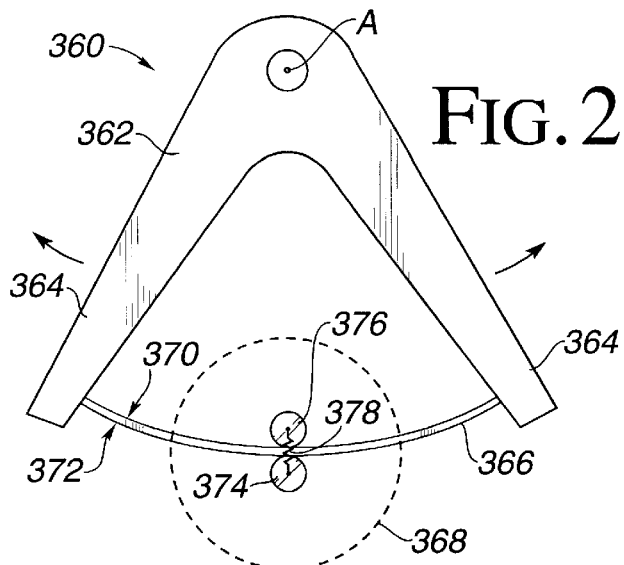
FIGS. 23a to 23f are side elevational views of a friction drive of the present invention suitable for use with the interface apparatus of the present invention.

FIG. 23a is a front elevational view of an embodiment for a friction drive 360 that can be used, for example, in place of capstan drive mechanism 58 of the present invention. Drum 162 is similar to capstan drum 59 and can be coupled to mechanical apparatus 25 or 200 similarly as described above. For example, drum 362 can be rigidly coupled to extension member 48a or 48b and can rotate about axis A or axis B, respectively. Axis A is shown in FIG. 23a as an example.

Leg portions 364 of drum 362 are provided in a similar configuration as capstan drum 59. A drive bar 366 is coupled between the leg portions 364. Drive bar 366 is a curved, preferably round, rigid wire that has an interior frictional surface 370 and an exterior frictional surface 372. Alternatively, drive bar can be a flat or square-cross sectional member and/or can be either rigid or flexible. A drive roller 374 is frictionally engaged with the external frictional surface 372 and is rotatably coupled to a ground member. For example, drive roller 374 can be coupled to ground member 62 of apparatus 25 similarly to pully 76 as shown in FIG. 5. Drive roller 374 is preferably coupled to a shaft of a transducer 42, similarly to pulley 76 of FIG. 5. Preferably, transducer 42 includes an actuator that rotates driver roller 374.

A passive roller 376 is frictionally engaged with the interior frictional surface 370 of drive bar 366 opposite to drive roller 374 and extends substantially parallel to the drive roller. Passive roller 376 is preferably spring loaded such that the passive roller is forced towards driver roller 374. This force is indicated by spring 378. For example, spring members can couple the passive roller to driver roller 374. A clamping force is thus created between the passive roller 376 and the drive roller 374, which creates a high compressive force between the drive bar 366 and the drive roller 374. This force enables the drive roller to impart a tangential driving force to the drive bar 366 and thus move the drive bar, in turn rotating drum 362 about axis A. Using the friction drive 360, an actuator in transducer 42 can impart rotary forces to drum 362 and, for example, extension member 48a or 48b. In addition, a sensor in transducer 42 can sense the position of an extension member 48a or 48b by reading the position of drum 60. The motion of drum 60 is transmitted to drive roller 374 through the compressive force, and is read by the sensor as the drive roller rotates.

In alternate embodiments, passive roller 376 can be rotatably coupled to ground member 62 and thus fixed in position. In addition, the spring members can be placed between a moveable or compliant passive roller and ground and between a moveable/compliant drive roller 374 and ground in an alternate embodiment. This would allow the passive roller and the drive roller to both be pulled against the drive bar 366.

The friction drive 360 has several advantages. A mechanical advantage is provided between an actuator and the rotation of object 44, as explained above for capstan drive mechanism 58. In addition, as explained above for the capstan drive, substantially no backlash is created with the friction drive and the friction drive operates very smoothly to provide realistic forces to the user. However, no cable or wire is required in the present drive mechanism, thus providing a simpler and easier to assemble drive mechanism than the capstan drive. The friction drive is also inexpensive, since the parts of the drive are simple to manufacture. Also, high speed-reduction ratios between the actuator coupled to drive roller 374 and the motion of drum 362 about axis A are possible when, for example, a small drive roller 374 drives a drive bar 366 having a large operating radius.

Figure 23B:
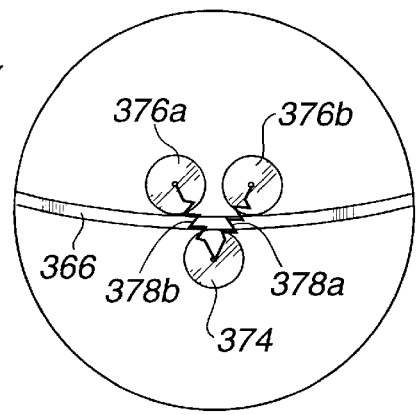

FIG. 23b is a detailed view (defined by dotted line 368 of FIG. 23a) of a different embodiment of the rollers and drive bar of the friction drive 360. In this embodiment, two passive rollers 376a and 376b are provided to be frictionally engaged with the interior surface 370 of drive bar 366. Each passive roller 376a and 376b is spring loaded to drive roller 374 by spring members 378a and 378b, respectively. The two passive rollers 376a and 376b provide a greater clamping force and compressive force between the drive and passive rollers, thus preventing more slip of drive bar 366 than the embodiment of FIG. 23a.

Figure 23C:
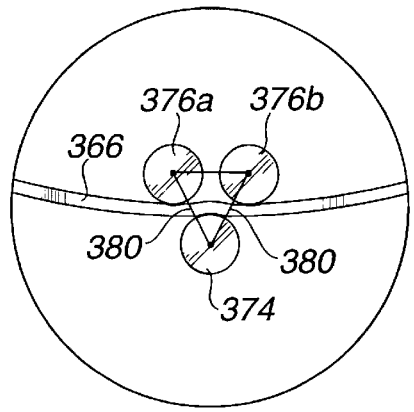

FIG. 23c is a detailed view of a third embodiment of the rollers and drive bar of the friction drive 360. Drive bar 366 is preferably round or square wire that is flexible in at least one direction. Two passive rollers 376a and 376b can be coupled together and to drive roller 374 by non-tensile connections 380. The flexibility in drive bar 366 allows the drive bar to bend around the rollers and creates a higher friction, thus preventing slippage of the drive bar.

Figure 23D:
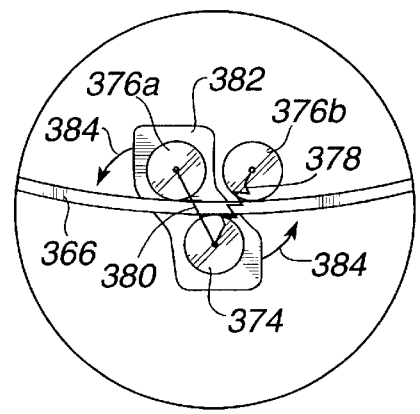

FIG. 23d is a detailed view of a fourth embodiment of the rollers and driver bar which is similar to the embodiment shown in FIG. 23b except that one of the passive rollers 376a and 376b is not spring loaded. Preferably, passive roller 376a (or 376b) is coupled to drive roller 374 by a rotatable plate 382 or other rigid member, which acts as the non-compliant connection 380. Since the spring 378 forces the drive roller 374 toward drive bar 366, the plate 382 rotates as shown by arrows 384. This forces the passive roller 376a against drive bar 366 and thus increases the compression force between the rollers and the drive bar 366.

Figure 23E:
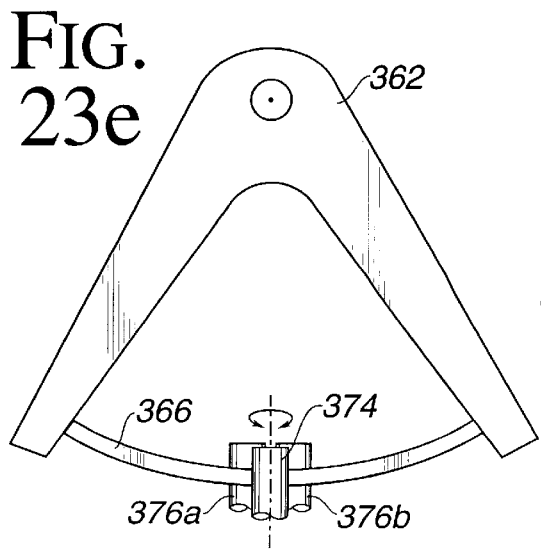

FIG. 23e is an alternate embodiment of the friction drive 360 in which the rollers 376a, 376b, and 374 are provided in a different orientation. The rollers are positioned 90 degrees offset from their position in the embodiment of FIG. 23a. The function of the rollers is substantially the same as described above.

Figure 23F:
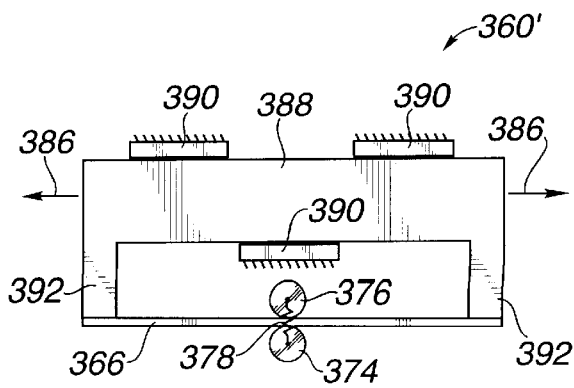

FIG. 23f is an alternative embodiment showing a linear friction drive 360'. Friction drive 360' includes a sliding member 388 which is supported by guides 390. Guides 390 are preferably grounded so that sliding member 388 can translate between the guides, as shown by arrows 386. A drive bar 366 is coupled between two leg portions 392 of the sliding member 388. Drive bar 366 can be a wire or member as described above with respect to FIG. 23a.

Passive roller 376 and drive roller 374 are frictionally engaged with drive bar 366. As described above, drive roller 374 is rotated by an actuator and causes a tangential force on drive bar 366. This causes sliding member 388 to translate in either direction 386. A spring 378 can be coupled between the passive and drive rollers as described above. Alternatively, the other embodiments of rollers 374 and 376 as described with reference to FIGS. 23b–23e can also be used with linear friction drive 360'. Linear friction drive 360' can be used to provide forces in a linear degree of freedom. For example, linear forces can be applied to linear axis member 40 or 204 (or object 44, if appropriate) using drive 360'. The linear axis member can be coupled to sliding member 388 and thus translate when member 388 translates.

Figure 24:
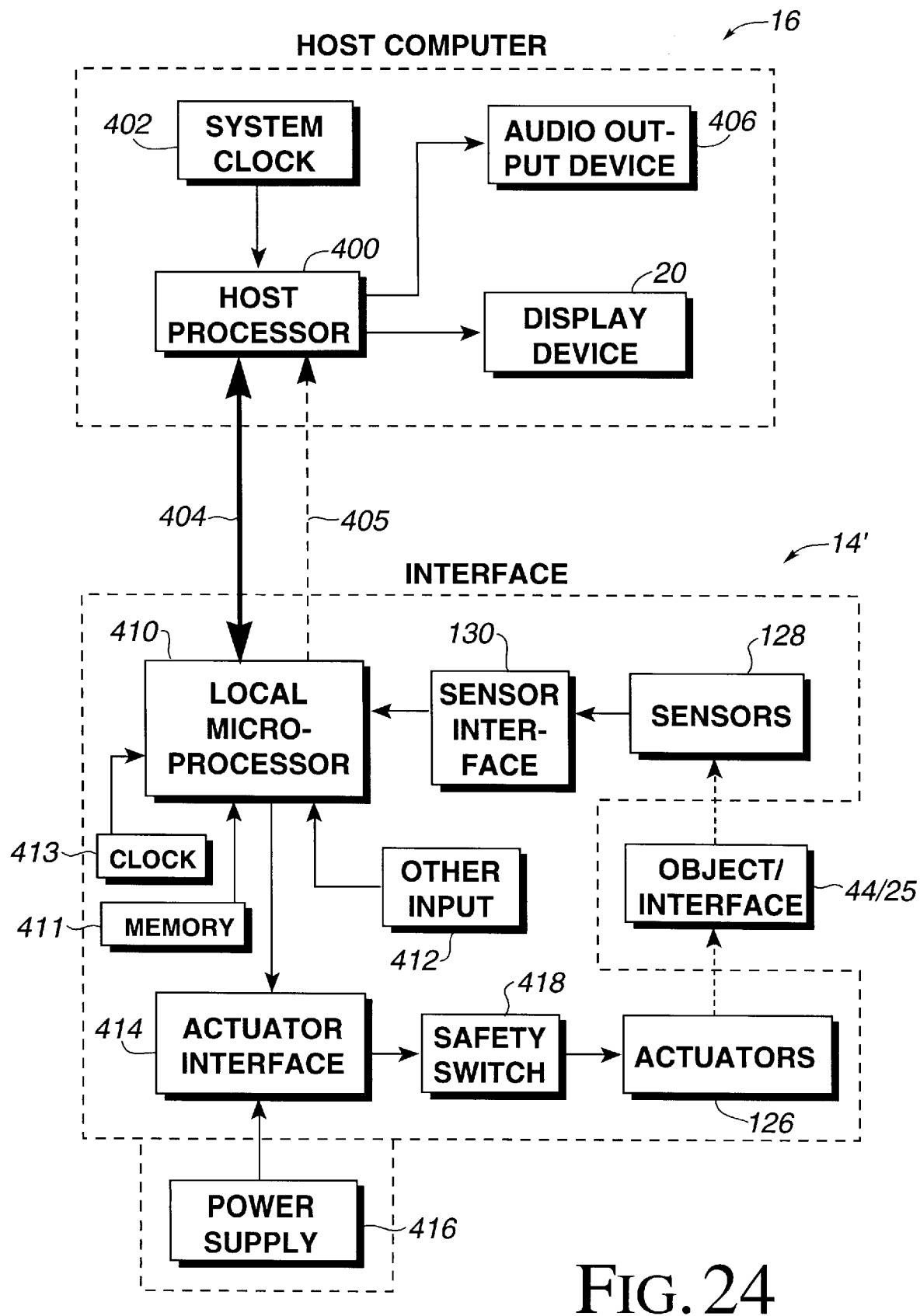
FIG. 24 is a block diagram of a host computer and an alternative embodiment of the electronic interface between the computer and an interface apparatus of the present invention.

FIG. 24 is a block diagram showing another embodiment of an electronic interface 14' and host computer 16 suitable for use with the present invention. This embodiment includes a local microprocessor which can perform much of the signal processing necessary to control the sensors and actuators of the mechanical apparatus 25. User object 44 may be grasped or otherwise contacted or controlled by a user and is coupled to mechanical apparatus 25, as described above.

Host computer 16 preferably includes a host microprocessor 400, a clock 402, and display screen 20. Host microprocessor 400 can include a variety of available microprocessors from Intel, Motorola, or other manufacturers. Microprocessor 400 can be single microprocessor chip, or can include multiple primary and/or co-processors. In addition, host computer 16 preferably includes standard components such as random access memory (RAM), read-only memory (ROM), and input/output (I/O) electronics (not shown). In the described embodiment, host computer system 16 can receive sensor data or a sensor signal via interface 404 from sensors of mechanical apparatus 25 and other information. Host computer 16 can also output a "force command" to mechanical apparatus 25 via interface 404 to cause force feedback for the interface device.

Clock 402 is a standard clock crystal or equivalent component used by host computer 16 to provide timing to electrical signals used by microprocessor 400 and other components of the computer. Clock 402 can be accessed by host computer 16 in the control process of the present invention, as described subsequently.

Display screen 20 is described with reference to FIG. 1. Audio output device 406, such as speakers, is preferably coupled to host microprocessor 400 via amplifiers, filters, and other circuitry well known to those skilled in the art. Host processor outputs signals to speakers 406 to provide sound output to the user when a "audio event" occurs during the implementation of the host application program. Other types of peripherals can also be coupled to host processor 400, such as storage devices (hard disk drive, CD ROM drive, floppy disk drive, etc.), printers, and other input and output devices.

Electronic interface 14' is coupled to host computer 16 by a bi-directional bus 404. The bi-directional bus sends signals in either direction between host computer 16 and interface 14'. Herein, the term "bus" is intended to generically refer to an interface such as between host computer 16 and microprocessor 410 which typically includes one or more connecting wires or other connections and that can be implemented in a variety of ways, as described below. In the preferred embodiment, bus 404 is a serial interface bus providing data according to a serial communication protocol. An interface port of host computer 16, such as an RS232 serial interface port, connects bus 404 to host computer 16. Other standard serial communication protocols can also be used in the serial interface and bus 404, such as RS-422, Universal Serial Bus (USB), MIDI, IrDA, or other protocols well known to those skilled in the art. For example, USB provides a relatively high speed serial interface that can provide force feedback signals in the present invention with a high degree of realism.

An advantage of the present embodiment 14' is that low-bandwidth serial communication signals can be used to interface with mechanical apparatus 25, thus allowing a standard built-in serial interface of many computers to be used directly. Alternatively, a parallel port of host computer 16 can be coupled to a parallel bus 404 and communicate with interface device using a parallel protocol, such as SCSI or PC Parallel Printer Bus. In a different embodiment, as described with reference to FIG. 9, bus 404 can be connected directly to a data bus of host computer 16 using, for example, a plug-in card and slot or other access of computer 16. For example, on an IBM AT compatible computer, the interface card can be implemented as an ISA, EISA, VESA local bus, PCI, or other well-known standard interface card which plugs into the motherboard of the computer and provides input and output ports connected to the main data bus of the computer. In addition, the embodiment of FIG. 9 can be used with the local microprocessor of the present embodiment.

In yet another embodiment, an additional bus 405 can be included to communicate between host computer 16 and electronic interface 14'. Since the speed requirement for communication signals is relatively high for outputting force feedback signals, the single serial interface used with bus 404 may not provide signals to and from the interface device at a high enough rate to achieve realistic force feedback. In such an embodiment, bus 404 can be coupled to the standard serial port of host computer 16, while additional bus 405 can be coupled to a second port of the host computer. For example, many computer systems include a "game port" in addition to a serial RS232 port to connect a joystick or similar game controller to the computer. The two buses 404 and 405 can be used simultaneously to provide an increased data bandwidth. For example, microprocessor 410 can send sensor signals to host computer 16 via a uni-directional bus 405 and a game port, while host computer 16 can output force feedback signals from a serial port to microprocessor 410 via uni-directional bus 404. Other combinations of data flow configurations can be implemented in other embodiments.

Electronic interface 14' includes a local microprocessor 410, sensors 128, actuators 126, optional sensor interface 130, an optional actuator interface 412, and other optional input devices 414. Interface 14' may also include additional electronic components for communicating via standard protocols on bus 404. In the preferred embodiment, multiple mechanical apparatuses 25 and interfaces 14' can be coupled to a single host computer 16 through bus 404 (or multiple buses 404) so that multiple users can simultaneously interface with the host application program (in a multi-player game or simulation, for example). In addition, multiple players can interact in the host application program with multiple mechanical apparatuses 25/interfaces 14' using networked host computers 16, as is well known to those skilled in the art.

Local microprocessor 410 is coupled to bus 404 and is preferably included within the housing of interface 14' (and mechanical interface apparatus 25) to allow quick communication with other components of the interface device. Processor 410 is considered "local" to mechanical apparatus 25 and interface 14', where "local" herein refers to processor 410 being a separate microprocessor from any processors in host computer 16. "Local" also preferably refers to processor 410 being dedicated to force feedback and sensor I/O of mechanical apparatus 25, and being closely coupled to sensors 128 and actuators 126, such as within or coupled closely to the housing for the mechanical apparatus 25. Microprocessor 410 can be provided with software instructions to wait for commands or requests from computer 16, decode the command or request, and handle/control input and output signals according to the command or request. In addition, processor 410 preferably operates independent of host computer 16 by reading sensor signals and calculating appropriate forces from those sensor signals, time signals, and a subroutine or "reflex process" selected in accordance with a host command. Suitable microprocessors for use as local microprocessor 410 include the MC68HC711E9 by Motorola and the PIC16C74 by Microchip, for example. Microprocessor 410 can include one microprocessor chip, or multiple processors and/or co-processor chips. In other embodiments, microprocessor 410 can include a digital signal processor (DSP) chip. Local memory 411, such as RAM and/or ROM, is preferably coupled to microprocessor 410 in interface 14' to store instructions for microprocessor 410 and store temporary data. In addition, a local clock 413 can be coupled to the microprocessor to provide absolute timing information, similar to system clock 402 of host computer 16; the timing information might be required, for example, to compute forces output by actuators 126 (e.g., forces dependent on calculated velocities or other time dependent factors). Microprocessor 410 can receive signals from sensors 128 and provide signals to actuators 126 of the interface 14' in accordance with instructions provided by host computer 16 over bus 404.

For example, in one embodiment, host computer 16 can provide low-level force commands over bus 404, which microprocessor 410 directly provides to actuators 126. In a different embodiment, host computer 16 can provide high level supervisory commands to microprocessor 410 over bus 404, and microprocessor 410 manages low level force control ("reflex") loops to sensors 128 and actuators 126 in accordance with the high level commands. Host computer 16 can send host commands to the microprocessor to select a type of force for the microprocessor to independently implement in a reflex loop. Microprocessor 410 can continually read data from sensors 128 for the position and motion of object 44 and compute forces on the object according to the sensor data, timing data from clock 413, and/or subroutines or reflex processes selected in accordance with the host commands. The processor then outputs a processor command to an actuator to apply the computed force. Such a process is described in greater detail in U.S. Pat. No. 5,729,811, assigned to the same assignee as the present application and incorporated by reference herein.

Microprocessor 410 can also receive commands from any other input devices 412 included on mechanical apparatus 25 or interface 14' and provides appropriate signals to host computer 16 to indicate that the input information has been received and any information included in the input information. For example, buttons, switches, dials, or other input controls associated with apparatus 25 14 can provide signals to microprocessor 410

In the preferred embodiment, interface 14' is included in a housing to which mechanical apparatus 25 and user object 44 is directly or indirectly coupled. Alternatively, microprocessor 410 and/or other electronic components of interface device 14' can be provided in a separate housing from user object 44, apparatus 25, sensors 128, and actuators 126.

Sensors 128 sense the position, motion, and/or other characteristics of user object 44 of the mechanical apparatus 25 along one or more degrees of freedom and provide signals to microprocessor 410 including information representative of those characteristics. Examples of embodiments of user objects and movement within provided degrees of freedom are described above with respect to FIGS. 2–8. Typically, a sensor 128 is provided for each degree of freedom along which object 44 can be moved. Alternatively, a single compound sensor can be used to sense position or movement in multiple degrees of freedom. Examples of sensors suitable for several embodiments described herein, such as digital optical rotary encoders, are described above. Linear optical encoders may similarly sense the change in position of object 44 along a linear degree of freedom.

Sensors 128 provide an electrical signal to an optional sensor interface 130, which can be used to convert sensor signals to signals that are provided to and can be interpreted by the microprocessor 410 and/or host computer 16. Alternately, microprocessor 410 can perform these sensor interface functions without the need for a separate sensor interface 130. The sensor signals can be processed by microprocessor 410 and may also be sent to host computer 16 which updates the host application program and sends force control signals as appropriate. Other interface mechanisms can also be used to provide an appropriate signal to host computer 16. In alternate embodiments, sensor signals from sensors 128 can be provided directly to host computer 16, bypassing microprocessor 410. Also, sensor interface 130 can be included within host computer 16, such as on an interface board or card. Alternatively, as described above, an analog sensor can be used instead of digital sensor for all or some of the sensors 128.

Other types of interface circuitry 36 can also be used. For example, an electronic interface is described in abovementioned U.S. Pat. No. 5,576,727. The electronic interface described therein has six channels corresponding to the six degrees of freedom of a stylus. The interface allows the position of the mouse or stylus to be tracked and provides force feedback to the mouse using sensors and actuators. Sensor interface 130 can include angle determining chips to pre-process angle signals reads from sensors 128 before sending them to the microprocessor 410. For example, a data bus plus chip-enable lines allow any of the angle determining chips to communicate with the microprocessor. A configuration without angle-determining chips is most applicable in an embodiment having absolute sensors, which have output signals directly indicating the angles without any further processing, thereby requiring less computation for the microprocessor 410 and thus little if any preprocessing. If the sensors 128 are relative sensors, which indicate only the change in an angle and which require further processing for complete determination of the angle, then angle-determining chips are more appropriate.

In either configuration, if the microprocessor 410 is fast enough, it can compute object 44 position and/or orientation (or motion, if desired) on board the embodiment and send this final data through any standard communications interface such as bus 404 on to the host computer 16 and to display screen 20. If the microprocessor 410 is not fast enough, then the angles can be sent to the host computer 16 which can perform the calculations on its own.

Other variations may consist of microprocessor 410 which reads other input devices 412, obtains angles, possibly computes coordinates and orientation of the object 44, and supervises communication with the host computer 16. Another variation may consist of dedicated subcircuits and specialized or off-the-shelf chips which read the other input devices, monitor the sensors 128, determine angles, and handle communications with the host computer 16, all without software or a microprocessor 410.

Actuators 126 transmit forces to user object 44 of mechanical apparatus 25 in one or more directions along one or more degrees of freedom in response to signals received from microprocessor 410. Typically, an actuator 126 is provided for each degree of freedom along which forces are desired to be transmitted. As explained above, actuators 126 can include active actuators and/or passive actuators.

Actuator interface 414 can be optionally connected between actuators 126 and microprocessor 410. Interface 414 converts signals from microprocessor 410 into signals appropriate to drive actuators 126. Interface 414 can include power amplifiers, switches, digital to analog controllers (DACs), and other components. An example of an actuator interface for active actuators is described above with reference to FIGS. 9, 10 and 11. In alternate embodiments, interface 414 circuitry can be provided within microprocessor 410 or in actuators 126.

If one or more voice coils 240 are being used as actuators 126 to apply forces to object 44, as shown in FIG. 18, then microprocessor 410 and/or host computer 16 can command specific current magnitude and direction to the voice coil(s) 240 to apply desired forces to object 44. This is preferably accomplished using voice coil driver chips that can be provided in actuator interface 414. These chips typically include a self-contained transconductance amplifier, with a current control feedback loop, to output current to the voice coil actuator. A preferred voice coil driver chip includes a switchable transconductance gain circuit that allows the user to choose between two different voltage-to-current gains. When smaller, more fine forces are to be output, the gain can be switched from a high gain to a low gain, thus decreasing the current step size. This increases the resolution of the DAC used to drive the voice coil driver. With a greater resolution, the DAC can more finely and accurately control the forces felt by the user. This fine control, however, provides a smaller range of possible forces that can be output. Thus, when a larger range of forces is desired, the gain can be switched back to the larger gain. The gain switching can be implemented using a control line from the microprocessor 410 or computer 16 to the voice coil driver chip. Suitable voice coil driver chips include the Siliconex Si9961 (with gain control), the Allegro 8932A (with gain control), the Allegro 8958 (no gain control), and the Unitrode UC3176 (no gain control). The operation and implementation of these drivers is well known to those skilled in the art. In addition, such voice coil driver chips can be advantageously used with actuators other than voice coil actuators. For example, a servo motor can be provided with current and switchable gains from a voice coil driver chip that is inexpensive and conveniently implemented.

Other input devices 412 can optionally be included in the housing for mechanical apparatus 25 and send input signals to microprocessor 410. Such input devices can include buttons, dials, switches, or other mechanisms. For example, in embodiments where user object 44 is a joystick (as in FIG. 8), other input devices can include one or more buttons provided, for example, on the joystick handle or base and used to supplement the input from the user to a game or simulation. The operation of such input devices is well known to those skilled in the art.

Power supply 416 can optionally be coupled to actuator interface 414 and/or actuators 126 to provide electrical power. Active actuators typically require a separate power source to be driven. Power supply 416 can be included within the housing of mechanical apparatus 25, or can be provided as a separate component, for example, connected by an electrical power cord.

Safety switch 418 is preferably included in interface device to provide a mechanism to allow a user to override and deactivate actuators 126, or require a user to activate actuators 126, for safety reasons. Certain types of actuators, especially active actuators such as motors, can pose a safety issue for the user if the actuators unexpectedly move user object 44 against the user with a strong force. In addition, if a failure in the interface system occurs, the user may desire to quickly deactivate the actuators to avoid any injury. To provide this option, safety switch 418 is coupled to actuators 126. Safety switch 418 can be implemented such that the user must always hold or close the switch, so that if the user lets go, power to the actuators is cut off.

While this invention has been described in terms of several preferred embodiments, it is contemplated that alterations, modifications and permutations thereof will become apparent to those skilled in the art upon a reading of the specification and study of the drawings. For example, the linked members of apparatus 25 can take a number of actual physical sizes and forms while maintaining the disclosed linkage structure. In addition, other gimbal mechanisms can also be provided with a linear axis member 40 to provide three degrees of freedom. Likewise, other types of gimbal mechanisms or different mechanisms providing multiple degrees of freedom can be used with the capstan drive mechanisms disclosed herein to reduce inertia, friction, and backlash in a system. A variety of devices can also be used to sense the position of an object in the provided degrees of freedom and to drive the object along those degrees of freedom. In addition, the sensor and actuator used in the transducer system having desired play can take a variety of forms. Similarly, other types of couplings can be used to provide the desired play between the object and actuator. Furthermore, certain terminology has been used for the purposes of descriptive clarity, and not to limit the present invention. It is therefore intended that the following appended claims include all such alterations, modifications and permutations as fall within the true spirit and scope of the present invention.

What is claimed is:

1. An interface device for use with a host computer system displaying a graphical simulation on a screen and updating said graphical simulation in response to user manipulation of said interface device, said host computer commanding said interface device to generate force feedback sensations in coordination with events within said graphical simulation, said interface device comprising:

a joystick handle grasped by a user;

a support mechanism coupled to a grounding surface which supports said joystick handle while allowing two rotary degrees of freedom in the motion of said joystick handle with respect to said grounding surface;

two actuators for providing resistance to motion of said joystick handle along said two degrees of freedom, said actuators being grounded such that a portion of each of said two actuators remains stationary with respect to said grounding surface, thereby allowing said joystick handle to be moved while a substantial portion of each of said actuators remains stationary with respect to said grounding surface, said resistance to motion generated by said actuators in response to commands from said host computer;

a sensor system including an emitter and a detector, said detector including a photo diode and said emitter including an illumination source, said sensor system being grounded such that one of said emitter and said detector remains stationary with respect to said grounding surface and the other of said emitter and detector moves with respect to said grounding surface when said joystick handle is rotated about one of said degrees of freedom, resulting in motion of a beam from said illumination source with respect to said detector, and wherein said motion causes said sensor system to output signals that represent a position of said joystick handle along a degree of freedom; and a local microprocessor separate from said host computer system, said local microprocessor electrically coupled to said actuators and to said sensor system such that said local microprocessor controls said actuators and reads said signals from said sensor system, wherein said local microprocessor is coupled to said host computer via a communication interface, said local microprocessor executing a local process in parallel with said displaying and updating of said simulation by said host computer.

2. An interface device as recited in claim 1 wherein said photo diode is a lateral effect photo diode.

3. An interface device as recited in claim 1 wherein said local process involves execution of a plurality of local routines, wherein said plurality of local routines are stored in local memory coupled to said local microprocessor, and wherein at least one of said local routines is a force routine that controls said actuators in response to a decoded command received from said host computer, wherein an execution of said force routine is coordinated with an event occurring in the parallel host computer displaying and updating of said graphical simulation, thereby locally creating a meaningful feel sensation on said joystick handle that corresponds with a relevant displayed event within said graphical simulation.

4. An interface device as recited in claim 3 further including a user adjustable switch apparatus electrically coupled to said local microprocessor, said switch apparatus providing a state signal to said local microprocessor representing a state of said switch apparatus.

5. An interface device as recited in claim 4 wherein at least one of said local routines reports a representation of said state signal to said host computer, wherein said host computer updates said parallel execution of graphical simulation in response to said switch state.

6. An interface device as recited in claim 1 wherein said stationary portion of said actuators includes multiple grounded magnets and wherein a portion of said actuators that is not stationary with respect to said grounding surface includes a coil of wire.

7. An interface device as recited in claim 1 wherein said communication interface includes a PC game port.

8. An interface device as recited in claim 1 wherein said communication interface includes a Universal Serial Bus.

9. An interface device as recited in claim 1 wherein said support mechanism includes a gimbal.

10. An interface device as recited in claim 9 wherein said gimbal includes a ball joint.

11. An interface device as recited in claim 9 wherein said gimbal includes a plurality of members forming a closed loop linkage.

12. An interface device as recited in claim 1 wherein said actuator is coupled to said joystick handle through a tensioned cable drive system.

13. An interface device as recited in claim 1 wherein said joystick handle can be rotated about a third degree of freedom with respect to said grounding surface, said third degree of freedom being a spin axis along a length of said joystick handle.

14. An interface device as recited in claim 1 wherein said photo diode is a rectangular surface that can detect motion of said illumination source in a rectangular plane.

15. An interface device as recited in claim 14 wherein relative motion of said illumination source and said photo diode causes said sensor system to output signals that represent motion of said joystick handle in said two rotary degrees of freedom.

16. An interface device for use with a host computer that displays a graphical simulation and updates said graphical simulation in response to user manipulation of said interface device, wherein said host computer commands said interface device to generate force feedback sensations in coordination with events within said graphical simulation, said interface device comprising:
 a joystick handle grasped by a user;
 a support mechanism which supports said joystick handle while allowing two rotary degrees of freedom in the motion of said joystick handle with respect to a fixed surface;
 two actuators that provide resistance to motion of said joystick handle along said two degrees of freedom with respect to said fixed surface, said resistance to motion generated by said actuators in response to host signals from said host computer, wherein said two actuators include a magnet assembly and a coil assembly, said magnet assembly grounded to said fixed surface such that said magnet assembly is fixed to and remains stationary with respect to said fixed surface, thereby allowing said joystick handle to be moved without moving a mass of said grounded portions of said actuators;
 a photo diode sensor system including two portions, wherein one portion is grounded such that it remains fixed with respect to said magnet assembly of each of said actuators and the other portion is coupled to and moves with said joystick handle, said photo diode sensor system being configured such that rotary motion of said joystick handle causes relative motion between said two portions of said sensor which can be measured by said sensor to determine a position of said joystick handle in said two degrees of freedom; and
 a communication interface coupling said host computer to said interface device, said communication interface reporting data from said photo diode sensor system and controlling said actuators, said communication interface including a game port.

17. An interface device as recited in claim 16 wherein said photo diode sensor system includes a lateral effect photo diode.

18. An interface device as recited in claim 17 wherein said rotary motion of said joystick handle is converted to linear motion of said portion of said sensor coupled to said joystick handle.

19. An interface device as recited in claim 18 wherein said joystick handle and said portion of said sensor coupled to said joystick handle are coupled to a board moveable in an x-y plane when said joystick handle is moved in two rotary degrees of freedom.

20. An interface device as recited in claim 19 wherein said board is supported by a flexure connected to said fixed surface.

21. An interface device as recited in claim 19 wherein a ball joint is coupled to said joystick handle and converts said rotary motion of said joystick to said linear motion of said sensor portion.

22. An interface device as recited in claim 16 wherein said actuators include voice coil actuators including at least one magnet assembly and a coil assembly.

23. An interface device as recited in claim 17 wherein said portion of said photo diode sensor system coupled to said fixed surface is an emitter and said portion of said sensor coupled to said joystick handle is a rectangular detector.

24. An interface device as recited in claim 23 wherein said rectangular detector senses the location of a beam provided by said emitter on said rectangular detector.

25. An interface device for use with a host computer that displays a graphical simulation and updates said graphical environment in response to user manipulation of said interface device, said host computer commanding said interface device to generate force feedback sensations in coordination with events within said graphical environment, said interface device comprising:
 a user object grasped by a user;
 a support mechanism which supports said user object while allowing two degrees of freedom in the motion of said user object with respect to a grounding surface;
 two grounded actuators coupled to said support mechanism and providing a force resistance to motion of said user object along said two degrees of freedom with respect to said grounding surface, said resistance to motion generated by said actuators in response to commands from said host computer, said actuators each including a magnet assembly fixed to said grounding surface and a coil assembly coupled to and moving with said user object;

a grounded sensor system including an optical detector and a beam source, wherein one of said optical detector and said beam source is fixed with respect to said magnet assembly and the other of said optical detector and said beam source is coupled and moves with said user object, and wherein said sensor system is configured to detect motion of said user object with respect to said grounding surface in said two degrees of freedom; and a local microprocessor separate from said host computer, said local microprocessor electrically coupled to said grounded actuators and to said grounded sensor system such that said local microprocessor controls said actuators and reads said sensor system, said local microprocessor coupled to said host computer by a Universal Serial Bus interface and executing a local process in parallel with host execution of said graphical environment.

26. An interface device as recited in claim 25 wherein said user object is a joystick handle.

27. An interface device as recited in claim 25 wherein said optical detector is a photo diode.

28. An interface device as recited in claim 27 wherein said degrees of freedom of said user object are rotary degrees of freedom.

29. An interface device as recited in claim 27 wherein said degrees of freedom of said user object are linear degrees of freedom.

30. An interface device for use with a host computer that displays and executes a graphical environment and updates said graphical environment in response to user manipulation of said interface device, said host computer commanding said interface device to generate force feedback sensations in coordination with interactions between a user-controlled graphical cursor and said graphical environment, said interface device comprising:

a user object grasped by a user;

a support mechanism which supports said user object while allowing two linear degrees of freedom in the motion of said user object with respect to a grounding surface;

two actuators grounded to said grounding surface and by producing a force upon said user object in said two linear degrees of freedom with respect to said grounding surface, said force causing a resistance to motion of said user object generated by said actuators in response to commands from said host computer;

a grounded sensor system including a lateral effect photo diode and an illumination source, wherein one of said lateral effect photo diode and said illumination source is grounded to said grounding surface, said sensor system configured to detect motion of said user object with respect to said grounding surface in at least one of said two linear degrees of freedom;

a local microprocessor separate from said host computer, said local microprocessor electrically coupled to said actuators and to said grounded sensor system such that said local processor can control said actuators and read said grounded sensor system, said local microprocessor coupled to said host computer by a Universal Serial Bus interface, said local microprocessor executing a local process in parallel with execution of said graphical environment by said host computer; and a user adjustable switch apparatus electrically coupled to said local microprocessor, said switch apparatus providing a state signal to said local microprocessor representing a state of said switch, wherein said local microprocessor reports a representation of said state signal to said host computer such that said host computer updates said graphical environment in response to said switch state.

31. An interface device as recited in claim 30 wherein said sensor system is configured to detect motion of said user object with respect to said grounding surface in said two linear degrees of freedom.

32. An interface device as recited in claim 31 wherein said photo diode includes a planar detector.

33. An interface device as recited in claim 30 wherein said user object is a joystick handle.

34. A method for interfacing an interface device with a host computer that displays a graphical simulation and updates said graphical simulation in response to user manipulation of said interface device, wherein said host computer commands said interface device to generate force feedback sensations in coordination with events within said graphical simulation, said method comprising:

providing a joystick handle for a user to grasp;

supporting said joystick handle and providing two degrees of freedom in the motion of said joystick handle with respect to a fixed surface;

resisting motion of said joystick handle along said two degrees of freedom with respect to said fixed surface in response to host signals from said host computer, said resisting being performed using actuators including a magnet assembly and a coil assembly, said magnet assembly grounded to said fixed surface such that said magnet assembly is fixed to and remains stationary with respect to said fixed surface and said coil assembly fixed to and moving with said joystick handle, thereby allowing said joystick handle to be moved without moving a mass of said magnet assembly of said actuators;

determining a position of said joystick handle in said two degrees of freedom using a photo diode sensor system, said sensor system including two portions, wherein one portion is grounded such that it remains fixed with respect to said magnet assembly of each of said actuators and the other portion is coupled to and moves with said joystick handle, wherein motion of said joystick handle causes relative motion between said two portions of said sensor system which can be measured by said sensor system to determine said position of said joystick handle; and reporting data from said sensor system to said host computer and controlling said actuators using a communication interface coupling said interface device to a game port of said host computer.

* * * * *